(12) United States Patent
Archambault

(10) Patent No.: US 6,916,622 B2
(45) Date of Patent: Jul. 12, 2005

(54) REGIONS OF PAPILLOMA VIRUS E1 HELICASE INVOLVED IN E1 OLIGOMERIZATION

(75) Inventor: Jacques Archambault, Rosemère (CA)

(73) Assignee: Boehringer Ingelheim (Canada) Ltd., Laval (CA)

(*) Notice: Subject to any disclaimer, the term of this patent is extended or adjusted under 35 U.S.C. 154(b) by 0 days.

(21) Appl. No.: 10/339,268

(22) Filed: Jan. 9, 2003

(65) Prior Publication Data

US 2004/0002059 A1 Jan. 1, 2004

Related U.S. Application Data

(62) Division of application No. 09/744,202, filed as application No. PCT/CA99/00657 on Jul. 20, 1999, now abandoned.
(60) Provisional application No. 60/093,626, filed on Jul. 21, 1998.

(51) Int. Cl.$^7$ .................................................. C12Q 1/68
(52) U.S. Cl. ........................ 435/6; 435/91.1; 435/7.71
(58) Field of Search ......................... 435/6, 7.71, 91.1, 435/7.45; 424/204.1

(56) References Cited

U.S. PATENT DOCUMENTS

| 5,601,973 A | 2/1997 | Mueller et al. |
| 5,821,048 A | 10/1998 | Howley et al. |

FOREIGN PATENT DOCUMENTS

| EP | 0 523 395 A | 1/1993 |
| WO | WO 96 41018 A | 12/1996 |
| WO | WO 99/57283 | * 11/1999 |

OTHER PUBLICATIONS

Sun, Y. et al: "Active domains of human papillomavirus type 11 E1 protein for origin replication"; Journal of General Virology, vol. 79, Jul. 3, 1998, pp. 1651–1658.

Sedman, J. et al; "the initiator protein E1 binds to the bovine papillomavirus origin of repplication as a trimeric ring. like structure"; EMBO Journal, vol. 15, No. 18, 1996, pp. 5085–5092.

Lusky, M. et al; "The bovine papillomavirus E2 protein modulates the assembly of but is not stably maintained in a replication–competent multimeric E1–replication origin complex"; Proc. Nat'l Acad. Sci. USA, vol. 91, Sep. 1994, pp. 8895–8899.

S–Y Chan, et al; "Phylogenetic analysis of 48 papillomavirus types and 28 subtypes and variants: a showcase oft te molecular evolution of DNA viruses"; Journal of Virology, US, New York, US, vol. 66, No. 10, pp. 5714–5725.

* cited by examiner

*Primary Examiner*—Ali R. Salimi
(74) *Attorney, Agent, or Firm*—Michael P. Morris; Mary-Ellen M. Devlin; Susan K. Pocchiari

(57) ABSTRACT

There is provided an amino acid sequence comprised within the PV E1 protein region A delineated by amino acids 352 and 439, and any derivative variant or fragment thereof, necessary for the oligomerization of the E1 protein. This amino acid sequence is capable of self-association and of associating with the full length E1 protein and any derivative, variant or fragment thereof comprising the sequence of this invention. A specific aspect of this first embodiment, the amino acid domain of this invention delimited by amino acids 353 to 438 of the PV E1 protein. More particularly, the amino acid domain of this invention is as defined by SEQ ID NO. 2. There is also provided a cross-linking assay to directly measure the level of oligomerization (or inhibition thereof) of the E1 protein. In accordance with a fourth embodiment of this invention, there is provided a N-terminally truncated E1 protein. More particularly, one aspect of this fourth embodiment encompasses the E1 protein delimited by amino acid 72 to 649 (SEQ ID NO. 78).

12 Claims, 16 Drawing Sheets

FIGURE 1B

| Construct | | BD-E1 (330-649) | BD |
|---|---|---|---|
| 1 — A B C D 649 | | | |
| 1 ———— 649 | | 3.17 | 0.67 |
| 353 ———— 649 | | 54.73 | 0.22 |
| 353 ———— 572 | | 13.91 | 0.56 |
| 353 ———— 536 | | 12.76 | 0.46 |
| 353 ———— 458 | | 12.97 | 0.56 |
| 353 ———— 444 | | 18.12 | 0.35 |
| 353 ———— 438 | | 25.25 | 0.20 |
| 353 ———— 431 | | 22.72 | 0.32 |
| 353 ———— 416 | | 2.15 | 0.19 |
| 365 ———— 458 | | 0.58 | 0.48 |
| 377 ———— 458 | | 0.62 | 0.56 |
| 384 ———— 458 | | 0.55 | 0.54 |
| 387 ———— 458 | | 0.63 | 0.50 |
| 405 ———— 458 | | 0.76 | 0.57 |
| 416 ———— 458 | | 0.66 | 0.44 |
| | | 0.62 | n.d. |
| GAL4-AD Vector | | 0.96 | 0.64 |

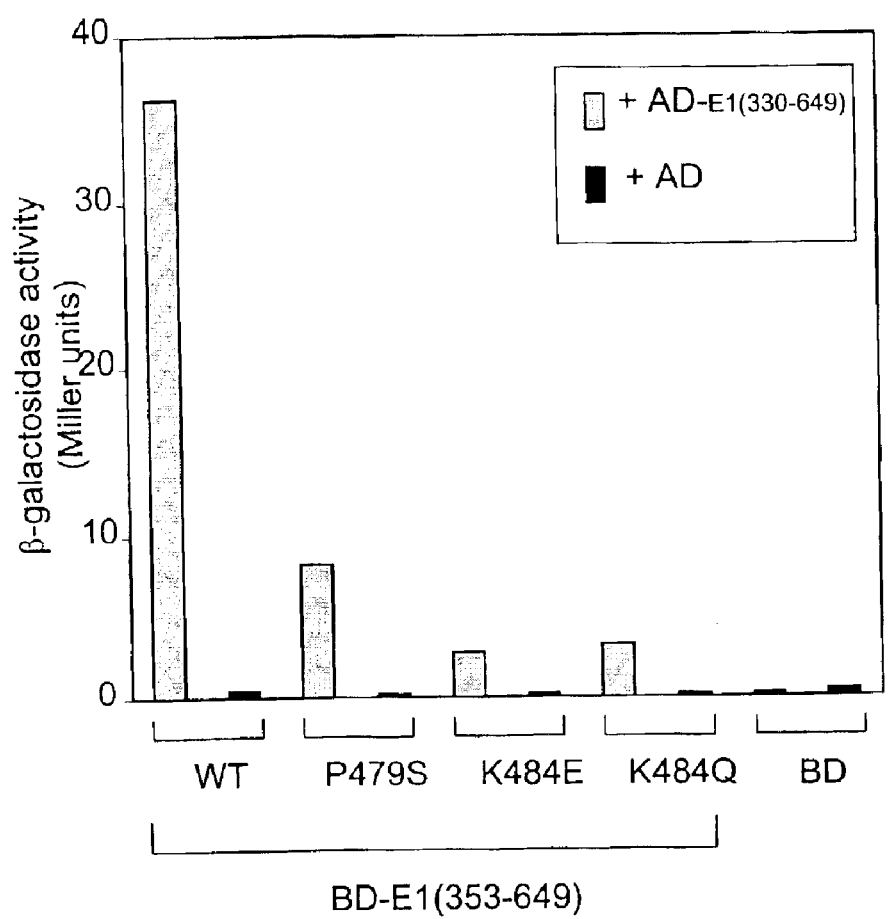

FIGURE 4
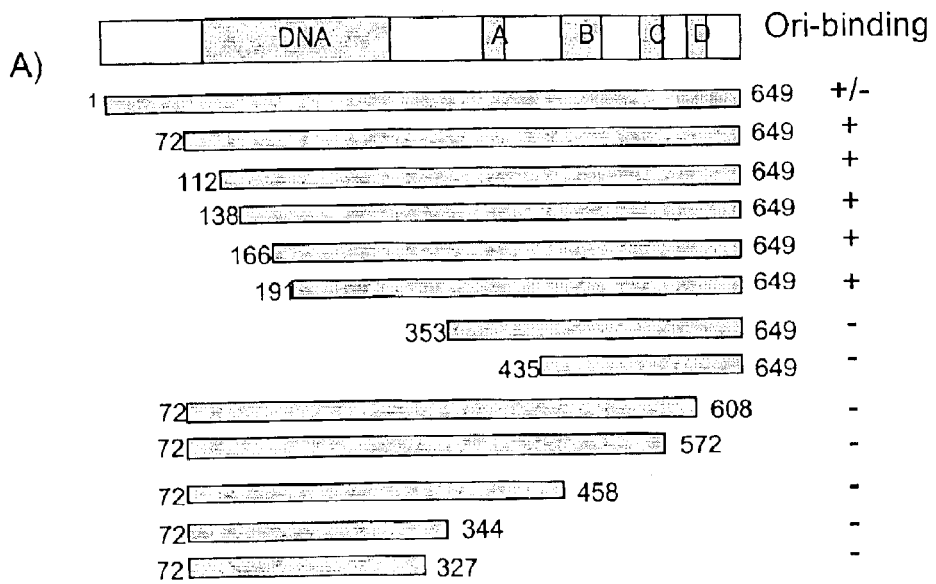
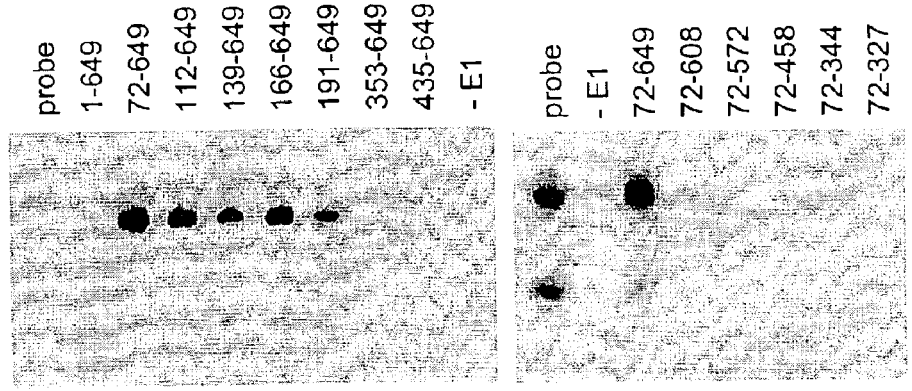

FIGURE 7
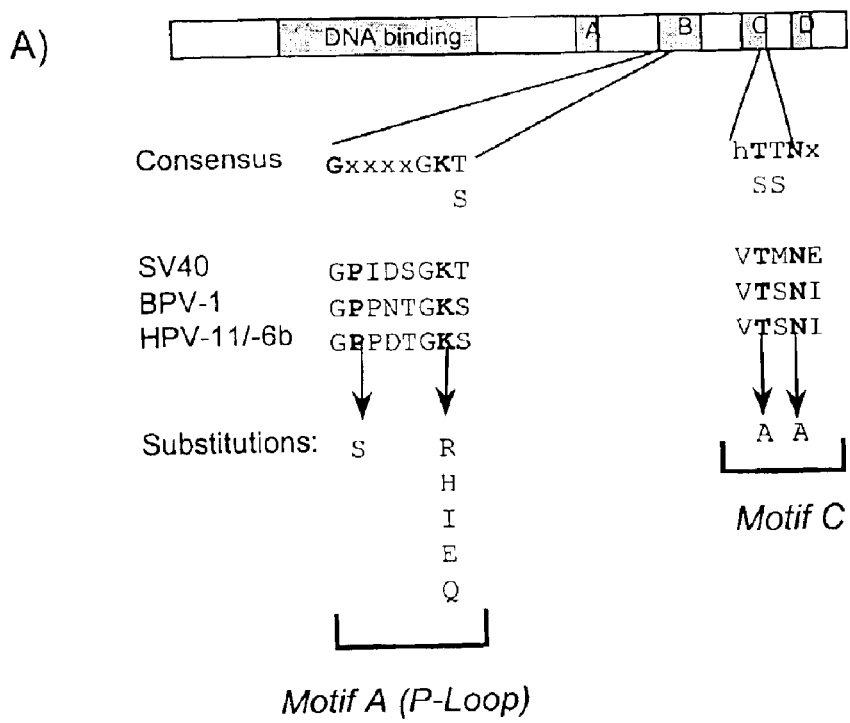
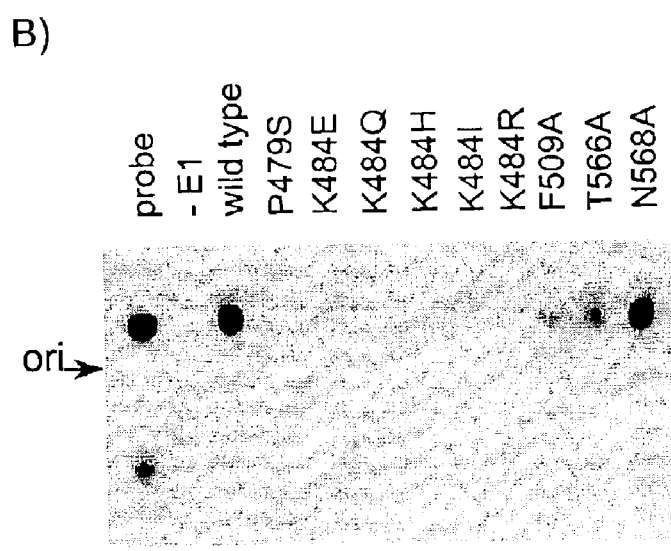

FIGURE 9
A)
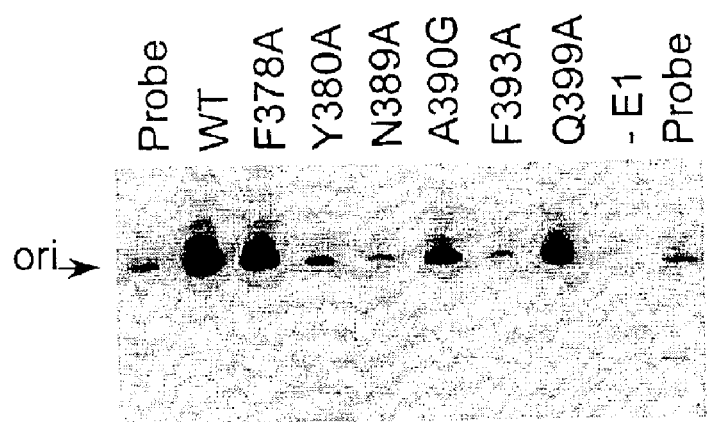
B)
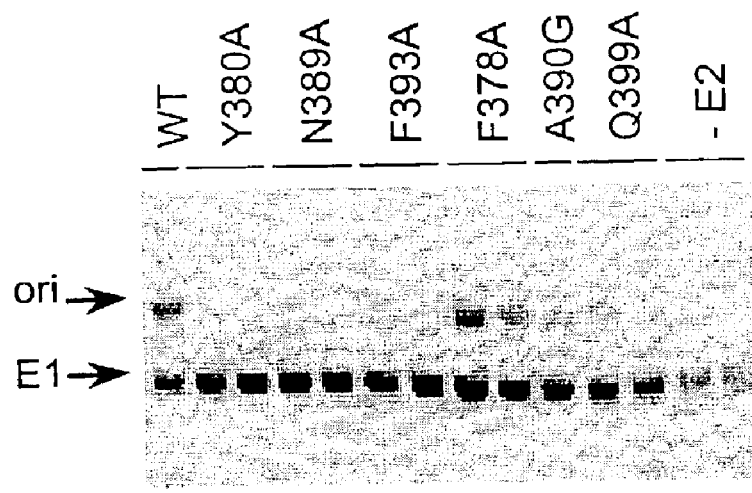

REGIONS OF PAPILLOMA VIRUS E1 HELICASE INVOLVED IN E1 OLIGOMERIZATION

RELATED APPLICATIONS

This application is a division of U.S. Ser. No. 09/744,202 (now abandoned), filed Jan. 19, 2001, which is a national stage application of PCT/CA99/00657, filed on Jul. 20, 1999, which claims the benefit under 35 USC 119(e) of U.S. Provisional Application Ser. No. 60/093,626, filed on Jul. 21, 1998, the disclosures of all of which are incorporated by reference in their entireties.

FIELD OF THE INVENTION

The present invention relates to an amino acid sequence comprised in the papilloma virus E1 protein, necessary for the homo-oligomerization of the E1 protein. This oligomerization, is an essential step in the initiation of viral DNA replication. Further, the invention discloses a screening method and a screening system capable of selecting agents capable of interfering with this protein-protein interaction. Moreover, the invention further relates to a system for the selection of agents capable of modulating this protein-protein interaction for use in the treatment and control of PV infections in animals.

BACKGROUND OF THE INVENTION

Papillomaviruses (PV) are non-enveloped DNA viruses that induce hyperproliferative lesions of the epithelia. The papillomaviruses are widespread in nature and have been recognized in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types of papillomavirus (HPV) that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases comprising cervical carcinomas (Fields, 1996, Virology, 3rd ed. Lippincott—Raven Pub., Philadelphia, N.Y.).

There are more than 25 HPV types that are implicated in anogenital diseases, these are grouped into "low risk" and "high risk" types. The low risk types include HPV type 6, type 11 and type 13 and induce mostly benign lesions such as condyloma acuminata (genital warts) and low grade squamous intraepithelial lesions (SIL). In the United States there are approximately 5 million people with genital warts of which 90% is attributed to HPV-6 and HPV-11. About 90% of SIL is also caused by low risk types 6 and 11. The other 10% of SIL is caused by high risk HPVs.

The high risk types are associated with high grade SIL and cervical cancer and include most frequently HPV types 16, 18, 31, 33, 35, 45, 52, and 58. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide (Fields, 1996, supra).

Treatments for genital warts include physical removal such as cryotherapy, $CO_2$ laser, electrosurgery, or surgical excision. Cytotoxic agents may also be used such as trichloroacetic acid (TCA), podophyllin or podofilox. Immunomodulatory agents are also available such as Interferon or Imiquimod. These treatments are not completely effective in eliminating all viral particles and there is either a high cost incurred or uncomfortable side effects related thereto. In fact, there are currently no effective antiviral treatments for HPV infection. With all current therapies recurrent warts are common (Beutner & Ferenczy, 1997, Amer. J. Med., 102 (5A):28–37).

The ineffectiveness of the current methods to treat HPV infections has demonstrated the need to identify new means to control or eliminate such infections. In recent years, efforts have been directed towards finding antiviral compounds, and especially compounds capable of interfering with viral replication (Hughes and Romanos, 1993, Nucleic Acids Res. 21:5817–5823; Clark et al., Antiviral Res., 1998, 37(2):97–106; Hajduk etal., 1997, J. Med. Chem., 49(20):3144–3150 and Cowsert et al., 1993, Antimicrob. Agents. Chemother., 37(2):171–177). To that end, it has therefore become important to study the genetics of HPVs in order to identify potential chemotherapeutic targets to contain and possibly eliminate any diseases caused by HPV infections.

The life cycle of PV is closely coupled to keratinocyte differentiation. Infection is believed to occur at a site of tissue disruption in the basal epithelium. Unlike normal cells, cellular division continues as the cell undergoes vertical differentiation. As the infected cells undergo progressive differentiation, the cellular machinery is maintained which allow viral gene expression to increase, with eventual late gene expression and virion assembly in terminally differentiated keratinocytes and the release of viral particles (Fields, supra).

The coding strand for each of the papillomavirus contains approximately ten designated translational open reading frames (ORFs) that have been classified as either early ORFs or late ORFs. The E1 to E8 genes are expressed early in the viral replication cycle. The two late genes (L1 and L2) code for the major and minor capsid proteins respectively. The E1 and E2 gene products function in viral DNA replication, whereas E5, E6 and E7 modulate host cell proliferation. The L1 and L2 are involved in virion structure. The functions of E3, E4 and E8 gene products is uncertain at present.

Studies of HPV have shown that proteins E1 and E2 are the only viral proteins required for viral DNA replication in vitro (Kuo et al., 1994, J. Biol. Chem. 30: 24058–24065). This requirement is similar to that of bovine papillomavirus type 1 (BPV-1). Indeed, there is a high degree of similarity between E1 and E2 proteins and the ori-sequences of all papillomaviruses (PV) regardless of the viral species and type (Kuo et al., 1994, supra). Of note, E1 is the most highly conserved protein in PV and its enzymatic activity is presumed to be similar for all PV types (Jenkins, 1996, J. Gen. Virol. 77:1805–1809). It is therefore expected that all E1 gene products from different PV have similar structure and function. In addition PV E1 protein shows sequence and structural similarities to the simian virus 40 and polyomavirus large T protein (Clertant and Seif, 1984, Nature 311:276–279 and Mansley et al., 1997, J. Virology 71:7600–7608).

The E2 protein is a transcriptional activator that binds to E1 protein, these two proteins and the ori sequence form a ternary complex (Mohr et al., 1990, Science 250:1694–1699). It is believed that E2 enhances binding of E1 to the BPV origin of replication (Seo et al., 1993b, Proc. Natl. Acad. Sci., 90:2865–2869). In HPV, Lui et al. suggested that E2 stabilizes E1 binding to the ori (1995, J. Biol. Chem. 270(45):27283–27291 and McBride et al., 1991, J. Biol. Chem 266:18411–18414).

Evidence emanating from studies of BPV-1 have shown that E1 possesses ATPase and helicase activities that are required in the initiation of viral DNA replication (Seo et al., 1993a, Proc. Natl. Acad. Sci. USA 90:702–706; Yang et al., 1993, Proc. Natl. Acad. Sci. 90:5086–5090; and MacPherson et al., 1994, Virology 204:403–408).

The E1 protein from BPV is a phosphorylated nuclear protein having replication related functions. These include DNA and ATP binding, and, ATPase and helicase activities. Deletion mapping studies have identified the amino acids 121–311 as the region required for DNA binding. Mutations within this region obviate DNA binding by full length E1 protein (Leng et al, 1997, J. Virol. 71:848–852 and Thorner et al., 1993, Proc. Natl. Acad. Sci. USA 90:898–902). The second function, ATP binding and ATPase activities are essential for viral DNA replication. Point mutations within conserved regions in the ATP binding domain, inactivate the ability of E1 to bind or hydrolyze ATP with the concomitant loss of DNA replication (MacPherson et al., 1994, Virology 204:403–408; Raj and Stanley, 1995, J. Gen. Virol. 76:2949–2956 and Sun et al., 1990, J. Virol 64:5093–5105). The third activity possessed by the E1 protein, is the helicase activity or the unwinding of DNA ahead of the replication fork. Studies have predicted that helicase activity resides from the DNA binding domain, amino acid 121 through the ATPase/nucleotide binding region, approximately amino acid 530 (Sverdrup and Myers, Human Papillomaviruses, 1997, Published by Theoretical Biology and Biophysics).

When viral DNA replication proceeds in vitro, where E1 protein is present in excess, replication proceeds in the absence of E2. In vivo, in the presence of a vast amount of cellular DNA, replication requires the presence of both E1 and E2. E2, acts as a specificity factor in directing E1 to the origin of replication (Sedman and Stenlund, 1995, Embo. J. 14:6218–6228). The mechanism for initiating replication in vivo, is believed to involve the cooperative binding of E1 and E2 to the origin, whereby E1 and E2 form a complex. These interactions of DNA-protein and protein-protein occur at the origin of DNA replication (Sverdrup and Myers, supra).

Understanding the mechanisms of the E1 protein as a helicase, presumably capable of unwinding the DNA at the origin and ahead of the replication fork, is one of the advantages of this invention. Based on PV studies and SV40 DNA replication, a biphasic model for replication initiation for PV has been proposed (Sverdrup and Myers, supra). In a first step, E1 and E2 cooperatively bind to the origin of replication, thus ensuring binding specificity towards the origin of replication. In a second step, additional E1 monomers are recruited to the origin with the concomitant loss of E2. It is thought that the formation of the E1 homo-oligomeric complex at the origin is required for DNA replicating activity and the recruitment of the cellular replication machinery in initiating DNA synthesis (Sverdrup and Myers, supra).

Since there are as yet no effective therapeutic agents to prevent, control, decrease or eliminate PV infection, it has become important to study the life cycle of PV in greater detail and to specifically develop a better understanding of viral DNA replication. There is surprisingly little knowledge about the mechanism of E1 oligomerization in-vivo or in-vitro. The prior art is silent as to the location of the region along the E1 protein that is necessary for this protein-protein interaction, in the formation of the E1 oligomeric complex.

There thus remains a need to provide an understanding of the mechanism and the element/s involved in this oligomerization. Knowledge of this process provides a potentially new therapeutic target against PV.

It is therefore, one of the advantages of the present invention to identify an amino acid region in the E1 protein necessary for this apparent self-association.

Further, localization of this region by the Applicant provides a potential new therapeutic target in the treatment of PV infections. It is therefore a further advantage of the invention to provide a screening method for identifying agents capable of modulating this new target and a system to select at least one such agent capable of interfering with PV DNA replication.

The present invention refers to a number of documents, the content of which is herein incorporated by reference.

SUMMARY OF THE INVENTION

The present invention concerns the elucidation of some of the steps necessary for initiating papillomavirus DNA replication. More particularly, the role of E1 protein (a.a. 1–649)(SEQ ID No. 1) in viral DNA replication. Most particularly the requirement for PV E1 protein oligomerization, as a step preceding viral DNA unwinding and DNA replication.

Therefore, in accordance with the first embodiment of the present invention, there is provided an amino acid sequence comprised within the PV E1 protein region A delineated by amino acids 352 and 439, and any derivative variant or fragment thereof, necessary for the oligomerization of the E1 protein. This amino acid sequence is capable of self-association and of associating with the full length E1 protein and any derivative, variant or fragment thereof comprising the sequence of this invention.

In accordance with this first embodiment, there is provided an amino acid sequence necessary for the oligomerization of PV E1 protein. This amino acid region or domain, as numbered from the amino acid sequence of human papilloma virus (HPV) type 11, is delineated by amino acids 352 and 439. Any derivative, variant or fragment of this amino acid region capable of demonstrating the same structural and functional activity is within the scope of this invention. In a particular aspect of this first embodiment, the amino acid sequence is further delineated by amino acids 352 and 432. In a more particular aspect of this first embodiment the amino acid sequence is further delineated by amino acids 352 and 417. The Applicant was the first to identify this domain comprised within the PV E1 protein as the amino acid sequence necessary for E1 protein oligomerization, which is an essential prerequisite step in the initiation of viral DNA replication. Therefore, in a specific aspect of this first embodiment, the amino acid domain of this invention delimited by amino acids 353 to 438 of the PV E1 protein. More particularly, the amino acid domain of this invention is as defined by SEQ ID NO. 2.

The Applicant was also the first to recognize that the elucidation of this amino acid sequence provides a new therapeutic target for the control, prevention, elimination and treatment of PV infections in mammals.

Therefore, in accordance with a second embodiment of this invention there is provided a screening assay for assessing the E1/DNA binding (hence oligomerization of E1 protein) by detecting and/or measuring the amount of DNA co-precipitated with the E1 protein.

Without wishing to be bound by theory, the Applicant has hypothesized that measurement of E1 self-oligomerization may be correlated indirectly by measurement of DNA co-immunoprecipitated with this E1 protein. By analogy with BPV E1, the Applicant anticipated that oligomerization of E1 would occur upon binding to the origin such that measuring the amount of ori bound to E1 would be an indirect measurement of oligomerized E1 protein.

Applicant has now proven that this hypothesis is correct by the design of a cross-linking assay and showing correlation between this cross-linking assay and the oligomerization assay according to earlier embodiments of this invention.

Therefore, in accordance with a third embodiment of this invention, there is provided a cross-linking assay to directly measure the level of oligomerization (or inhibition thereof) of the E1 protein.

In accordance with a fourth embodiment of this invention, there is provided a N-terminally truncated E1 protein. More particularly, one aspect of this fourth embodiment encompasses the E1 protein delimited by amino acid 72 to 649 (SEQ ID No. 78).

Other objects, advantages and features of the present invention will become more apparent upon reading of the following non-restrictive description of the preferred embodiments with reference to the accompanying drawings which is exemplary and should not be interpreted as limiting the scope of the present invention.

BRIEF DESCRIPTION OF THE DRAWINGS

Having thus generally described the invention, reference will now be made to the accompanying drawings, showing by way of illustration a preferred embodiment thereof, and in which:

FIG. 1B shows a diagram of the C-terminus E1 protein, indicating the position of conserved regions A to D. The N-terminal truncated E1 molecules, having a series of C-terminal deletions are fused to the GAL4 AD and co-transfected with a truncated N-terminal E1 (330–649 of SEQ ID No. 1) fused to GAL4 BD. The portions of E1 comprised in these fusion products are indicated, as well as the levels of β-galactosidase activity. In this experiment it is demonstrated that the fusion product comprised of the protein fragment (353–416; SEQ ID No. 4) leads to measurable β-galactosidase activity.

FIG. 2 shows the effect of amino acid substitutions in the conserved ATP-binding domain on E1—E1 interaction. Using the yeast two-hybrid system, β-galactosidase activity was measured in yeast cells co-transfected with wild type E1 (330–649) fused to the GAL4-AD and a wild type E1 (353–649; SEQ ID No. 5) or a mutant derivative [P479S (SEQ ID No. 6), K484E (SEQ ID No. 7) and K484Q (SEQ ID No. 8)] fused to the GAL4-BD. Plasmids with GAL4-AD and GAL4-BD alone were used for controls. It is shown that the substitutions in the Walker A motif (P-loop) of E1, decrease the amount of β-galactosidase activity, demonstrating that these substitutions compromise the ability for E1 to self-associate.

FIG. 4A shows a schematic representation of the series of deletions generated to map the domain of E1 required for binding to the viral origin of DNA replication in vitro. Truncated E1 proteins were produced in vitro and assayed for binding to the viral origin as described for FIG. 3A. N-terminally truncated proteins were immunoprecipitated using a polyclonal antibody directed against the C-terminus of E1. C-terminally truncated proteins were tagged at their N-terminus with the FLAG epitope and immunoprecipitated using an anti-FLAG monoclonal antibody.

FIG. 4B shows the results of the deletions shown in 4A. The autoradiograph demonstrates that the region of E1 necessary for binding to the origin comprises amino acids 191–649 which includes the amino acid sequence of this invention necessary for E1—E1 oligomerization. Deletions at the C-terminus abolish origin-binding.

FIG. 7A shows a schematic representation of the E1 protein. Grey boxes indicate the positions of region A, B, C and D that have high sequence similarity with large T antigens from SV40 and polyomaviruses, and of the DNA-binding domain. The locations of conserved motifs A and C that are present in members of superfamily 3 of NTP-binding proteins are indicated along with an alignment of these motifs from SV40 T antigen, BPV-1 and HPV-11 and HPV-6b. The consensus amino acid sequence of each motif is indicated. Residues that were mutated are indicated by an arrow.

FIG. 7B shows the results of E1* (SEQ ID No. 78), or the indicated mutant derivatives, tested for binding to the viral origin as described in FIG. 4A. The results show that substitutions in the conserved residues in the A motif, reduced the ability of E1 to bind to the origin, indicating that ATP binding to E1 is important in E1 binding to the origin. Substitutions in motif C did not appear to affect binding of E1 to the origin.

FIG. 9A shows the effect of substitutions in conserved region A of E1 on formation of the E1–E2-ori complex in vitro, and on transient HPV DNA replication in cells. Effect on formation of the E1–E2-ori complex in vitro. DNA-protein complexes were assembled without E1 (−E1), or with either wild type E1 (1–649; SEQ ID No. 1) or the indicated mutant E1 carrying substitutions in conserved region A. Complexes were immunoprecipitated with an antibody directed against E1, and the bound DNA was visualized by electrophoresis and autoradiography. Three of the substitutions Y389A (SEQ ID No. 9); F393A (SEQ ID No. 10) and N389A (SEQ ID No. 11)show a substantial reduction in complex formation. Two substitutions A390G (SEQ ID No. 12) and Q399A (SEQ ID No. 13) show a less pronounced effect and the substitution F378A (SEQ ID No. 14) appears to show a modest effect. These results indicate that this conserved A region, plays a role in the formation of E1–E2-ori complex.

FIG. 9B shows the effect of the six substitutions on transient HPV replication. The amount of replicated origin-containing plasmid (ori), or of an internal control plasmid (E1-expressing plasmid, E1), was detected by quantitative PCR analysis. PCR amplification was performed on genomic DNA isolated from cells transfected with a plasmid expressing E1 (−E2), or transfected with a combination of plasmids expressing E2 and E1 (either wild type or the indicated mutant E1 proteins). All cells were also transfected with the origin-containing plasmid pN9. PCR products were visualized by electrophoresis and autoradiography. The mutant E1 proteins with substitutions F378A (SEQ ID No. 14), A390G (SEQ ID No. 12) and Q399A (SEQ ID No. 13) show reduced levels of replication, the three other mutants showed no demonstrable replication activity. These results indicate that region A is important for transient HPV DNA replication.

DETAILED DESCRIPTION OF THE PREFERRED EMBODIMENTS

Definitions

Figure 1A:
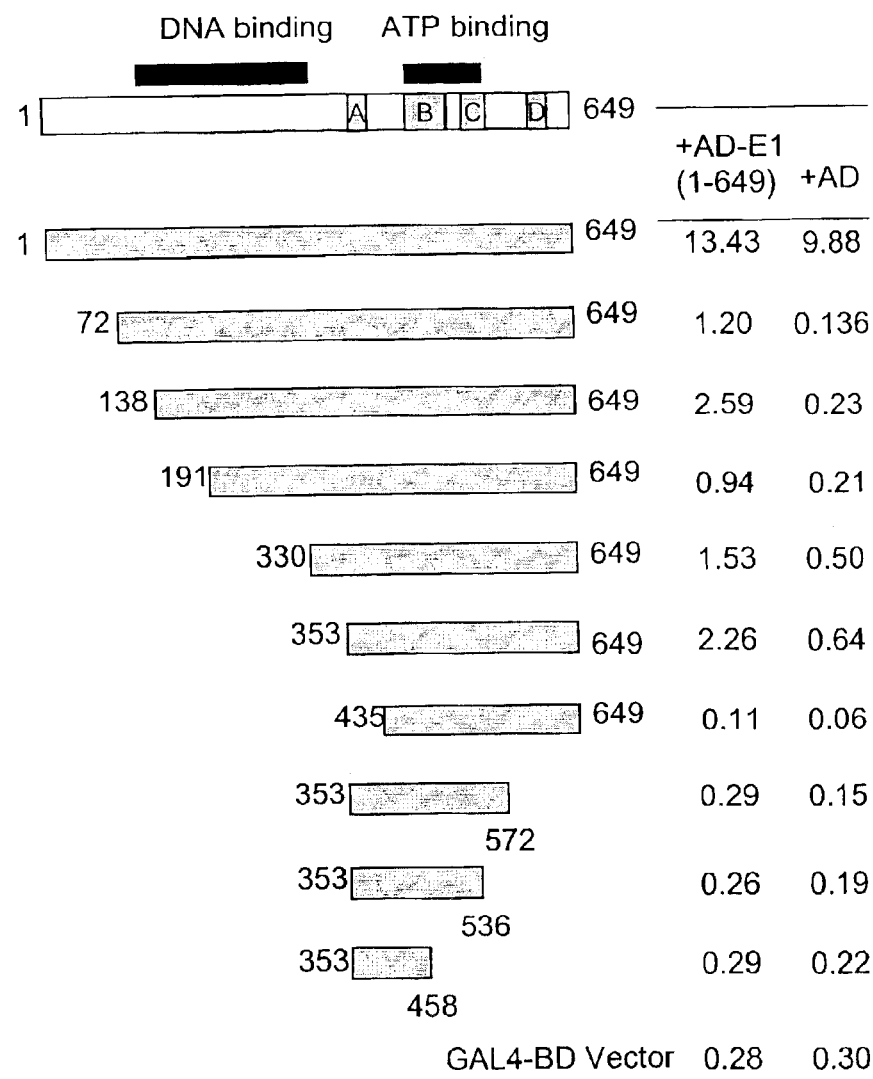
FIG. 1A shows the results of the E1—E1 interaction in the yeast two-hybrid system used to map the E1 protein region necessary for protein-protein interaction. In this system a fusion product of GAL4 activating domain (AD) and a full length E1 protein (amino acid 1–649; SEQ ID No. 1) is co-transfected with fusion products comprised of a series of deletions at the N-terminus of the HPV 11 E1 protein and the DNA-binding domain (BD) of GAL4. High transcriptional activity is present only when the interaction of the two proteins in the hybrid molecules interact sufficiently to bring the GAL4 AD and BD into close proximity so as to allow GAL4 transcriptional activity. A diagram of the E1 protein is shown at the top of the figure. Grey boxes labeled A, B, C, and D represent regions of E1 that have a high sequence similarity with large T antigens from SV40 and polyomaviruses. Black boxes indicate the position of the DNA- and ATP-binding domains of E1. The portions of E1 comprised in these fusion proteins are indicated. Levels of β-galactosidase activity are measured in yeast cells co-transformed with the two plasmids, a GAL4 BD fusion protein and a GAL4 AD fusion protein. As can be noted the first 71 amino acids of the E1 N-terminus in the BD hybrid molecule, have been removed to circumvent transcription of the Lac Z reporter gene due to the presence of an activation domain within this E1 amino acid region.

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972,11:1726–1732).

The present description refers to a number of routinely used recombinant DNA (rDNA) technology terms. Nevertheless, definitions of selected examples of such rDNA terms are provided for clarity and consistency.

The term "recombinant DNA" or "recombinant plasmid" as known in the art refers to a DNA molecule resulting from the joining of DNA segments. This is often referred to as genetic engineering.

The term "DNA segment or molecule or sequence", is used herein, to refer to molecules comprised of the deoxyribonucleotides adenine (A), guanine (G), thymine (T) and/or cytosine (C). These segments, molecules or sequences can be found in nature or synthetically derived. When read in accordance with the genetic code, these sequences can encode a linear stretch or sequence of amino acids which can be referred to as a polypeptide, protein, protein fragment and the like.

As used herein, the term "gene" is well known in the art and relates to a nucleic acid sequence defining a single protein or polypeptide. The polypeptide can be encoded by a full-length sequence or any portion of the coding sequence, so long as the functional activity of the protein is retained.

A "structural gene" defines a DNA sequence which is transcribed into RNA and translated into a protein having a specific amino acid sequence thereby giving rise to a specific polypeptide or protein.

"Restriction endonuclease or restriction enzyme" is an enzyme that has the capacity to recognize a specific base sequence (usually 4, 5 or 6 base pair in length) in a DNA molecule, and to cleave the DNA molecule at every place where this sequence appears. An example of such an enzyme is EcoRI, which recognizes the base sequence GAATTC/CTTAAG and cleaves a DNA molecule at this recognition site.

"Restriction fragments" are DNA molecules produced by the digestion of DNA with a restriction endonuclease. Any given genome or DNA segment can be digested by a particular restriction endonuclease into at least two discrete molecules or restriction fragments.

"Agarose gel electrophoresis" is an analytical method for fractionating double-stranded DNA molecules on the basis of size. The method is based on that DNA molecules migrate through a gel as through a sieve, whereby the smallest DNA molecule has the greatest mobility and travels the farthest through the gel. The sieving characteristics of the gel retards the largest DNA molecules such that, these have the least mobility. The fractionated DNA can be visualized by staining the gel using methods well known in the art, nucleic acid hybridization or by tagging the fractionated DNA molecules with a detectable label. All these methods are well known in the art, specific methods can be found in Ausubel et al. (supra).

"Oligonucleotide" is a molecule comprised of two or more deoxyribonucleotides or ribonucleotides, preferably more than three. The exact size of the molecule will depend on many factors, which in turn depend on the ultimate function or use of the oligonucleotide. An oligonucleotide can be derived synthetically, by cloning or by amplification.

"Sequence amplification" is a method for generating large amounts of a target sequence. In general, one or more amplification primers are annealed to a nucleic acid sequence. Using appropriate enzymes, sequences found adjacent to, or in between the primers are amplified. An amplification method used herein is the polymerase chain reaction (PCR).

"Amplification primer" refers to an oligonucleotide, capable of annealing to a DNA region adjacent to a target sequence and serving as the initiation primer for DNA synthesis under suitable conditions well known in the art. The synthesized primer extension product is complementary to the target sequence.

The term "domain" or "region" refers to a specific amino acid sequence that defines either a specific function or structure within a protein. As an example herein, is the oligomerization domain of this invention that is comprised within the papillomavirus E1 protein.

The term "delineated" as used herein means a protein or peptide segment that is comprised between the amino acids referred to excluding the delineating amino acids. For example, a protein delineated by amino acids 30 to 100 refers to any protein or peptide segment of any length that would be located between amino acid 33 (exclusively) and amino acid 100 (exclusively) or any variant, derivative or fragment thereof.

The term "delimited" as used herein means a protein or peptide segment that is consisting of amino acids referred to including the delimiting amino acids. For example, a protein delimited by amino acids 31 to 99 refers to a protein or peptide fragment comprising amino acids 33 to 99 or any variant or derivative thereof.

The term "fusion protein" as defined herein refers to at least two polypeptidic segments that are not joined together in nature. Non-limiting examples of such "fusion proteins" according to the present invention include the E1 protein and any variant, fragment or variant thereof, fused to thioredoxin. For the purpose of this invention, the use of thioredoxin enables the fused E1 protein or any fragment, variant or derivative thereof to be purified in a soluble form. Therefore any protein capable of solubilizing E1 protein may be used for the purpose of this invention. Another example of fusion proteins for the purpose of the present invention is the fusion of E1 protein and any variant, derivative or fragment thereof to the GAL4 protein. These fused polypeptides may be further fused to a polypeptide of an "affinity label". In some embodiments it may be beneficial to introduce additional cleavage site between the two polypeptide sequences which have been fused. Such cleavage sites between two or more heterologously fused protein are well known in the art.

The terms "vector" or "DNA construct" are commonly known in the art and refer to any genetic element, including, but not limited to, plasmid DNA, phage DNA, viral DNA and the like which can incorporate the oligonucleotide sequences, or sequences of the present invention and serve as DNA vehicle into which DNA of the present invention can be cloned. Numerous types of vectors exist and are well known in the art.

The term "expression" defines the process by which a structural gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

By "eukaryotic expression system" is meant the combination of an appropriate expression vector and a eukaryotic cell line which can be used to express a protein of interest. In some systems the gene for the protein may be inserted into the genome of a virus which can infect the cell type being used. Plasmid vectors containing the desired gene may also be used. In all cases, the vector will contain appropriate control elements (promoter) to express protein in the cell type of interest. Additional components, for example a vector or viral genome coding for T7 polymerase, may also be necessary in certain expression systems. Eukaryotic cell types typically used are yeast (e.g. *Saccharomyces cerevisiae, Pischia pastoris*) transfected with a plasmid vector; insect cells (e.g. SF9, SF21) infected with baculovirus (Autographa californica or Bombyx mori) (Luckow, Curr. Op. Biotech., 1993, 4:564–572; Griffiths and Page, 1994, Methods in Molec. biol. 75:427–440; and Merrington et al., 1997, Molec. Biotech. 8(3):283–297); mammalian cells infected with adenovirus, vaccinia virus, Sindbis virus, or semliki forest virus; and mammalian cells transfected with DNA vectors for transient or constitutive expression. Particularly preferred here is the yeast Saccharomyces cerevisiae system and the mammalian cells from Chinese Hamster ovary (CHO) cells.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting/transforming DNA may be maintained on an episomal element such as a plasmid. With respect to eukaryotic cells, an example of a stably transfected cell is one in which the transfected DNA has become integrated into a chromosome and is inherited by daughter cells through chromosome replication. This stability is demonstrated by the ability of the eukaryotic cell to establish cell lines or clones comprised of a population of daughter cells containing the transfected DNA. Transfection methods are well known in the art (Sambrook et al., 1989, supra; Ausubel et al., 1994, supra).

The term "affinity label" or "affinity tag" as used herein refers to a label which is specifically trapped by a complementary ligand. Examples of pairs of affinity marker/affinity ligand include but are not limited to: Maltose-Binding Protein (MBP)/maltose; Glutathione S Transferase (GST)/ glutathione; poly-histidine (His)/metal. The metal used as affinity ligand may be selected from the group consisting of: cobalt, zinc, copper, iron, and nickel (Wong et al., 1991, Separation and Purification Methods, 20(1), 49–106). Preferably, the metal selected is nickel. The affinity ligand can be set up in columns to facilitate separation by affinity chromatography.

The affinity label may be positioned on the N- or C-terminal end of the protein, but preferably on the N-terminus of the protein.

The nucleotide sequences and polypeptides useful to practice the invention include without being limited thereto, mutants, homologs, subtypes, alleles, and the like. It shall be understood that generally, the sequences of the present invention encode an interaction domain. It will be clear to a person skilled in the art that the interaction domain of the present invention and any variant, derivative or fragment thereof, can be readily determined by using the teachings and assays of the present invention and the general art.

As used herein, the designation "variant" denotes in the context of this invention a sequence whether a nucleic acid or amino acid, a molecule that retains a biological activity (either functional or structural) that is substantially similar to that of the original sequence. This variant or equivalent may be from the same or different species and may be a natural variant or be prepared synthetically. Such variants include amino acid sequences having substitutions, deletions, or additions of one or more amino acids, provided that the biological activity of the protein is conserved. The same applies to variants of nucleic acid sequences which can have substitutions, deletions, or additions of one or more nucleotides, provided that the biological activity of the sequence or its translated protein is generally maintained.

The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects. Furthermore, these moieties can be used for the purpose of labeling, binding, or they may be comprised in fusion product(s). Different moieties capable of mediating the above described effects can be found in Remington's The Science and Practice of Pharmacy (1995). Methodologies for coupling such moieties to a molecule are well known in the art.

The term "fragment" refers to any segment of an identified DNA, RNA or amino acid sequence and/or any segment of any of the variants or derivatives described herein above.

The terms "variant", "derivative", and "fragment" of the present invention refer herein to proteins or nucleic acid molecules which can be isolated/purified, synthesized chemically or produced through recombinant DNA technology. All these methods are well known in the art.

As exemplified herein below, the nucleotide sequences and polypeptides used in the present invention can be modified, for example by in vitro mutagenesis, to dissect the catalytic and structure-function relationship thereof and permit a better design and identification of the resulting proteins.

"Oligomerization" refers to an interaction between at least two molecules. The molecules may be the same or different. In the present invention the term self-oligomerization refers to the interaction between the E1 protein and any derivative, variant or fragment thereof.

"Screening sequence", is defined herein as an amino acid sequence that is capable of oligomerizing to itself or to a PV E1 protein (including a derivative, fragment or variant, thereof). This sequence comprises a component of a screening method for selecting agents that modulate oligomerization.

"DNA co-immunoprecipitation assay", is an assay for the detection of protein-DNA interaction. The protein-DNA complex is immunoprecipitated with an antibody against the protein comprised in the complex. The immunoprecipitated product comprising the DNA, may be detected/measured or visualized by methods well known in the art. such as agarose gel electrophoresis followed by radio imaging or colorimetric techniques.

Preferred Embodiments

In a particularly preferred embodiment there is provided an amino acid sequence and any derivative, variant or fragment thereof, comprised within the PV E1 protein region A necessary for E1 oligomerization.

Oligomerization of E1 protein is demonstrated in this application by using various sized amino acid fragments of the E1 protein region A. These fragments are all within the scope of the present invention.

In accordance with this first embodiment, there is provided an amino acid sequence necessary for the oligomerization of PV E1 protein delineated by amino acids 352 and 439 as numbered according to HPV-11. Alternatively, the amino acid sequence is delimited by amino acids 353 to 438 according to HPV-11 numbering. Still, alternatively, the amino acid sequence is defined according to SEQ ID No. 2.

In a preferred aspect of this first embodiment, the amino acid sequence is further delineated by amino acids 352 and 432. Alternatively, the amino acid sequence is delimited by amino acids 353 to 431 according to HPV-11 numbering. Still, alternatively, the amino acid sequence is defined according to SEQ ID No. 3.

In a more particular aspect of this first embodiment the amino acid sequence is further delineated by amino acids 352 and 417. Alternatively, the amino acid sequence is delimited by amino acids 353 to 416 according to HPV-11 numbering. Still, alternatively, the amino acid sequence is defined according to SEQ ID No. 4.

In accordance with the above stated embodiment of the amino acid sequences, all variants, derivatives and fragments thereof being functionally equivalent to the sequences herein are within the scope of this invention.

It is an additional embodiment of this invention, that the amino acid sequences of this invention can self- associate. Further these sequences are capable of forming oligomers with the full length E1 protein and any derivative, variant or fragment thereof, comprising the sequence of this invention.

Therefore, in accordance with a second embodiment of this invention there is provided a screening assay for assessing the E1/DNA binding (hence oligomerization of E1 protein) by detecting and/or measuring the amount of DNA co-precipitated with the E1 protein.

According to a specific aspect of this second embodiment, there is provided an assay for screening an agent capable of inhibiting E1 oligomerization by measuring the decrease in DNA co-immunoprecipitated with the E1 protein.

More particularly, this second embodiment provides an oligomerization assay comprising the steps of:

a. combining E1 protein with a DNA fragment, and incubating for a period of time to allow the E1 protein and the DNA to form a complex, b. isolating the E1 protein/DNA complex from the non-complexed DNA, c. detecting the DNA, wherein the presence of DNA is an indication of E1 protein binding to DNA, and thereby correlates with E1 oligomerization.

The E1 used for this assay may be selected from: the amino acids sequences of this invention, the full length E1 protein, N-terminally truncated E1 protein (e1*) and any derivative, variant or fragment thereof.

Preferably, the DNA fragment used in this particular embodiment contains an origin of replication to enhance the specificity of the E1 binding. More preferably, the E1 is combined with a mixture of two DNA fragments, one of which containing an origin of replication and the second one consisting of a different length DNA such that it is distinguishable from the ori-containing DNA and that the amount of E1 bound to the ori-containing DNA may be compared to the amount of non-specific binding.

Particularly, the E1-DNA complex is isolated from the free DNA by column chromatography, centrifugation, extraction, filtration, or immunoprecipitation. More preferably, the E1-DNA is isolated by immobilizing the antibody to a solid medium such as an SPA bead or the bottom of a well from a testing plate such that when the medium is removed, so is the free DNA.

Particularly, E1 is immunoprecipitated or immobilized using a polyclonal antibody. More particularly, the polyclonal antibody is K71 or K72.

Preferably, before the complexed DNA is detected, the DNA is released from the E1/DNA complex. Such release may be carried out, for example, by organic extraction.

In a specific aspect of this second embodiment, the DNA can be detected by methods including gel electrophoresis, spectrophotometry and radioactive imaging. Accordingly, depending on the detection means chosen, the DNA is labeled by any appropriate means known in the art, including fluorescent dyes or radioactive isotopes. Preferably, the DNA is radiolabeled and detected by gel electrophoresis followed by radioactive imaging. Alternatively, the DNA is labeled with a calorimetric dye and detected spectrophotometrically, or the DNA is labeled with a fluorescent dye and detected by scintillation proximity technology (SPA).

Particularly, the DNA is labeled prior to complex formation, after immunoprecipitation or after the DNA is released from the immunoprecipitation complex.

In a particular aspect of this second embodiment, there is provided the assay as described above adapted for screening for an agent capable of inhibiting E1-oligomerization, this assay further comprising the steps of:
  a. contacting an agent to the E1 protein prior to combining with the DNA fragment and incubating for a period of time to allow E1 protein/DNA to form a complex, and
  e. comparing the results with a control sample, wherein the control sample is similarly treated but without the addition of said agent.

More particularly, such a selected agent is capable of interfering with the oligomerization and moist particularly such an agent is inhibitory to the oligomerization of E1 protein and any derivative, variant or fragment thereof as described above.

In accordance with the third embodiment of this invention, there is provided a cross-linking assay to directly measure the level of oligomerization (or inhibition thereof) of the E1 protein. Particularly, this oligomerization assay comprises the steps of:
  a. combining labeled-E1 protein with a DNA fragment and incubating for a period of time sufficient to allow the E1 protein and the DNA to form a complex,
  b. cross-linking the E1 protein and the DNA in the complex with a cross-linking agent,
  c. separating the E1 protein electrophoretically such that the migration of E1 is an indication of the level of oligomerization of E1.

Preferably, the E1/DNA complex is isolated from the free DNA before carying out the separation.

Particularly, the E1 protein used in this oligomerization assay is a N-terminally truncated E1 protein. More preferably, it has about its first 70 N-terminal amino acids deleted. More preferably, this E1 protein is delimited by amino acid 72–649.

Preferably, the E1 protein is labeled with a radioisotope. More preferably, it is labeled with $^{35}S$ and is detected on the gel by radio-imaging techniques well known in the art.

Preferably, the cross-linking agent is bismaleimidohexane (BMH).

In accordance with a fourth embodiment of this invention, there is provided a N-terminally truncated E1 protein. Particularly, the first about 70 N-terminal amino acids are deleted from the e1 protein. More particularly, one aspect of this fourth embodiment encompasses the E1 protein delimited by amino acid 72 to 649 (SEQ ID No. 78).

Since it has been shown that the E1 protein has similarities with other papilloma viruses and with SV40 and polyoma virus T antigens, the invention encompasses any amino acid sequences necessary for the oligomerization of a protein that is required to initiate viral DNA replication, having functional and/or structural similarities to the amino acid sequence of the present invention.

In an additional preferred embodiment of this invention, a region in the E1 protein necessary for oligomerization having similar function and/or structure is present in bovine papilloma virus, cottontail papilloma virus or human papilloma virus. In a specific aspect of the embodiments of this invention, the PV DNA is from HPV.

In a more preferred embodiment the region of the E1 protein is selected from HPV low risk or high risk type; High risk types consisting of types 16, 18, 31, 35, 45, 52 and 52. ; and low risk types consisting of types 6, 11 and 13.

In a most preferred embodiment of this invention, the amino acid sequence of this invention is from a low risk human papilloma virus type 11.

In a specific aspect of the embodiments of this invention, the E1 protein can be obtained by different means. In a non-limiting example the protein is synthesized by coupled transcription/translation in a rabbit reticulocyte lysate or is made by recombinant technology.

In accordance with an application of this invention, the screening method and screening system are conducted at low temperatures in the presence or absence of ATP/Mg or at high temperatures in the presence of ATP/Mg. More preferably, at low temperatures of about 4° and 23°, and at a high temperature of about 37°. Further, the E1 protein may be made by in-vitro transcription/translation, or recombinant technology and comprises amino acids 72–649 (SEQ ID NO. 78), however other means known in the art can be used to provide the amino acid sequence for screening.

In an application of this invention the amino acid sequence of this invention and any variant, derivative or fragment thereof, can be used in an affinity column for the selection of any protein or molecule capable of binding to it. Non-limiting examples are antibodies, polypeptides, nucleic acid sequences and chemical compounds.

Preferably, the agent selected using the embodiments of this invention affects viral DNA replication, specifically papillomavirus DNA replication and more particularly HPV. In a particular application of this invention it is contemplated that one or more of the selected agent/s can be used in a pharmaceutical composition for the treatment of papilloma virus infection.

Though specific technical means are exemplified herein, any means known to a person skilled in the art for the purpose of this invention is contemplated to be under the scope of this invention.

EXAMPLES

Example 1

Yeast Strain, Media, and Genetic Methods

*Saccharomyces cerevisiae* strain Y153 (MATa leu2-3, 112 ura3-52 trp1-901 his3-Δ200 ade2-101 gal4Δgal80Δ URA3:: GAL-lacZ LYS::GAL-HIS3) was used for yeast two-hybrid analysis (Durfee et al., 1993, Genes. Dev. 7:555–569). Transformation of yeast strain Y153 was performed using the LiAc method essentially as described in the Clontech *Matchmaker Library Protocol*. Cells that were co-transformed with a combination of two plasmids were selected at 30° C. for 3 to 5 days on SD medium (described by Sherman et al. 1979, Methods in Yeast Genetics, Cold Spring Harbor, N.Y.) lacking leucine and tryptophan but supplemented with the other required amino acids.

Example 2

β-Galactosidase Assays

Transformed yeast cells were pre-grown in liquid SD medium lacking leucine and tryptophan and then used to inoculate YPD (Sherman et al. Supra) cultures. These cultures were grown at 30° C. until they reached an optical density of approximately 0.6 at 600 nm ($OD_{600}$). Cells were then harvested, washed and permeabilized by two cycles of freezing (liquid nitrogen) and thawing. β-galactosidase activity was then measured spectrophotometrically (at 578 nm) using the substrate chlorophenyl-red-β-D-galactopyranoside (CRPG, Boehringer Mannheim) as described in the Clontech *Matchmaker Library Protocol*.

Enzymatic activity was calculated using the equation: Miller unit=$(1000 \times OD_{578})/$(elapsed min$\times 1.5$ ml culture$\times OD_{600})$.

Example 3

Plasmid Constructions

A. Plasmids for In-vitro Transcription/translation

The constructs and the primers for amplification are summarized in Table 1.

Plasmids used for synthesis of HPV-11 E1 and E2 in vitro were derived either from pCR3 (Invitrogen, CA) or from pTM1 (obtained from Bernard Moss, NIH). In these plasmids, the encoded protein can be expressed in vitro from the T7 promoter located upstream of the open reading frame (ORF). When used in a coupled transcription/translation system (TNT Coupled Reticulocyte Lysate System, Promega), plasmids derived from pTM1 directed the synthesis of higher levels of proteins. Presumably, it is because this plasmid encodes the EMCV IRES (encephalomyocarditis virus internal ribosome entry site), which stimulates translation (data not shown).

To construct pCR-E1 and pCR-E2, the entire HPV-11 E1 and E2 ORFs were amplified separately by polymerase chain reaction (PCR), though any method capable of amplifying DNA is suitable for the purpose of this invention. The following pairs of oligonucleotides were used in the amplification reaction:

E1:    CAAGG<u>ATG</u>GCGGACGATTCA,    (SEQ ID NO. 15)
and
        TCT<u>TCA</u>TAAAGTTCTAACAAC    (SEQ ID NO. 16)

E2:    GAAG<u>ATG</u>GAAGCAATAGCCAA,    (SEQ ID NO. 17)
and
        ATGG<u>TTA</u>CAATAAATGTAATGAC    (SEQ ID NO. 18)

(The ATG and Stop codons of E1 and E2 are underlined)

The DNA templates used for PCR were baculovirus construct Ac11E1 or Ac11E2 (obtained from R. Rose, U. of Rochester). The E1 and E2 PCR products were each cloned under the control of the cytomegalovirus immediate-early promoter in plasmid pCR3, using the TA cloning kit (Invitrogen), to generate pCR-E1 and pCR-E2.

Plasmid pCR-FLAG-E1 (FLAG epitope is from Eastman Kodak Co.) which expresses E1 (amino acids 2–649) fused at its N-terminus to the FLAG epitope (Met Asp Tyr Lys Asp Asp Asp Asp Lys) was constructed by PCR amplification of the E1 ORF with the following two oligonucleotides:

CATGG<u>ACTACAAGGACGACGATGACAAG</u>GCGGACGATTCAGGTACAGAAAAT, (SEQ ID NO. 19)
and

GGGATCCTTATTATAAAGTTCTAACAACTGATCCTGGCAC    (SEQ ID NO. 20)

(the portion encoding the FLAG epitope is underlined). The resulting PCR product was cloned into plasmid pCR3 (Invitrogen) using the TA cloning kit (Invitrogen).

To construct plasmid pTM1-E1, the E1 ORF was amplified by PCR using the following two oligonucleotides:

(SEQ ID NO. 21)
GTACGATCCCATGGCGGACGATTCAGGTACAGAAAAT, and (SEQ ID NO. 22)
GTACGATGGGATCCTTATTATAAAGTTCTAACAACTGATCCTGGCAC The resulting PCR product was digested with the restriction enzymes NcoI and BamHl (the restriction sites are encoded by the two oligonucleotides) and inserted between the NcoI and BamHl sites of plasmid pTM1.

Plasmid pTM1-FLAG-E1 which expresses E1 (amino acids 2–649) fused at its N-terminus to the FLAG epitope (Met Asp Tyr Lys Asp Asp Asp Asp Lys) was constructed by PCR amplification of the E1 ORF with the following two oligonucleotides:

CCCATGG<u>ACTACAAGGACGACGATGACAAG</u>GCGGACGATTCAGGTACAGAAAAT,(SEQ ID NO. 23)
and

GGGATCCTTATTATAAAGTTCTAACAACTGATCCTGGCAC    (SEQ ID NO. 24)

(the portion encoding the FLAG epitope is underlined). The resulting PCR product was digested with NcoI and BamHl (encoded by the two oligonucleotides) and inserted between the NcoI and BamHl sites of plasmid pTM1.

Plasmids to express N-terminally truncated E1 proteins in vitro were constructed by amplification of the desired portion of the E1 ORF with specific primers bearing an NcoI site (forward primer) and a BamHl site (reverse primer). PCR products were digested with NcoI and BamHl and inserted between the NcoI and BamHl sites of plasmids pTM1. The sequences of the different E1 forward primers that were used, and that of the common reverse primer, are described below. Indicated in brackets is the first amino acid of E1 that is encoded by each of these oligonucleotides.

Forward primers:

(SEQ ID NO. 25)
CCGGGATCCTAATGGCGGACGATTCAGGT    (a.a. 1)

(SEQ ID NO. 26)
GGCTGGATCCATGGCGGATGCTCATTATGCG    (a.a. 72)

(SEQ ID NO.27)
GGCTGGATCCATGGCCATTAAACTTACAACACAG    (a.a. 112)

(SEQ ID NO.28)

```
                                                  -continued
GGCTGGATCCATGGGCTATTCTGAAGTGGAAG                     (a.a. 138)

(SEQ ID NO.29)
GGCTGGATCCATGGGGAGGGACATAGAGGGT                      (a.a. 166)

(SEQ ID NO.30)
GGCTGGATCCATGGACACATCAGGAATATTAGAA                   (a.a. 191)

(SEQ ID NO.31)
GGCTGGATCCATGGACAGTCAATTTAAATTAACT                   (a.a. 353)

(SEQ ID NO. 32)
GGCTGGATCCATGGACAGTGTAGGTAACTGG                      (a.a. 435)
```

Reverse primer:
CCCGGATCCTCATAAAGTTCTAACAACT (a.a. 649) (SEQ ID NO.33)

Plasmid pTM1-FLAG-E1(72–649) which encodes a truncated HPV-11 E1 protein that lacks the N-terminal 71 amino acids, but which is tagged at its N-terminus with the FLAG epitope, was constructed by PCR amplification using an oligonucleotide which encodes the FLAG-epitope: GGGGGCCATGGACTACAAGGACGACGAC-GACAAGGCGGATGCTCATT ATGACTG (SEQ ID NO.34) (the sequence of the FLAG epitope is underlined) and the following reverse primer was used: CCCGGATCCTCATAAAGTTCTAACAACT (SEQ ID NO.33)

Plasmids similar to pTM1-FLAG-E1 (72–649) but which encode E1 proteins with a truncated C-terminus were constructed by PCR amplification of the desired portion of the E1 ORF with specific primers bearing an NcoI site (forward primer) and a BamHI site (reverse primer). PCR products were digested with NcoI and BamHI and inserted, in-frame, between the NcoI and BamHI sites of plasmids pTM1. The sequence of the common E1 forward primer (encoding the FLAG epitope) is described below. Also described are the sequences of the different E1 reverse primers that were used. Indicated in brackets is the last amino acid of E1 that is encoded by each of these reverse primers.

Forward primer:

al., 1993, Genes. Dev 7:555–569). Two hybrid plasmids encoding the complete E1 protein (amino acids 1–649) were constructed in a similar way with the exception that the forward primer contained a BamHI site instead of a NcoI site. In this case the PCR product was cut with BamHI and inserted, in frame, into the BamHI sites of pAS1 and pACT2. Two-hybrid plasmids carrying a mutated E1 ORF (P479S, K484E or K484Q) were generated in a similar way but using a mutated E1 gene as a template for PCR (see below for description of E1 mutations). The various forward and reverse primers that were used are described below.

Forward primers:

```
                                                  (SEQ ID NO. 25)
CCCGGATCCTAATGGCGGACGATTCAGGT                        (a.a. 1)

(SEQ ID NO. 26)
GGCTGGATCCATGGCGGATGCTCATTATGCG                      (a.a. 72)

(SEQ ID NO. 28)
GGCTGGATCCATGGGCTATTCTGAAGTGGAAG                     (a.a. 138)

(SEQ ID NO. 30)
GGCTGGATCCATGGACACATCAGGAATATTAGAA                   (a.a. 191)

(SEQ ID NO. 31)
GCTGGATCCATGGCAAGTACAGTTATAGGGG                      (a.a. 330)

(SEQ ID NO. 40)
GGCTGGATCCATGGACAGTCAATTTAAATTAACT                   (a.a. 353)

(SEQ ID NO. 41)
GGCTGGATCCATGGCATATGATAATGATATTTGTG                  (a.a. 365)

(SEQ ID NO. 42)
GGCTGGATCCATGGCATTTGAATATGCACAGCG                    (a.a. 377)

(SEQ ID NO. 43)
GGCTGGATCCATGGGAGACTTTGACTCCAATGC                    (a.a. 384)

(SEQ ID NO. 44)
GGCTGGATCCATGGACTCCAATGCAAGGGCC                      (a.a. 387)

(SEQ ID NO. 45)
GGCTGGATCCATGGATTGTGCAATTATGTGCAG                    (a.a. 405)
```

```
Forward primers:
GGGGGCCATGGACTACAAGGACGACGACGACAAGGCGGATGCTCATTATGACTG       (SEQ ID NO. 34)
(the sequence of the FLAG epitope is underlined)

Reverse primers:
CCCGGATCCTCATAAAGTTCTAACAACT                                 (SEQ ID NO. 33)

CCCGGATCCTCATGCATCTGATAGTTCATATACTG            (a.a. 608)    (SEQ ID NO.35)

CCCGGATCCTCAGCTAATGTCTATATTTGATGTAACC          (a.a. 572)    (SEQ ID NO.36)

CCCGGATCCTCATAAAAATGGAATAAATTCTATGTTTTGATG     (a.a. 458)    (SEQ ID NO. 37)

CCCGGATCCTCACTGGCGCGTTATCCATTCCGGC             (a.a. 344)    (SEQ ID NO. 38)

CCCGGATCCTCAAATGCCTGTCCTAAACCAATAC             (a.a. 327)    (SEQ ID NO. 39)
```

B. Yeast Two-hybrid Plasmids.

The constructs and the primers used for amplification are summarized in Tables 2 and 3.

Unless described otherwise, HPV-11 E1 DNA fragments were amplified by PCR with specific primers bearing an NcoI site (forward primer) and a BamHI site (reverse primer). PCR products were digested with NcoI and BamHI and inserted, in-frame, between the NcoI and BamHI sites of the yeast two-hybrid vectors pAS1 (GAL4 DNA-binding domain) and pACT2 (GAL4 activation domain) (Durfee et

```
                                                  -continued (SEQ ID NO. 46)
GGCTGGATCCATGGCAGAAATGAAAAAGATGTC                    (a.a. 416)

(SEQ ID NO. 32)
GGCTGGATCCATGGACAGTGTAGGTAACTGG                      (a.a. 435)
```

Reverse primers:

| | | |
|---|---|---|
| CCCGGATCCTCATAAAGTTCTAACAACT | (a.a. 649) | (SEQ ID NO. 33) |
| CCCGGATCCTCAGCTAATGTCTATATTTGATGTAACC | (a.a. 572) | (SEQ ID NO. 36) |
| CCCGGATCCTCAATATGTATCCATATATGTCCA AC | (a.a. 536) | (SEQ ID NO. 32) |
| CCCGGATCCTCATAAAAATGGAATAAATTCTATGTTTTGATG | (a.a. 458) | (SEQ ID NO. 47) |
| CCCGGATCCTATCACACAATTGGCTTCCAGTTACC | (a.a. 444) | (SEQ ID NO. 48) |
| CCCGGATCCTATCAACCTACACTGTCAACTTTAG | (a.a. 438) | (SEQ ID NO. 49) |
| CCCGGATCCTATCAACCCCTATACTTAATCCATTG | (a.a. 431) | (SEQ ID NO. 50) |
| CCCGGATCCTATCATGCATGTTTATAATGTCTGCAC | (a.a. 416) | (SEQ ID NO. 51) |

Using a different approach pAS1- and pACT2-derived plasmids encoding E1 sequences 353–572, 353–536 and 353–458 were constructed in two steps. In the first step, E1 sequences were amplified by PCR using the following two primers:

| | | |
|---|---|---|
| GGCTGGATCCATGGACAGTCAATTTAAATTAACT | (SEQ ID NO. 40) (a.a. 353) | |
| and, | | |
| CCCGGATCCAGTGTGATGGATATCTGCAG | (SEQ ID NO. 52) (pCR3). | |

The templates for PCR were pCR3-derived plasmids expressing a truncated E1 ORF: either E1 amino acids 1–572, 1–536, or 1–458. One of the two oligonucleotides used for PCR amplification hybridizes over codon 353 of E1. The other oligonucleotide hybridizes in the polylinker region of pCR3, downstream of the truncated E1 ORF. The PCR products were digested with NcoI and BamHI and cloned between the NcoI and BamHI sites of pAS1 and pACT2. The plasmids that were used as templates in these three PCR reactions were constructed by amplification of the E1 ORF with the following oligonucleotide: CAAGGATGGCGGACGATTCA (SEQ ID NO. 15) (ATG of E1 is underlined) and one of three oligonucleotides that hybridizes over codon 572, 536 and 458, respectively, of E1. The sequences of these oligonucleotides are given below:

| | | |
|---|---|---|
| GGATCCTCATTAGCTAATGTCTATATTTGATGT | (SEQ ID NO. 53) (a.a. 572) | |
| GGATCCTCATTAATATGTATCCATATA | (SEQ ID NO. 54) (a.a. 536) | |
| GGATCCTCATTATAAAAATGGAATAAATTCTATG | (SEQ ID NO. 55) (a.a. 458) | |

The resulting PCR products were cloned into pCR3, using the TA cloning kit (Invitrogen).

C. Plasmids for Transient HPV Replication.

Plasmids that were used in transient HPV DNA replication assays to express E1 and E2 in transfected cells were all derived from pCR3: pCR-E1, pCR-FLAG-E1 (wt and mutant E1) and pCR-E2. These plasmids are described above.

Plasmid pN9 (Lu et al., 1993, J. of Virol. 67: 7131–7139) was obtained from D. McCance (U. of Rochester) and contains the complete origin of replication of HPV-11 (nucleotides 7884 to 61) cloned into pBluescriptII SK+ (Stratagene).

D. Plasmids for Expression of Thioredoxin Fusion Proteins

Three fragments of E1 (a.a. 353–416/353–431/353–438) were expressed in *E. coli* as fusion proteins with thioredoxin (TRX). Plasmids to express these fusion proteins were constructed by PCR amplification of the relevant portion of the E1 ORF using a subset of the forward and reverse oligonucleotides described above. PCR products were digested with NcoI and BamHI and subcloned between the NcoI and BamHI sites of plasmids pET-32a–c(+) (Novagen) which encodes TRX.

Example 4

Site-directed Mutagenesis

Site-directed mutagenesis of E1 was performed with the QuickChange Site-Directed Mutagenesis kit (Stratagene) according to the instructions supplied by the manufacturer. For each mutagenesis, a pair of complementary oligonucleotides was used. For each pair, the sequence of the oligonucleotide corresponding to the sense strand is described below. The resulting amino acid substitution is also indicated.

| | | | |
|---|---|---|---|
| E1 F378A | GTGAGATAGCAGCTGAATATGCACAGCG | (SEQ ID NO. 56) | |
| E1 Y380A | GAGATAGCATTTGAAGCTGCGCAGCGTGGAG | (SEQ ID NO. 57) | |
| E1 N389A | GACTTTGACTCCGCGGCAAGGGCC | (SEQ ID NO. 58) | |
| E1 A390G | GGAGACTTTGACTCCAACGGCCGGGCCTTTTTAAATAG | (SEQ ID NO. 59) | |
| E1 F393A | GCAAGGGCCGGGTTAAATAGTAATATGC | (SEQ ID NO. 60) | |
| E1 Q399A | CCTTTTTAAATAGTAATATGGCGGCTAAATATGTAAAAG | (SEQ ID NO. 61) | |

| | | |
|---|---|---|
| E1 P479S | CCATTGTAGGGTCACCTGACACTGG | (SEQ ID NO. 62) |
| E1 K484E | CTGACACTGGGGAGTCGTGCTTTTG | (SEQ ID NO. 63) |
| E1 K484Q | CTGACACTGGGCAGTCGTGCTTTTG | (SEQ ID NO. 64) |
| E1 K484H | CCTGACACTGGGCACTCGTGCTTTTGC | (SEQ ID NO. 65) |
| E1 K484I | CCTGACACTGGGATCTCGTGCTTTTGC | (SEQ ID NO. 66) |
| E1 K484R | CCTGACACTGGGCGGTCGTGCTTTTGC | (SEQ ID NO. 67) |
| E1 F509A | CCTGCAGCCACGCGTGGCTACAGCC | (SEQ ID NO. 68) |
| E1 T566A | CCGCTACTGGTTGCTAGCAATATAGACATTAGC | (SEQ ID NO. 69) |
| E1 N568A | CTACTGGTTACATCAGCAATTGACATTAGCAAAG | (SEQ ID NO. 70) |
| E1 K286A/R288A | GGTTTAAAGTAAATGCTAGCGCATGTACCGTGGCACG | (SEQ ID NO. 71) |
| E1 A292L/R293E | CAGATGTACCGTGCTCGAGACATTAGGTACG | (SEQ ID NO. 72) |

The triple point mutation in the HPV-11 origin was introduced into plasmid pN9 using the following oligonucleotide: CATATTTCCTTCTTATACTGCAGAA-CAATCTTAGTTTAAAAAAGAGG (SEQ ID NO. 73) and its complementary one (the mutant nucleotides are underlined).

Example 5

E1-origin Binding Assay

The TNT Coupled Reticulocyte Lysate System (Promega) was used to produce the E1 protein by coupled transcription/translation in vitro. The lysate was programmed with 2 µg of the appropriate plasmid per 50 µl of TNT reticulocyte lysate, and according to the protocol supplied by the manufacturer. When required, the E1 protein was radiolabeled by incorporation of $^{35}$S-methionine. Binding reactions were performed by mixing 30 µl of lysate containing E1, 200 to 400 ng of a $^{33}$P-radiolabeled DNA probe, and 7.5 µl of 10×DNA binding buffer (200 mM Tris-HCl pH 7.6, 1 M NaCl, 10 mM EDTA, 10 mM DTT) in a final volume of 75 µl. Binding reactions were allowed to proceed at the indicated temperature for 90 min. When indicated, ATP (or a related nucleotide) and $MgCl_2$ were supplemented to the binding reactions at a final concentration of 5 mM and 3 mM, respectively. DNA-protein complexes were immunoprecipitated either with the anti-FLAG M2 monoclonal antibody (Eastman Kodak) when using FLAG-tagged E1, or with the K72 polyclonal antibody which was raised in rabbits against a peptide derived from the C-terminal 14 amino acids of HPV11 E1. The amino acid sequence of this peptide is: QAFRCVPGSVVRTL (SEQ ID No. 79). Before use in immunoprecipitation, the antibodies were pre-bound to either protein G sepharose beads (when using anti-FLAG) or protein A sepharose beads (K72). Immunoprecipitation of protein-DNA complexes was carried out for 1 hr at the binding reaction temperature. Complexes were washed 3× with 200 µl of Wash buffer (50 mM Tris pH 7,6; 100 mM NaCl; 0,1% Triton X-100). DNA present in these complexes was extracted with phenol/chloroform and precipitated with ethanol in the presence of carrier yeast tRNA. The precipitated radiolabeled DNA fragments were resolved on a 5% polyacrylamide TBE gel and visualized by autoradiography.

The radiolabeled probe that was used in these experiments consists of two DNA fragments and was prepared in two steps. In the first step, plasmid pN9 was linearized by digestion with XmaI and the ends were labeled with the Klenow fragment of DNA polymerase I in the presence of 5 µCi of $\alpha^{32}$P-dCTP and 0,1 mM of each: dTTP, dATP, dGTP. Labeled DNA was purified on QIAquick PCR purification columns (QIAGEN). In the second step, linear radiolabeled pN9 was digested with PvuII to generate two labeled fragments: a 370 bp fragment which contains the HPV-11 origin of replication and a 186 bp control fragment which lacks the origin.

Example 6

E2-dependent E1 Origin-binding Assay

Conditions for formation of the E1–E2-ori ternary complex were essentially the same as those described above for the E1 origin-binding assay. The only major differences were that 7.5 µl of in-vitro translated E2 protein was added to the binding reaction and that full-length E1 protein (a.a. 1–649) was used in these experiments. Wild type and mutant E1 proteins used in these experiments were produced from plasmids derived from pCR3. Minor modifications included the fact that in-vitro translations were programmed with twice the amount of DNA (2 µg/25 µl reaction) and that only 100 ng of probe was used per assay.

Example 7

Purification of Trx-E1 Fusion Proteins from E. coil

E. coli cells (BL21::DE3 [pLysS]) that contained a plasmid encoding one of three TRX-E1 fusion proteins (see above), or encoding only TRX [pET32a–c(+), Novagen], were grown overnight in LB medium containing ampicillin (100 µg/ml) and chloramphenicol (34 µg/ml). 3 ml of these overnight cultures were diluted 40 fold with fresh medium (120 ml) and incubated at 30° C. until $O.D._{600} \cong 0.5$. Protein expression was then induced with 1 mM IPTG for 3 hours at 30° C. (until cultures reach $O.D._{600} \cong 2.0$). Bacterial cells were harvested by centrifugation at 5000×g for 10 min. Bacterial pellets were resuspended in 1 ml of lysis buffer (60 mM tris pH 7.6; 300 mM NaCl; 10 mM imidazole) and sonicated. The resulting lysates were centrifuged at 16 000×g to get rid of cellular debris and insoluble material. The supernatants were loaded onto pre-equilibrated Ni-NTA spin columns (QIAGEN) and purified according to the manufacturer's protocol for purification of native protein.

Briefly, after loading, each column was washed with 2×600 μl of wash buffer (60 mM tris pH 7.6; 300 mM NaCl; 20 mM imidazole) and the bound proteins were eluted with 2×200 μl of elution buffer (60 mM tris pH 7.6; 300 mM NaCl; 250 mM imidazole). Purified proteins were then analyzed by a 10% SDS-PAGE. All fusion proteins were then diluted with elution buffer to a final concentration of 500 ng/μl.

Example 8

Transient HPV DNA Replication Assay

CHO-K1 (obtained from the American Type Culture Collection) were grown to 40%–60% confluence in 35 mm tissue culture dishes in Ham F12 medium containing 10% fetal bovine serum and gentamicin sulfate. Cells were transfected with 250 ng of pCR-E1 (or pCR-FLAG-E1 mutant), 25 ng of pCR-E2 and 250 ng of pN9 plasmids using lipofectamine (Gibco BRL). The presence of the FLAG epitope at the N-terminus of E1 does not affect its ability to support transient HPV DNA replication (data not shown). Cells were harvested 72 hrs post-transfection and total DNA was isolated using the QIAmp Blood Kit (Qiagen). Replicated pN9 plasmid DNA was detected by PCR amplification of an origin-containing fragment using Dpn1-digested total DNA as a template and the following pair of primers: CTGCAACCGGTTTCGGTTACCCACACCCT (SEQ ID NO. 74) (corresponding to nucleotides 7885–7913 of the HPV-11 genome) and CGTTCCACTGAGCGTAGAC-CCCGTAGAA (SEQ ID NO. 75) (corresponding to nucleotides 1848–1820 of pSK⁺). As a control, a fragment of the pCR-E1 plasmid was amplified in the same PCR reaction with the following pair of primers which hybridize within the E1 ORF: GCTTTGGGCTGTCATTTG (SEQ ID NO. 76) and TGTCAGGTGGCCCTACAA (SEQ ID NO. 77) (corresponding to nucleotides 1475–1492 and 2275–2258, respectively, of the HPV-11 genome). PCR conditions consisted of an initial denaturation step at 95° C. for 1 min, followed by 20 rounds of: denaturation at 94° C. for 30 sec, annealing at 51° C. for 1 min and extension at 72° C. for 1 min 30 sec, ending with a final extension at 72° C. for 3 min. PCR products were made radioactive by the addition of [$\alpha^{33}$P]dCTP to the PCR reactions and were visualized by agarose-gel electrophoresis and autoradiography.

Example 9

E1/DNA Co-immunoprecipitation Assay

1. Binding

In a polypropylene 96-well U-bottom plate, 5 μl of compound (or mixture) at 150 μg/ml in DMSO is added to 60 μl of binding master mix (20 mM Tris pH:7,4; 100 mM NaCl; 5 mM ATP; 3 mM MgCl$_2$; 1 mM EDTA; 1 mM DTT; 5 ng HPV11 ori+probe). Binding reactions starts with the addition of 10 μl of in-vitro translated HPV11 E1 (72–649). The plate is sealed then agitated for 5 min and incubated at 37° C. for 1 h.

2. Immunocapture

Pre-binding of antibodies to protein-A sepharose:

For each assay well, 1 μl of anti-E1 polyclonal antibody is added to 10 μl of 10% protein-A sepharose slurry (20 mM Tris pH 7.0). The slurry is agitated at room temperature for 1 hour. The beads are pelleted by quick centrifugation, washed with 10 μl of 1×binding buffer and then resuspended in 50 μl of 1×binding buffer (+5 mM ATP+1 mM DTT).

Capture:

In a second 96 well U-bottom polypropylene plate, 50 μl of pre-bound K71 or K72 antibody-protein A sepharose is deposited in each well. After binding reaction is complete, the entire binding reaction is transferred to the plate containing the antibody-protein A sepharose beads. The plate is then sealed, incubated at 37° C. and agitated for 1 h.

The anti-E1 polyclonal antibodies used for the purpose of this invention, are referred to herein as K71 and K72. These are antiserum raised in rabbit against a peptide corresponding to the last (C-terminal) 14 a.a. of HPV11 E1.

3. Isolation of Complexes by Filtration

First, a Millipore MHVB N45 96-well filtration plate, is equilibrated by filtering 100 μl 1×binding buffer. Complexes are then transferred, filtered and washed three times with 200 μl 1×binding buffer. Residual liquid is removed by blotting the plate against a paper towel. Finally, 150 μl of MicroScint 20 is added to each well and counts are detected by TopCount using a $^{33}$P protocol.

Results

E1—E1 Interaction in Yeast (FIG. 1)

Figure 1C:
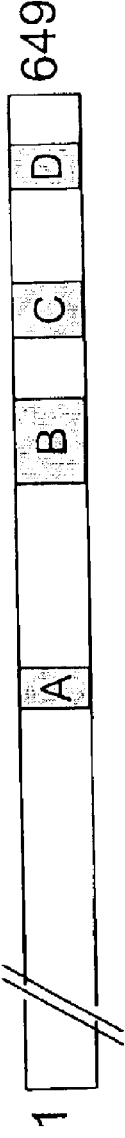
FIG. 1C shows the self-association of E1 fragments in yeast. Three different E1 fragments having N and C-terminal truncations are tested in the yeast two-hybrid system. For comparison, each E1-AD fusion was also tested for interaction with E1 (330–649 of SEQ ID No. 1) fused to the GAL4-BD or with the GAL4-BD alone. The levels of β-galactosidase activity obtained show that the E1 region (amino acid 353–416; SEQ ID No. 4) is sufficient for self-association as well as interacting with a larger E1 protein region (330–649 of SEQ ID No. 1).

The two-hybrid system (Fields and Song, 1989, Nature, 340(6230):245–246 and Durfee, supra) was used to test whether HPV 11 E1 can self-associate in yeast and to map a domain of E1 involved in this interaction (FIG. 1). As can be seen in FIG. 1A a fusion protein consisting of the entire E1 molecule (amino acids 1–649) fused to the DNA-binding domain (BD) of GAL4 is able to activate transcription of the UAS$_{Gal}$-driven LacZ reporter gene in yeast strain Y153. Shorter fusion proteins lacking the N-terminal 71 amino acids of E1 did not activate transcription indicating that the N-terminus of E1 may contain a transcription activation domain. These shorter fusion proteins could be used to test for an interaction with the entire E1 protein fused to the GAL4 activation domain (AD) (FIG. 1A). Interaction of these shorter fusion proteins with the entire E1 molecule gave rise to only low, although reproducibly higher than background, levels of β-galactosidase (FIG. 1A and data not shown) indicating that E1 can self-associate in yeast. A series of deletions was used to map the interaction domain to the C-terminal region of E1 (amino acids 353–649). Self-association of E1 was more readily detectable between fusion proteins containing only the C-terminal portion of E1 (amino acids 330–649 and 353–649) (FIG. 1 B). A series of deletions was used to refine the location of the E1 interaction domain (FIG. 1B). In this way, a 64 amino acids long E1 interaction domain was identified between amino acids 353–416 (FIG. 1B). A C-terminal E1 fragment (amino acids 435–649) that lacked this 64 amino acid domain was unable to associate with E1 (330–649) (FIG. 1B) although it retained the ability to interact with E2. The small E1—E1 interaction domain (353–416) was capable not only of interacting with a larger E1 fragment (330–649) but also with itself (FIG. 1C). This last result indicated that residues 353–416 are necessary and sufficient for homotypic interaction of E1. The interaction of this small domain with E1 (330–649), or with itself, gave rise to lower levels of β-galactosidase activity than interaction between larger E1 fragments (353–649 and 330–649) (FIG. 1C). This result was consistent with the notion that residues between amino acids 435–649, although not sufficient for interaction with E1, can contribute to the strength of the interaction.

Role of the ATP-binding Domain of E1 in Self-association (FIG. 2)

The results presented above raised the possibility that residues 435–649 of E1, which are located C-terminal to the E1—E1 interaction domain (353–416), may also contribute to the strength of the E1—E1 interaction in yeast. Because residues 435–649 encompass the ATP-binding domain of E1, we mutated three highly conserved amino acids involved in ATP-binding and tested the effect of these amino acid substitutions on self-association of E1 in yeast. These substitutions replaced two residues of the Walker A motif (P-loop) of E1: Proline 479 was changed by serine and Lysine 484 was replaced by glutamic acid and glutamine. As can be seen in FIG. 2, all three substitutions reduced E1—E1 interaction in yeast. These results indicate that the integrity of the ATP-binding domain is important for self-association of the E1 protein.

Figure 3:
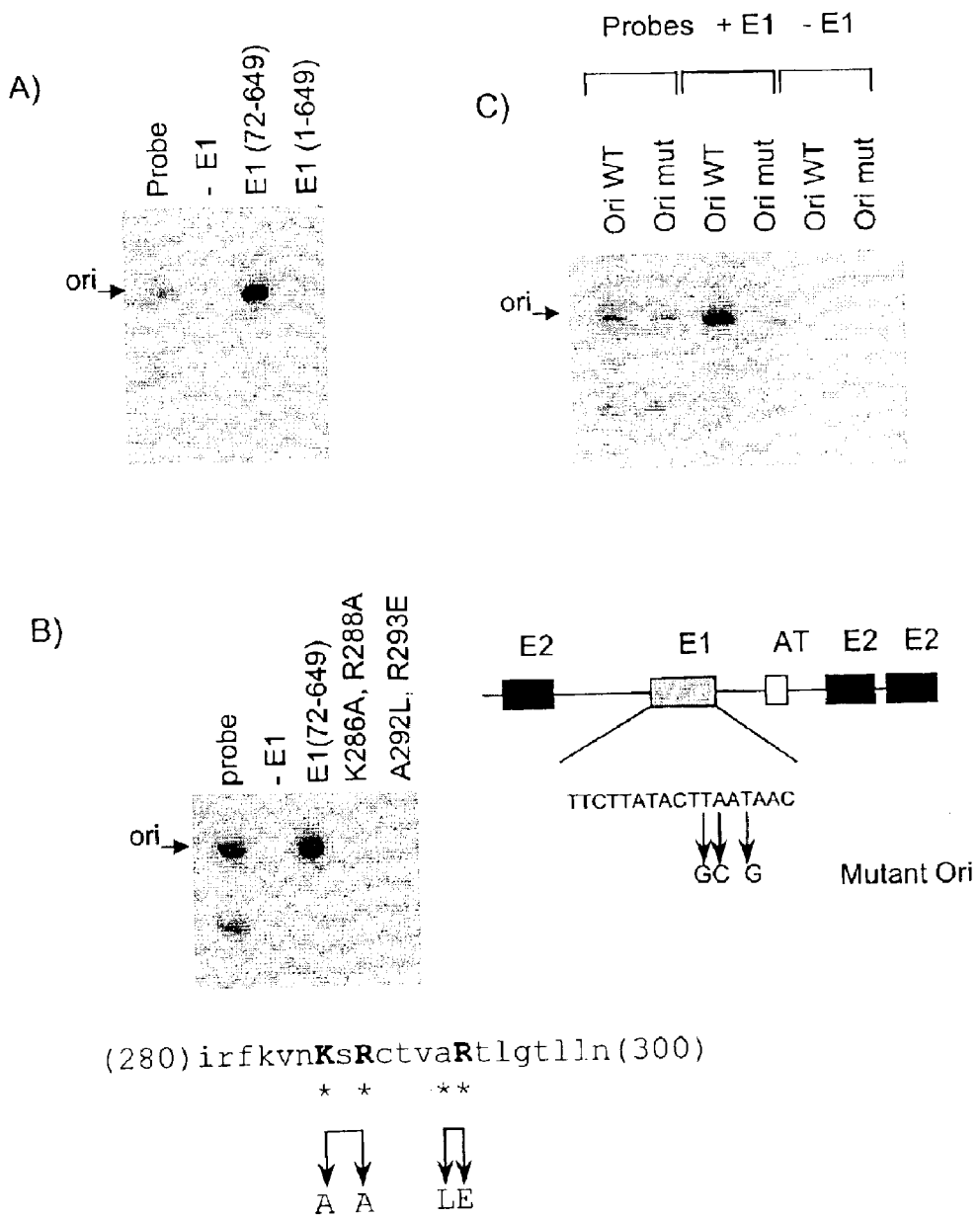
FIG. 3A shows the results of an assay monitoring the binding of E1 to the HPV origin of DNA replication. Protein-DNA complexes were formed with either wild type E1 (amino acids 1–649; SEQ ID No. 1), or a N-terminally truncated E1 (E1*=amino acids 72–649, SEQ ID No. 78), or in the absence of E1 (-E1). E1 -DNA complexes were immunoprecipitated with an antibody directed against E1, and the co-precipitated DNA, along with 0.5% of the amount of probe used in the binding reaction, were visualized by electrophoresis and autoradiography. The autoradiograph shows that truncated N-terminal E1 (SEQ ID No. 78) protein has a higher affinity to the origin than the full length E1 protein. An arrow indicates the fragment of the probe that contains the origin.
FIG. 3B shows the effect of amino acid substitutions in the DNA-binding domain of E1 on the binding of E1 to the origin using the DNA co-immunoprecipitation assay. The position of the two different double amino acid substitutions in E1 are indicated along with the primary sequence of E1 between amino acids 280 and 300. Binding reactions were carried out as described for FIG. 3A. The results of the autoradiograph demonstrate that these substitutions abolished binding of E1 to the origin.
FIG. 3C shows the effect of a triple nucleotide mutation in the HPV-11 origin on binding of E1 to the origin. The HPV-11 origin is diagrammed with the three E2 binding sites (black boxes labeled "E2"), the E1 binding site (gray box) and an AT-rich region (open box). The sequence of a portion of the E1 binding site is indicated along with the position of three nucleotide changes in the mutant origin. Binding reactions were carried out as described for FIG. 3A. The autoradiograph demonstrates that the presence of a triple mutation in the HPV origin of replication inhibited the binding of E1 protein to the origin.

Domains of E1 Required for Binding to the Viral Origin In Vitro (FIGS. 3 and 4)

The above studies in yeast suggested that at least two regions of E1 participate in self-association: a self-association domain (amino acids 435–416) and the ATP-binding domain. To investigate the role of these two regions in E1 oligomerization in vitro, we used an assay that detects the binding of E1 to the HPV origin. By analogy with BPV E1, we anticipated that oligomerization of E1 would occur upon binding to the origin. In this assay, HPV 11 E1 protein that is synthesized by coupled transcription/translation in a rabbit reticulocyte lysate is incubated with a mixture of two radioactive DNA fragments, one of which contains the HPV11 origin. E1 protein-DNA complexes that are formed in this reaction are then immunoprecipitated with an antibody against E1 and the co-precipitated DNA is visualized by gel electrophoresis and autoradiography. In these experiments, a series of truncated E1 proteins were used in addition to the wild type protein, in order to define the minimal domain capable of forming a complex with the origin. All E1 proteins were expressed at similar levels (data not shown). Three observations were made. First, using wild type E1, only a small amount of E1-ori complexes could be formed under the conditions of the assay (FIG. 3A). This is probably because of the large excess of competitor DNA present in these reactions (in the form of the plasmids used to program the lysates) and the low-sequence specificity of E1 for the origin. Second, we observed that a mutant E1 protein lacking the N-terminal 71 residues had increased affinity (approximately 5 fold) for the origin as compared to the wild type protein (FIG. 3A) (herein after called E1*). The mechanism by which deletion of the N-terminus increases the affinity of E1 for the origin is still being investigated. Binding of the truncated E1 molecule to the origin was specific since it was affected by two double amino acid substitutions in the E1-DNA binding surface (FIG. 3B). These two amino acids substitutions are similar to those in BPV-1 E1 which abolish binding of BPV-E1 to the origin (Thorner et al. 1988, J. Virol. 62:2474–2482). Specificity was also demonstrated by showing that a triple mutation in the origin reduced E1 binding (FIG. 3C). This triple point mutation was shown previously, by DNase I footprinting analysis, to lie in the E1 binding site of the origin and to affect binding of E1 (Sun et al., 1995, Virology 216:219–222). The third observation that was made, was that the smaller domain of E1 that could bind to the origin was comprised of amino acids 191–649 (FIG. 4). Further deletion of this domain at the N- or C-terminus abolished origin binding (FIG. 4). The simplest interpretation of these results is that binding and oligomerization of E1 to the origin requires a DNA-binding surface (located between residues 191 and 300) and an oligomerization domain (amino acids 353–649).

Figure 5:
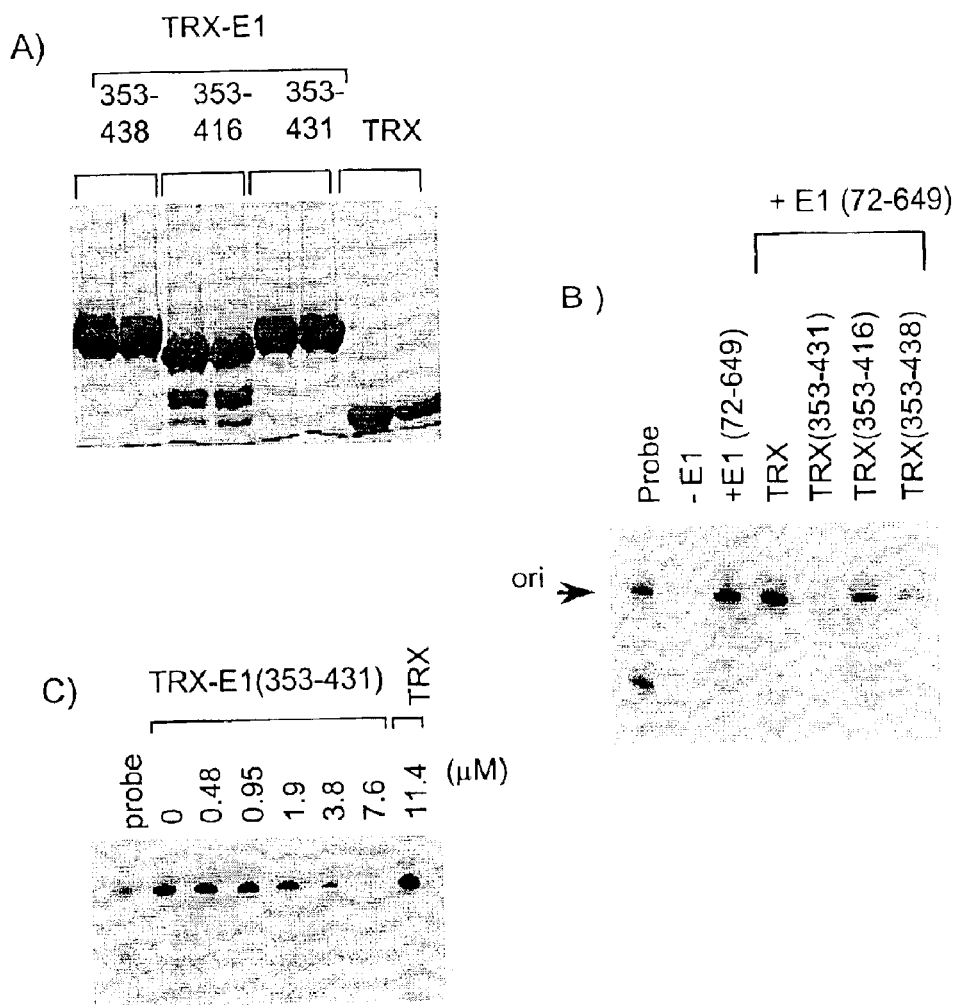
FIG. 5A shows a SDS-PAGE stained with Coomassie blue of the thioredoxin (TRX) fusion proteins containing the indicated portion of E1 expressed in E. coli and purified by nickel-affinity chromatography. The amino acid region of each fragment is shown at the top of the lanes. For each fusion protein, two independent preparations were analyzed.
FIG. 5B shows the effect of excess TRX-E1 fusion products on the binding of E1 (72–649 of SEQ ID No. 1) to the viral origin. Binding reactions were carried out as described in FIG. 4A. TRX fusion proteins, or TRX alone, were added to the binding reactions at a concentration of approximately 8 $\mu$M, which corresponds to a 300-fold molar excess relative to E1 (72–649). The fusion molecule TRX-E1 (353–431; SEQ ID No. 3) showed the highest inhibitory effect and fragment TRX-E1 (353–416; SEQ ID No. 4) demonstrated no apparent inhibition. TRX alone, showed no measurable binding to the origin.
FIG. 5C shows the effect of different concentration of the TRX-E1 (353–431; SEQ ID No. 3) fusion molecule on the binding of E1 to the origin. Decreasing concentration of TRX-E1 (353–649; SEQ ID No. 5) were used to estimate the $IC_{50}$ at which this fusion protein inhibits the binding of E1 to the viral origin. From this data the $IC_{50}$ was estimated at approximately 3 $\mu$M.

A Fusion Protein that Contains the E1—E1 Interaction Domain Inhibits Binding of E1 to the Origin (FIG. 5)

If amino acids 353–431 of E1 encode an E1—E1 interaction domain that is required for oligomerization at the origin, then it would be anticipated that this domain a variant, derivative or fragment thereof, alone, when provided in excess, would inhibit in trans the binding of E1* (72–649) to the origin. To test this hypothesis, fragments of E1: 353–416, 353–431 and 353–438 were expressed in $E.$ $coli$ and purified in soluble form as fusions with thioredoxin. In the absence of thioredoxin as a fusion partner, all three E1 fragments were insoluble (data not shown). The fusion proteins contained a polyhistidine sequence that allowed their purification by nickel-affinity chromatography (FIG. 5A). The three fusion proteins were then tested for the ability to inhibit the binding of E1* (72–649) to the origin, at a concentration of 8 $\mu$M (approximately 300-fold molar excess over E1). As can be seen in FIG. 5B, TRX-E1 (353–431) and TRX-E1(353–438) inhibited binding of E1 to the origin. TRX-E1 (353–416) was not inhibitory at a concentration of 8 $\mu$M, perhaps because this fusion protein is heavily proteolyzed or because it has a lower affinity for E1 as suggested by the two-hybrid studies (see FIG. 2B). Under the same conditions, TRX alone had no effect (FIG. 5B). In these experiments, two independent preparations of each fusion protein were tested with similar results (FIG. 1A and data not shown). The 50% inhibitory concentration for TRX-E1(353–431) was measured to be approximately 3 $\mu$M (FIG. 5C). These results reinforced the notions that region A is required for E1 oligomerization at the origin and that E1(353–431) encodes an E1—E1 interaction domain.

Figure 6:
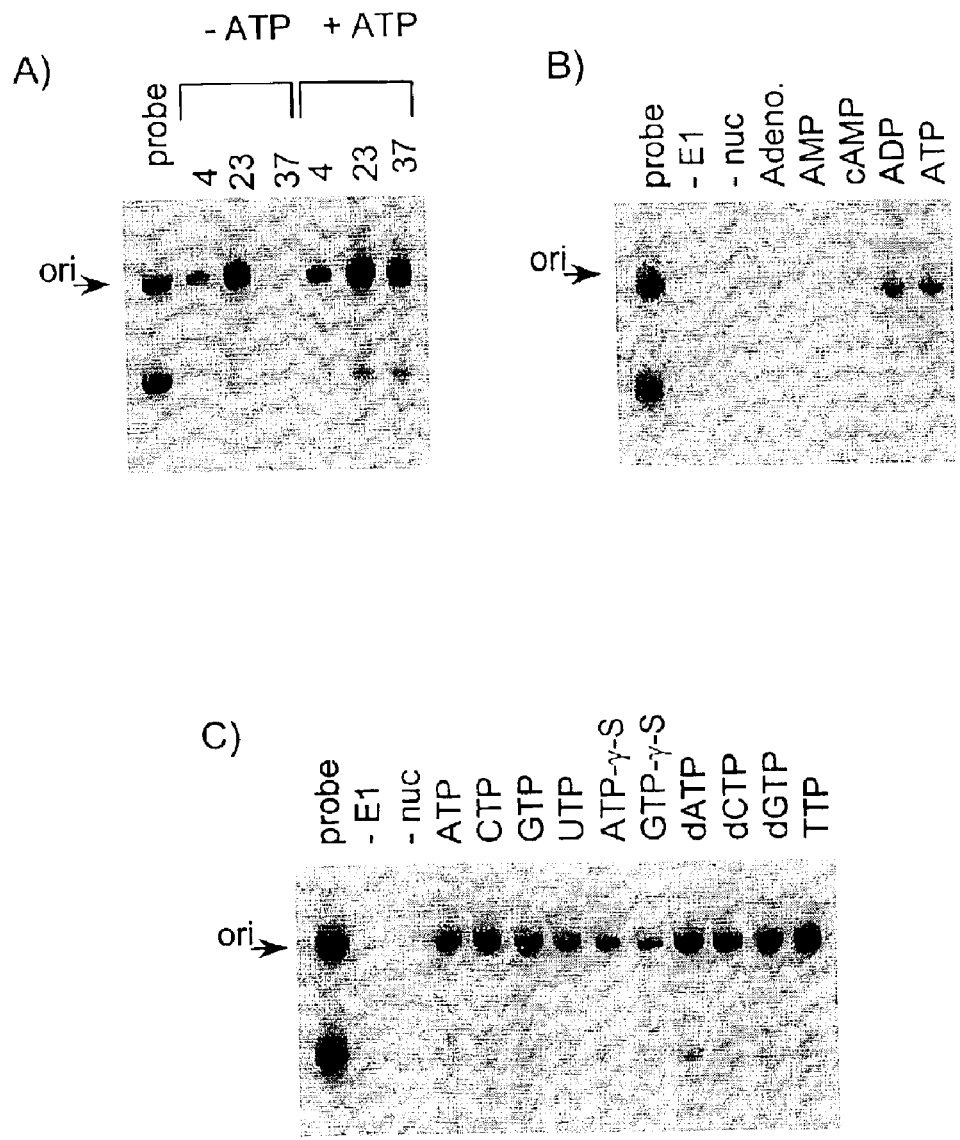
FIG. 6A shows the effect of temperature and nucleotides on the binding of E1* to the viral origin. Binding of E1* (SEQ ID No. 78) to the viral origin was performed at three different temperatures (4°, 23° and 37° C.), and in the presence (+ATP/Mg) or absence (−ATP/Mg) of ATP/Mg at a concentration of 5 and 3 mM, respectively. In the absence of ATP/Mg the binding of E1 to the origin appears to be partially inhibited at 4° C., unchanged at 23° C. and drastically reduced at 37° C. Addition of ATP/Mg at 37° C. reverses this temperature related effect.
FIG. 6B shows that only ADP and ATP in combination with magnesium are capable of stimulating binding of E1 to the origin. Binding of E1 to the origin was performed in the absence of nucleotide (−nuc) or in the presence of the indicated nucleoside triphosphate at a concentration of 5 mM. "Adeno." indicates adenosine and "cAMP" indicates cyclic AMP.
FIG. 6C shows the effect of binding of E1 to the origin in the absence of nucleotide (−nuc) and in the presence of the nucleotides (CTP, GTP and UTP) and the deoxynucleotides (dATP, dCTP, dGTP and dTTP). The results of the autoradiograph show that the nucleotides and deoxynucleotides are able to stimulate binding of E1 to the origin. The non-hydrolyzable analogues (ATP-γ-S and GTP-γ-S) are also stimulatory, indicating that binding of the substrate but not its hydrolysis is necessary for E1 binding to the origin.

Role of ATP and of the E1 ATP-binding Domain in Origin Binding (FIGS. 6 and 7)

Because self-association of E1 in yeast requires an intact ATP-binding domain (see above), we investigated the role of ATP/Mg in E1-Ori complex formation in vitro. This was done by supplementing the binding reactions with ATP/Mg at concentrations of 5 and 3 mM, respectively. The reactions were performed at three different temperatures (4, 23, and 37C). As can be seen in FIG. 6A, in the absence of ATP/Mg, binding of E1 to the origin was reduced dramatically at high temperature (37C). This inhibition by high temperature could be relieved by the addition of ATP/Mg (FIG. 6A). At lower temperatures (23° and 4°) ATP/Mg had only a modest effect. Different types of nucleotides, in combination with magnesium, were tested for their ability to stimulate binding of E1 to the origin. ADP, but not AMP or adenosine, could substitute for ATP (FIG. 6B). Similarly, the three other nucleotides (CTP, GTP, UTP) as well as all four deoxy-nucleotides (dATP, dCTP, dGTP, TTP) could stimulate binding to the origin (FIG. 6C). Two non-hydrolyzable analogues, ATP-$\gamma$-S and GTP-$\gamma$-S were also stimulatory indicating that binding of the substrate, but not its hydrolysis, is necessary for E1 to bind to the origin (FIG. 6C).

Amino acids substitutions in the ATP-binding domain of E1 were tested for their effect on E1 binding to the origin (FIG. 7). Some substitutions affect highly conserved residues of the Walker A motif (FIG. 7A), which is probably involved in binding the triphosphate tail of the substrate nucleotide (Gorbalenya and Koonin, 1993, Current Opinion in Structural Biology 3:419–429). As can be seen in FIG. 7B, these substitutions, including those that prevented E1 self-association in yeast (P479S, K484Q and K484E), reduced E1 binding to the origin. Together with the results presented above, these findings indicate that ATP-binding is required for E1 to bind to the origin.

In these experiments, we also tested the effect of changing highly conserved residues in motif C as well as phenylalanine 509 of E1. These residues are conserved among members of superfamily 3 but their function is unknown. As can be seen in FIG. 7B, replacement of these amino acids by alanine did not abolish binding of E1 to the origin, indicating that they are not essential for this process and for ATP-binding.

Figure 8:
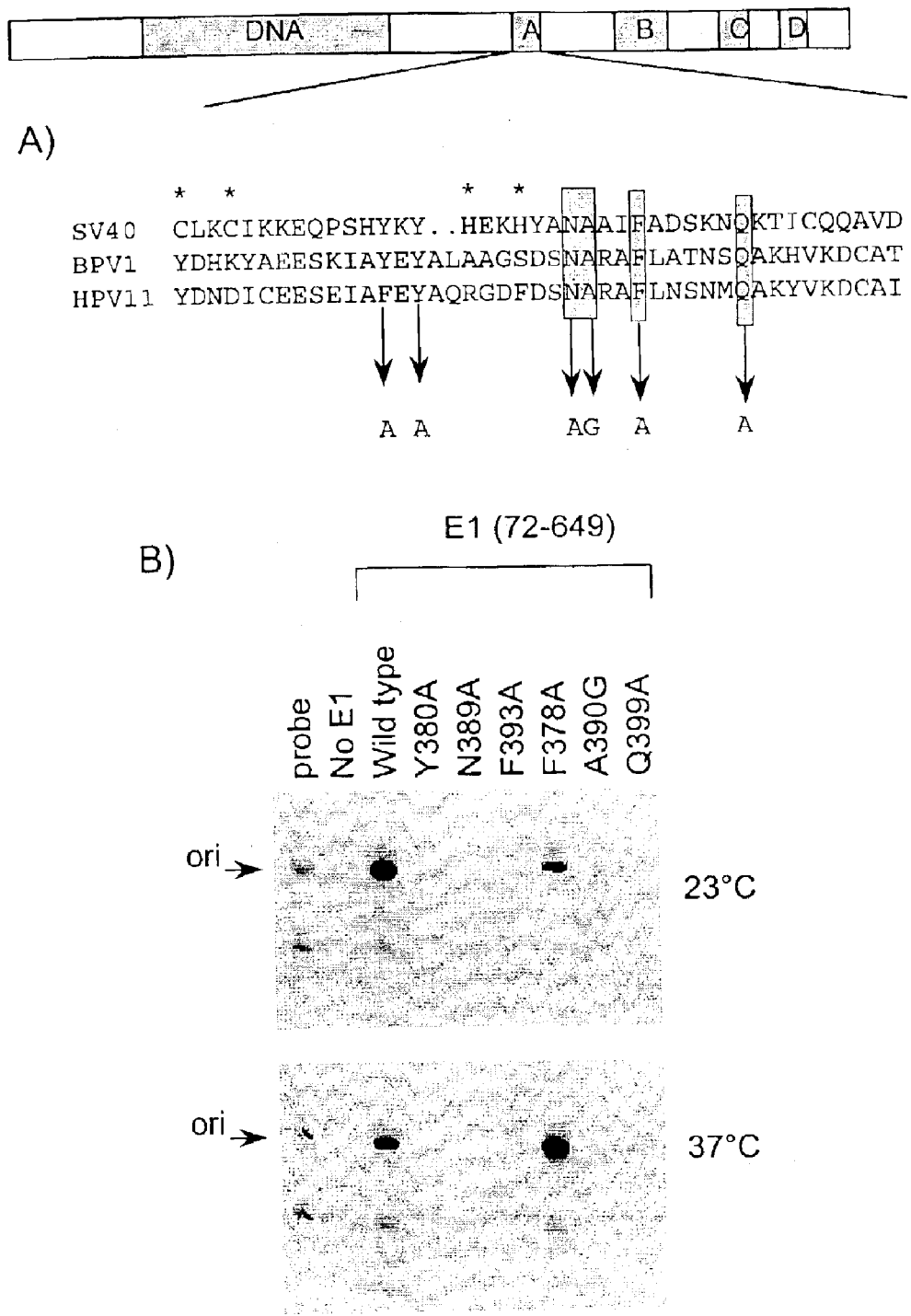
FIG. 8A shows the effect of substitutions in conserved region A of E1 on the binding of E1 to the viral origin. A schematic representation of the E1 protein in which the gray boxes indicate the positions of region A, B, C and D that have high sequence similarity with large T antigens from polyomaviruses, and of the DNA-binding domain. An alignment of conserved region A form SV40 T antigen, BPV-1 and HPV-11 is shown. Highly conserved residues of this region are boxed in gray. Residues that were mutated are also indicated.
FIG. 8B shows the effect of six independent substitutions in region A, on the binding of E1 to the origin. E1* (SEQ ID No. 78), or the indicated mutant derivatives, were tested for binding to the viral origin essentially as described in FIG. 4A. Binding reactions were preformed either at 23° C. in the absence of supplemented ATP/Mg, or in at 37° C. in reactions supplemented with ATP/Mg at concentrations of 5 and 3 mM, respectively. All six substitutions tested reduced binding, indicating that conserved region A is important for E1 to bind to the origin.

Conserved Region A of E1 is Required for E1 Binding to the Origin (FIG. 8)

The E1—E1 interaction domain that was mapped in yeast was comprised of amino acids 353–416. This region of E1 encompasses conserved Region A, one of four regions of high sequence similarity between E1 of various papilloma viruses and the large T antigens of SV40 and polyoma viruses (Clertant and Seif, 1984). To determine if this region is essential for E1 to bind to the origin, six independent amino acid substitutions were created in this domain (F378A, Y380A, N389A, A390G, F393A, Q399A) (FIG. 8A) and tested for their effect on E1-Ori complex formation. Four of the six substitutions affect residues that are invariant between papilloma and polyoma viruses (N389A, A390G, F393A, Q399A) (FIG. 8A). The other two substitutions (F378A and Y380A) affect hydrophobic residues that form part of a zinc-binding motif in large T antigen (FIG. 8A), which is required for oligomerization (Loeber et al., 1991, J. Virology, 65(6):3167–3174). Although this zinc finger motif is not conserved in papilloma viruses, F378 and Y380 lie in a region of E1 which, like the analogous region in large T, is predicted to fold into an alpha helix (data not shown). Binding of these mutant E1 proteins to the origin was assayed both at 23° C. in the absence of supplemented ATP/Mg, and at 37° C. in reactions supplemented with ATP/Mg (5 and 3 mM, respectively). Under both sets of conditions the results were very similar. Three of the substitutions, Y380A, N389A, and F393A, drastically reduced binding of E1 to the origin (FIG. 8B). Two other substitutions, A390G and Q399A, were also deleterious and resulted in only a modest amount of binding of E1 to the origin. Only one substitution, F378A, had little effect on E1 binding to the origin. These results indicated that the structural integrity of conserved region A of E1 is required for E1 to bind to the origin.

Conserved Region A of E1 is Required for Formation of the E1–E2-ori Ternary Complex (FIG. 9A)

To test whether conserved Region A of E1 is required for E2-dependent binding of E1 to the origin, an assay similar to the E1 origin binding assay described above was used, with the following changes; E2, made by in-vitro translation is included in the reaction and the full-length E1 (1–649) is used. As can be seen in FIG. 9A, three of the substitutions (Y380A, N389A, F393A) reduced complex formation dramatically. Two other substitutions (A390G and Q399A) had a less pronounced effect. One substitution, F378A, had only a modest effect on E1–E2-Ori complex formation. These results indicate that the structural integrity of conserved region A is necessary in the formation of the E1–E2-Ori ternary complex.

Effect of Substitutions in Conserved Region A of E1 on Transient HPV DNA Replication (FIG. 9B)

The mutant E1 proteins carrying substitutions in conserved region A, together with E2, were tested for their ability to support replication of an origin-containing plasmid in transiently transfected cells. As can be seen in FIG. 9B, three of the E1 mutants, F378A, A390G, and Q399A were capable of supporting HPV DNA replication, albeit at reduced levels as compared to wild type E1 in the case of A390G and Q399A. Three of the E1 mutants, Y380A, N389A, and F393A, were unable to support replication. These results indicated that conserved region A of E1 is required for transient HPV DNA replication. The ability of the E1 mutants to support transient HPV DNA replication correlated well with their ability to bind to the origin either in the absence or in the presence of E2 (see above). A potential caveat in these experiments is that the stability of the various E1 mutant proteins, as compared to that of the wild type E1, could not be assessed due to the low levels of expression of E1 (data not shown). It is therefore possible that the low level of replication observed with some mutant proteins may also be related to an effect on protein accumulation.

Example 10

Oligomerization Assay using Recombinant E1 Protein

The assay is the same as the one presented in Example 9, but was performed with 75 ng of recombinant purified His-tagged HPV11 E1* (72–649) produced in baculovirus-infected Sf21 insect cells and 200 ng of plasmid DNA as competitor. CHAPS was also added in the binding mix to a final concentration of 0.15%

Example 11

Purification of Recombinant E1* (72–649)

E1* was produced in Sf21 insect cells by infection with recombinant baculoviruses that express a histidine tagged (6 Histidines) E1* (72–649). Infected cells were harvested by centrifugation 48 hrs post-infection and the volume of the cell pellet was then measured. The cell pellet was frozen on dry ice and stored at −80° C.

For purification, the cell pellet was thawed and resuspended in one volume (relative to the volume of the pellet) of hypotonic buffer A (20 mM Tris-HCl pH 8,0; 5 mM β-mercaptoethanol; 5 mM KCl; 1 mM $MgCl_2$; antipain, leupeptin, pepstatin at 1 ug/ml and Pefabloc at 1 mM). After incubation on ice for 15 min. the cell suspension was submitted to 20 strokes of Dounce homogenizer with pestle B. Nuclei were then collected by centrifugation at 2500 g for 20 min. at 4° C. and resuspended to 1,4 volume (relative to the initial cell pellet volume) in buffer B (20 mM Tris-HCl pH 8,0; 5 mM β-mercaptoethanol; antipain, leupeptin, pepstatin at 2 ug/ml and Pefabloc at 2 mM). 1,4 volume of buffer C (20 mM Tris-HCl pH 8,0; 5 mM β-mercaptoethanol; 900 mM NaCl) was then added and the suspension was mixed and incubated with rocking for 30 min. at 4° C. The extract was then centrifuged at 148000 g for 45 min. at 4° C. to pellet the debris. Supernatant was collected and glycerol added to it to a final concentration of 10% before freezing it on dry ice and storing it at −80° C. until chromatography.

For chromatography, the cell extract was thawed and loaded on a 5 ml Hi-Trap column (Pharmacia Biotech) charged with Nickel and equilibrated with 20 mM Tris-HCl pH8,0; 5 mM β-mercaptoethanol; 500 mM NaCl; 10% glycerol. Following loading of the extract, the column was washed with 7–8 volumes of equilibration buffer containing 150 mM imidazole. The bound E1* protein was then eluted with equilibration buffer containing 250 mM imidazole.

Example 12

Oligomerization of E1 In Vitro

Figure 10:
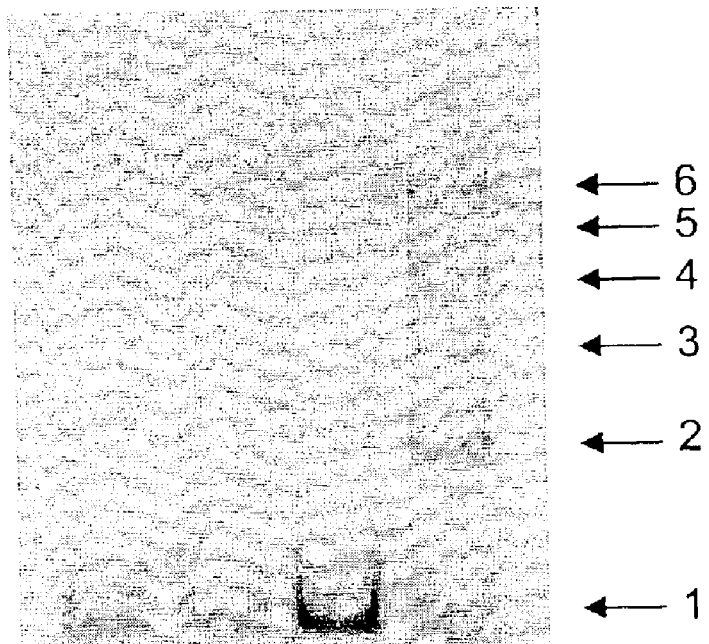
FIG. 10. Cross-linking of radiolabeled E1* demonstrating the formation of oligomers, corresponding in size to monomer (1), dimer (2), trimer (3), tetramer (4), pentamer (5) and hexamer (6) of E1*. Formation of E1* oligomers is stimulated when single stranded DNA is added (+) to the reaction. Oligomers are detected only in the presence (+) of the cross-linking agent BMH.

To detect E1 oligomerization in vitro, we used cross-linking with the sulfhydryl-reacting cross-linker bismale-imidohexane (BMH, Pierce). $^{35}$S-labeled E1* protein (72–649) made by in-vitro transcription/translation (TNT Coupled Reticulocyte Lysate System, Promega), was incubated in the presence or absence of 50 ng/ml single-stranded (ss) DNA (60 mer, corresponding to nucleotides 7902 to 34 of the HPV-11 origin) for 1 hr at two different temperatures, 23° and 370° C. (Final binding conditions: 12.5 µl of translated E1 in a final volume of 37.5 µl containing 20 mM Tris pH 7.6, 100 mM NaCl, 1 mM DTT, 5 mM ATP, 3 mM MgCl$_2$). Cross-linking was performed by diluting the binding reactions 13 fold with phosphate buffer (0.1 M pH 7.0) containing 100 µM BMH. Cross-linking reactions were stopped after 1 min by addition of DTT to a final concentration of 2.5 mM. E1 proteins were then immunoprecipitated with a polyclonal antibody directed against the C-terminal 14 amino acids of HPV-11 and analyzed by gel electrophoresis (3% Weber-Osborn polyacrylamide gel [Weber and Osborn, 1969]) and autoradiography. Under these conditions, single-stranded DNA greatly stimulated cross-linking of E1 into oligomers (FIG. 10). Five different protein bands corresponding to oligomers of E1 were observed in addition to monomeric E1. These oligomeric E1 species, when compared with molecular weight standards, migrated at the expected positions for dimers, trimers, tetramers, pentamers and hexamers (data not shown). The same was also true when cross-linking experiments were performed with truncated E1 proteins (see below) therefore ruling out that proteins from the reticulocyte lysate are part of these complexes. Together, these results indicate that HPV-11 E1 has the capacity to form hexamers upon binding single-stranded DNA. Finally, we have shown that oligomerization of E1 could be stimulated by ss DNA oligonucleotides that are not derived from the HPV origin, indicating that binding of E1 to ss DNA is largely sequence-independent (data not shown).

The C-terminus E1 is Sufficient for Oligomerization

Figure 11:
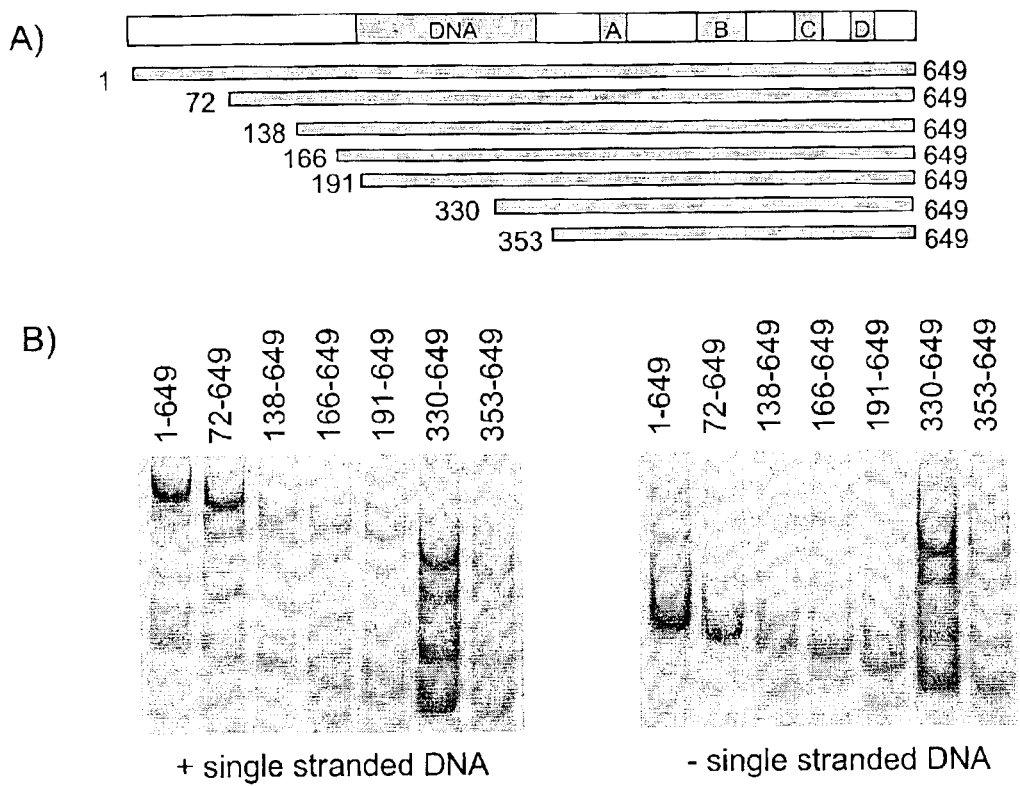
FIG. 11. Cross-linking of rtruncated adiolabeled E1 proteins. The various truncated proteins used in this assay are diagrammed in panel A. Results of the cross-linking experiments are shown in Panel B. Cross-linking was performed as described in Example 12, in the presence (+) or absence (−) of ss DNA.

We then used a set of truncated E1 proteins (FIG. 11) made by in-vitro translation, to map the minimal domain of E1 capable of oligomerization. Residues 353–649 of E1 were found to be sufficient to form oligomers in vitro. Interestingly, the levels of oligomerization of E1 (330–649) and E1 (353–649) were substantial even in absence of single-stranded DNA and were not increased by the addition of ss DNA. The fact that the C-terminus of E1 oligomerizes "constitutively" provides a plausible explanation as to why this domain, in contrast to the complete protein, could readily self-associate in the yeast two hybrid system. The smallest E1 protein whose oligomerization was dependent on ss DNA was comprised of amino acids 191–649. Therefore, the region between residues 191–330 appears to play a critical role in inhibiting oligomerization of the C-terminal domain (330–649) and conferring ss DNA-responsiveness.

Figure 12A:
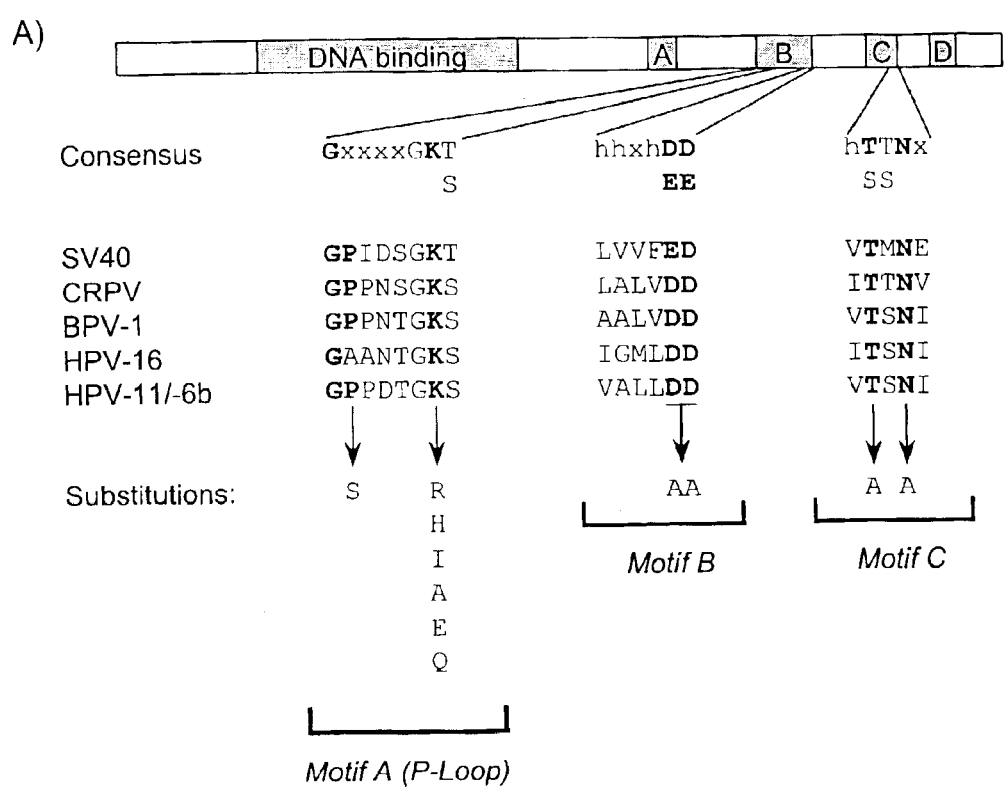
FIG. 12. Effect of amino acids substitutions in the ATP-binding domain of E1* on oligomerization. The location of the various amino acids substitutions made in the E1* ATP-binding domain are summarized in Panel A. Results obtained from the cross-linking of these mutant E1* proteins (72–649) in presence of ss DNA are shown in panel B.
Figure 12B:
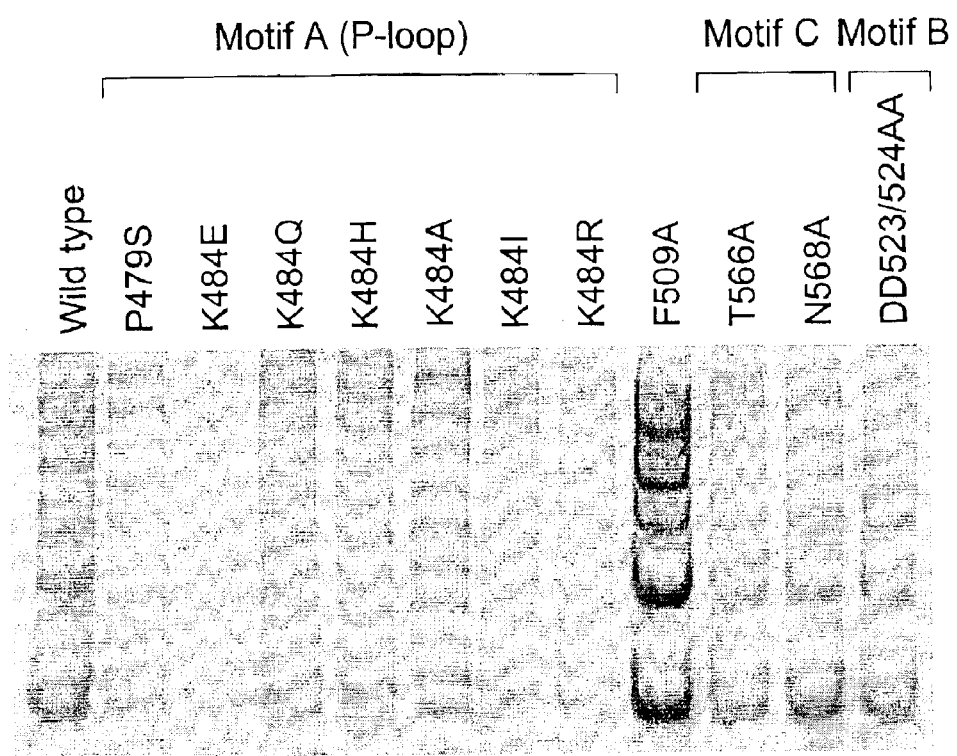

Effect of Amino Acid Substitutions in the ATP-binding Domain of E1 on Oligomerization The region of E1 that is sufficient for oligomerization (residues 353–649) encompasses the ATP-binding domain. We investigated the role of the ATP-binding domain on oligomerization of E1 by testing the effect of mutations that change highly conserved residues implicated in ATP-binding. These mutant E1* proteins (72–649), which were synthesized by in vitro translation, carry amino acid substitutions in one of three motifs, termed A, B and C, which characterize the ATP-binding domain of E1 and of other members of superfamily 3 of NTP-binding proteins (FIG. 12 A). Motifs A and B correspond to the classical Walker A and B motifs, which together bind ATP as a magnesium chelate. Residues in motif A, also known as the phosphate-binding-loop (P-loop), interact with the triphosphate tail of ATP. Motif B is involved in coordinating the magnesium ion associated with the substrate nucleotide. The exact function of conserved motif C is unknown but it has been suggested that it may also participate in binding ATP. Another mutant E1* protein was also tested in which a highly conserved residue, F509, which lies between motifs B and C and whose function is unknown, was mutated. With the exception of F509A substitution, all other substitutions reduced E1 oligomerization to varying degree (FIG. 12 B). Substitutions in motif A had the greater effect indicating that the structural integrity of the P-loop is essential for oligomerization. Substitutions in motifs B or C reduced oligomer formation but did not completely abolish it. Together, these results indicate that the structural integrity of the ATP-binding domain of E1 is essential for oligomerization. The ATP-binding domain could be required to bind ATP, which could allosterically regulate oligomerization. Alternatively, or in addition, the integrity of the ATP-binding domain could be required for the proper folding/stability of the entire C-terminal domain. However, the fact that all of the substitutions that affect oligomerization, with the exception of K484E and K484Q, do not affect binding to E2 (Titolo et al., 1999), suggest that these substitutions do not alter dramatically the overall structure of the C-terminal domain.

Effect of Amino Acid Substitutions in Conserved Region A of E1 Oligomerization

Figure 13:
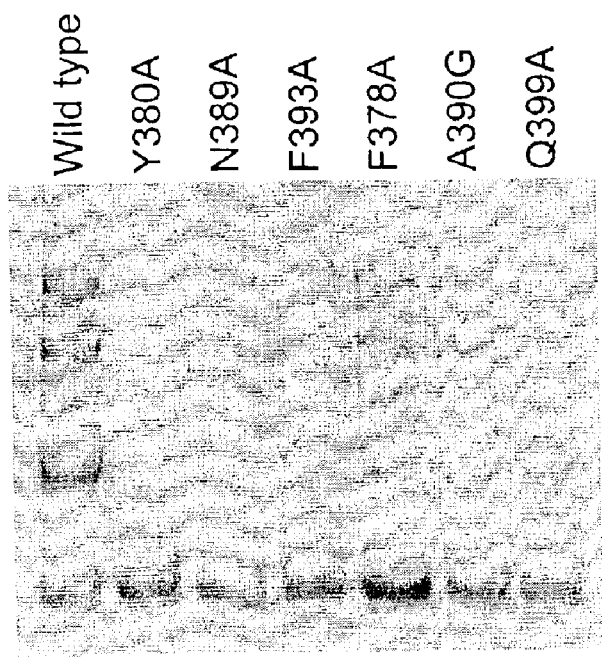
FIG. 13. Effect of amino acids substitutions in conserved Region A of E1* on oligomerization. Six different E1* proteins, each bearing a single amino acid substitution in conserved region A, (indicated above each lane of the gel) were tested by cross-linking for their ability to oligomerize in presence of ss DNA as described in Example 12.

We next tested the effect of amino acids in conserved region A of E1 for their effect on oligomerization of the protein using the cross-linking assay. Six mutant E1* proteins were synthesized by in vitro translation and tested for oligomerization in the presence of ss DNA as described above. Three of the six mutant proteins tested, Y380A, N389A and F393A, were severely defective in this assay (FIG. 13). As expected, these are the same three mutant proteins that are also severely defective in binding/oligomerization at the HPV origin (FIG. 9). These results reinforce the notion that conserved region A of E1 is required for oligomerization.

Conclusion

Without wishing to be bound by theory, Applicant believes that the results provided herein, indicate that the region as defined by SEQ ID NO. 2, SEQ ID NO. 3, or SEQ ID NO. 4, is the region that is necessary for E1 oligomerization. Therefore, this region may serve as a target for inhibiting PV DNA replication for the treatment of PV infection.

TABLE 1

| No. | Plasmid | Oligonucleotide sequence | SEQ ID No. |
|---|---|---|---|
| 1 | pCR3-E1 (1-649)[c] | E1: CAAGG<u>ATG</u>GCGGACGATTCA[a]<br>TCT<u>TCA</u>TAAAGTTCTAACAAC[b] | 15<br>16 |
| 2 | pCR3-E2 (1- ) | E2: GAAG<u>ATG</u>GAAGCAATAGCCAA<br>ATGG<u>TTA</u>CAATAAATGTAATGAC | 17<br>18 |

TABLE 1-continued

| No. | Plasmid | Oligonucleotide sequence | SEQ ID No. |
|---|---|---|---|
| 3 | pCR3-FLAG-E1 (2-649) | CCCATGGACTACAAGGACGACGATGACAAGGCGGACGATTCAGGTACAGAAAAT | 19 |
|  |  | GGGATCCTTATTATAAAGTTCTAACAACTGATCCTG GCAC | 20 |
| 4 | pTM1-E1 | GTACGATCCCATGGCGGACGATTCAGGTACAGAAAAT | 21 |
|  |  | GTACGATGGGATCCTTATTATAAAGTTCTAACAACTGATCCTGGCAC | 22 |
| 5 | pTM1-FLAG-E1 | CCCATGGACTACAAGGACGACGATGACAAGGCGGACGATTCAGGTACAGAAAAT | 23 |
|  |  | GGGATCCTTATTATAAAGTTCTAACAACTGATCCTGGCAC | 24 |
| 6 | pTM1-E1 (1-649) | CCCGGATCCTAATGGCGGACGATTCAGGT (a.a. 1) | 25 |
|  |  | CCCGGATCCTCATAAAGTTCTAACAACT (a.a. 649) | 33 |
| 7 | pTM1-E1 (71-649) | GGCTGGATCCATGGCGGATGCTCATTATGCG (a.a. 72) | 26 |
|  |  | CCCGGATCCTCATAAAGTTCTAACAACT (a.a. 649) | 33 |
| 8 | pTM1-E1 (112-649) | GGCTGGATCGATGGCCATTAAACTTACAACACAG (a.a. 112) | 27 |
|  |  | CCCGGATCCTCATAAAGTTCTAACAACT (a.a. 649) | 33 |
| 9 | pTM1-E1 (138-649) | GGCTGGATCCATGGGCTATTCTGAAGTGGAAG (a.a. 138) | 28 |
|  |  | CCCGGATCCTCATAAAGTTCTAACAACT (a.a. 649) | 33 |
| 10 | pTM1-E1 (166-649) | GGCTGGATCCATGGGGAGGGACATAGAGGGT (a.a. 166) | 29 |
|  |  | CCCGGATCCTCATAAAGTTCTAACAACT (a.a. 649) | 33 |
| 11 | pTM1-E1 (191-649) | GGCTGGATCCATGGACACATCAGGAATATTAGAA (a.a. 191) | 30 |
|  |  | CCCGGATCCTCATAAAGTTCTAACAACT (a.a. 649) | 33 |
| 12 | pTM1-E1 (353-649) | GGCTGGATCCATGGACAGTCAATTTAAATTAACT (a.a. 353) | 31 |
|  |  | CCCGGATCCTCATAAAGTTCTAACAACT (a.a. 649) | 33 |
| 13 | pTM1-E1 (435-649) | GGCTGGATCCATGGACAGTGTAGGTAACTGG (a.a. 435) | 32 |
|  |  | CCCGGATCCTCATAAAGTTCTAACAACT (a.a. 649) | 33 |
| 14 | pTM1-FLAG-E1 (72-649) | GGGGGCCATGGACTACAAGGACGACGACGACAAGGCGGATGCTCATTATGACTG | 34 |
|  |  | CCCGGATCCTCATAAAGTTCTAACAACT (a.a. 649) | 33 |
| 15 | pTM1-FLAG-E1 (72-608) | GGGGGCCATGGACTACAAGGACGACGACGACAAGGCGGATGCTCATTATGACTG | 34 |
|  |  | CCC GGATCCTCATGCATCTGATAGTTCATATACTG (a.a. 608) | 35 |
| 16 | pTM1-FLAG-E1 (72-572) | GGGGGCCATGGACTACAAGGACGACGACGACAAGGCGGATGCTCATTATGACTG | 34 |
|  |  | CCCGGATCCTCAGCTAATGTCTATATTTGATGTAACC (a.a. 572) | 36 |
| 17 | pTM1-FLAG-E1 (72-458) | GGGGGCCATGGACTACAAGGACGACGACGACAAGGCGGATGCTCATTATGACTG | 34 |
|  |  | CCCGGATCCTCATAAAAATGGAATAAATTCTATGTTTTGATG (a.a. 458) | 37 |
| 18 | pTM1-FLAG-E1 (72-344) | GGGGGCCATGGACTACAAGGACGACGACGACAAGGCGGATGCTCATTATGACTG | 34 |
|  |  | CCCGGATCCTCACTGGCGCGTTATCCATTCCGGC (a.a. 344) | 38 |
| 19 | pTM1-FLAG-E1 (72-327) | GGGGGCCATGGACTACAAGGACGACGACGACAAGGCGGATGCTCATTATGACTG | 34 |
|  |  | CCCGGATCCTCAAATGCCTGTCCTAAACCAATAC (a.a. 327) | 39 |

(a) The top sequence in this oligonucleotide pair encodes the forward primer.
(b) The bottom sequence in this oligonucleotide pair encodes the reverse primer.
(c) These numbers represent the amino acid residues comprised in the construct.

TABLE 2

| No. | Plasmid | Oligonucleotide sequence | SEQ ID No. |
|---|---|---|---|
| 1 | pACT2 (1-649) | CCCGGATCCTAATGGCGGACGATTCAGGT | 25 |
|  |  | CCCGGATCCTCATAAAGTTCTAACAACT | 33 |
| 2 | pACT2 (72-649) | GGCTGGATCCATGGCGGATGCTCATTATGCG | 26 |
|  |  | CCCGGATCCTCATAAAGTTCTAACAACT | 33 |
| 3 | pACT2 (138-649) | GGCTGGATCCATGGGCTATTCTGAAGTGGAAG | 28 |
|  |  | CCCGGATCCTCATAAAGTTCTAACAACT | 33 |
| 4 | pACT2 (191-649) | GGCTGGATCCATGGACACATCAGGAATATTAGAA | 30 |
|  |  | CCCGGATCCTCATAAAGTTCTAACAACT | 33 |
| 5 | pACT2 (330-649) | GGCTGGATCCATGGCAAGTACAGTTATAGGGG | 31 |
|  |  | CCCGGATCCTCATAAAGTTCTAACAACT | 33 |

TABLE 2-continued

| No. Plasmid | Oligonucleotide sequence | SEQ ID No. |
|---|---|---|
| 6 pACT2 (353-649) | GGCTGGATCCATGGACAGTCAATTTAAATTAACT<br>CCCGGATCCTCATAAAGTTCTAACAACT | 40<br>33 |
| 7 pACT2 (435-649) | GGCTGGATCCATGGACAGTGTAGGTAACTGG<br>CCCGGATCCTCATAAAGTTCTAACAACT | 32<br>33 |
| 8 ACT2 (353-572) | GGCTGGATCCATGGACAGTCAATTTAAATTAACT<br>CCCGGATCCTCAGCTAATGTCTATATTTGATGTAACC | 40<br>36 |
| 9 pACT2 (353-536) | GGCTGGATCCATGGACAGTCAATTTAAATTAACT<br>CCCGGATCCTCAATATGTATCCATATATGTCCAAC | 40<br>47 |
| 10 pACT2 (353-458) | GGCTGGATCCATGGACAGTCAATTTAAATTAACT<br>CCCGGATCCTCATAAAAATGGAATAAATTCTATGTTTTGATG | 40<br>37 |

TABLE 3

[pAS1 (GAL4-AD)]

| No. Plasmid | Oligonucleotide sequence | SEQ ID No. |
|---|---|---|
| 1 pAS1 (1-649) | CCCGGATCCTAATGGCGGACGATTCAGGT<br>CCCGGATCCTCATAAAGTTCTAACAACT | 25<br>33 |
| 2 pAS1 (353-649) | GGCTGGATCCATGGACAGTCAATTTAAATTAACT<br>CCCGGATCCTCATAAAGTTCTAACAACT | 40<br>33 |
| 3 pAS1 (353-572) | GGCTGGATCCATGGACAGTCAATTTAAATTAACT<br>CCCGGATCCTCAGCTAATGTCTATATTTGATGTAACC | 40<br>36 |
| 4 pAS1 (353-536) | GGCTGGATCCATGGACAGTCAATTTAAATTAACT<br>CCCGGATCCTCAATATGTATCCATATATGTCCAAC | 40<br>47 |
| 5 pAS1 (353-458) | GGCTGGATCCATGGACAGTCAATTTAAATTAACT<br>CCCGGATCCTCATAAAAATGGAATAAATTCTATGTTTTGATG | 40<br>37 |
| 6 pAS1 (353-444) | GGCTGGATCCATGGACAGTCAATTTAAATTAACT<br>CCCGGATCCTATCACACAATTGGCTTCCAGTTACC | 40<br>48 |
| 7 pAS1 (353-438) | GGCTGGATCCATGGACAGTCAATTTAAATTAACT<br>CCCGGATCCTATCAACCTACACTGTCAACTTTAG | 40<br>49 |
| 8 pAS1 (353-431) | GGCTGGATCCATGGACAGTCAATTTAAATTAACT<br>CCCGGATCCTATCAACCCCTATACTTAATCCATTG | 40<br>50 |
| 9 pAS1 (353-416) | GGCTGGATCCATGGACAGTCAATTTAAATTAACT<br>CCCGGATCCTATCATGCATGTTTATAATGTCTGCAC | 40<br>51 |
| 10 pAS1 (365-458) | GGCTGGATCCATGGCATATGATAATGATATTTGTG<br>CCCGGATCCTCATAAAAATGGAATAAATTCTATGTTTTGATG | 41<br>37 |
| 11 pAS1 (377-458) | GGCTGGATCCATGGCATTTGAATATGCACAGCG<br>CCCGGATCCTCATAAAAATGGAATAAATTCTATGTTTTGATG | 42<br>37 |
| 12 pAS1 (384-458) | GGCTGGATCCATGGGAGACTTTGACTCCAATGC<br>CCCGGATCCTCATAAAAATGGAATAAATTCTATGTTTTGATG | 43<br>37 |
| 13 pAS1 (387-458) | GGCTGGATCCATGGACTCCAATGCAAGGGCC<br>CCCGGATCCTCATAAAAATGGAATAAATTCTATGTTTTGATG | 44<br>37 |
| 14 pAS1 (405-458) | GGCTGGATCCATGGATTGTGCAATTATGTGCAG<br>CCCGGATCCTCATAAAAATGGAATAAATTCTATGTTTTGATG | 45<br>37 |
| 15 pAS1 (416-458) | GGCTGGATCCATGGCAGAAATGAAAAAGATGTC<br>CCCGGATCCTCATAAAAATGGAATAAATTCTATGTTTTGATG | 46<br>37 |
| 16 pAS1 (435-649) | GGCTGGATCCATGGACAGTGTAGGTAACTGG<br>CCCGGATCCTCATAAAGTTCTAACAACT | 32<br>33 |

What is claimed is:

1. An oligomerization assay comprising the steps of:
   a. combining an E1 protein comprising the amino acid sequence of SEQ ID NO: 78, and capable of self-association and of associating with a full length E1 protein, with a DNA fragment, and incubating for a period of time to allow the E1 protein and the DNA to form a complex, b. isolating said E1 protein/DNA complex from the non-complexed DNA; and c. detecting said DNA, wherein the presence of DNA is an indication of E1 protein binding to PV origin, and thereby correlates with E1 oligomerization.

2. An assay for screening for an agent capable of inhibiting E1-oligomerization, this assay comprising the steps according to claim 1 and further comprising the steps of:

a. contacting an agent to the E1 protein prior to combining with the DNA fragment and incubating for a period of time to allow E1 protein/DNA to form a complex; and b. comparing the results with a control sample, wherein the control sample is similarly treated but without the addition of said agent.

3. The assay of claim 1, wherein said DNA contains an origin of replication.

4. The assay of claim 3, wherein said E1 is combined with a mixture of two DNA fragments, one of which containing an origin of replication and the second one consisting of a different length DNA such that it is distinguishable from the ori-containing DNA and that the amount of E1 bound to the ori-containing DNA may be compared to the amount of non-specific binding.

5. The assay of claim 1, wherein said E1-DNA complex is isolated from the free DNA by column chromatography, centrifugation, extraction, filtration, immunoprecipitation or immobilized on solid support using an antibody directed against E1 protein.

6. The assay of claim 5, wherein said E1-DNA is isolated by immobilizing the antibody to a solid medium such as a bead or a bottom of a well from a testing plate such that when the medium is removed so is the free DNA.

7. The assay of claim 5, wherein said antibody is a polyclonal antibody.

8. The assay of claim 1, wherein said complexed DNA is released from said E1/DNA complex before said DNA is detected.

9. The assay of claim 8, wherein said DNA is labeled with a radioisotope, and detected by gel electrophoresis followed by radioactive imaging.

10. The assay of claim 8, wherein said DNA is labeled with a calorimetric dye and detected spectrophotometrically.

11. The assay of claim 1 or 2, wherein said assay is carried out in the presence of ATP/Mg.

12. The assay of claim 11, wherein saud assay is carried out at a temperature of 37° C. or higher.

* * * * *

SEQUENCE LISTING

<160> NUMBER OF SEQ ID NOS: 79

<210> SEQ ID NO 1
<211> LENGTH: 649
<212> TYPE: PRT
<213> ORGANISM: HPV-11 E1

<400> SEQUENCE: 1

```
Met Ala Asp Asp Ser Gly Thr Glu Asn Glu Gly Ser Gly Cys Thr Gly
  1               5                  10                  15

Trp Phe Met Val Glu Ala Ile Val Glu His Thr Thr Gly Thr Gln Ile
             20                  25                  30

Ser Glu Asp Glu Glu Glu Glu Val Glu Asp Ser Gly Tyr Asp Met Val
         35                  40                  45

Asp Phe Ile Asp Asp Arg His Ile Thr Gln Asn Ser Val Glu Ala Gln
     50                  55                  60

Ala Leu Phe Asn Arg Gln Glu Ala Asp Ala His Tyr Ala Thr Val Gln
 65                  70                  75                  80

Asp Leu Lys Arg Lys Tyr Leu Gly Ser Pro Tyr Val Ser Pro Ile Ser
                 85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Arg Leu Phe Glu
        115                 120                 125

Thr Arg Glu Leu Thr Asp Ser Gly Tyr Gly Tyr Ser Glu Val Glu Ala
    130                 135                 140

Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Glu Gly Val Glu His
                165                 170                 175

Arg Glu Ala Glu Ala Val Asp Asp Ser Thr Arg Glu His Ala Asp Thr
            180                 185                 190

Ser Gly Ile Leu Glu Leu Leu Lys Cys Lys Asp Ile Arg Ser Thr Leu
        195                 200                 205

His Gly Lys Phe Lys Asp Cys Phe Gly Leu Ser Phe Val Asp Leu Ile
    210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
        275                 280                 285

Cys Thr Val Ala Arg Thr Leu Gly Thr Leu Leu Asn Ile Pro Glu Asn
    290                 295                 300

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
```

-continued

```
                355                 360                 365
Asp Ile Cys Glu Glu Ser Glu Ile Ala Phe Glu Tyr Ala Gln Arg Gly
            370                 375                 380

Asp Phe Asp Ser Asn Ala Arg Ala Phe Leu Asn Ser Asn Met Gln Ala
385                 390                 395                 400

Lys Tyr Val Lys Asp Cys Ala Ile Met Cys Arg His Tyr Lys His Ala
            405                 410                 415

Glu Met Lys Lys Met Ser Ile Lys Gln Trp Ile Lys Tyr Arg Gly Thr
                420                 425                 430

Lys Val Asp Ser Val Gly Asn Trp Lys Pro Ile Val Gln Phe Leu Arg
            435                 440                 445

His Gln Asn Ile Glu Phe Ile Pro Phe Leu Ser Lys Leu Lys Leu Trp
        450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
                500                 505                 510

Pro Leu Thr Asp Ala Lys Val Ala Leu Leu Asp Asp Ala Thr Gln Pro
            515                 520                 525

Cys Trp Thr Tyr Met Asp Thr Tyr Met Arg Asn Leu Leu Asp Gly Asn
        530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
        595                 600                 605

Asn Trp Lys Cys Phe Phe Glu Arg Leu Ser Ser Ser Leu Asp Ile Glu
    610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

<210> SEQ ID NO 2
<211> LENGTH: 86
<212> TYPE: PRT
<213> ORGANISM: HPV-11 E1

<400> SEQUENCE: 2

Asp Ser Gln Phe Lys Leu Thr Glu Met Val Gln Trp Ala Tyr Asp Asn
1               5                   10                  15

Asp Ile Cys Glu Glu Ser Glu Ile Ala Phe Glu Tyr Ala Gln Arg Gly
                20                  25                  30

Asp Phe Asp Ser Asn Ala Arg Ala Phe Leu Asn Ser Asn Met Gln Ala
            35                  40                  45

Lys Tyr Val Lys Asp Cys Ala Ile Met Cys Arg His Tyr Lys His Ala
        50                  55                  60

Glu Met Lys Lys Met Ser Ile Lys Gln Trp Ile Lys Tyr Arg Gly Thr
65                  70                  75                  80
```

```
Lys Val Asp Ser Val Gly
                85

<210> SEQ ID NO 3
<211> LENGTH: 79
<212> TYPE: PRT
<213> ORGANISM: HPV-11 E1

<400> SEQUENCE: 3

Asp Ser Gln Phe Lys Leu Thr Glu Met Val Gln Trp Ala Tyr Asp Asn
 1               5                  10                  15

Asp Ile Cys Glu Glu Ser Glu Ile Ala Phe Glu Tyr Ala Gln Arg Gly
            20                  25                  30

Asp Phe Asp Ser Asn Ala Arg Ala Phe Leu Asn Ser Asn Met Gln Ala
        35                  40                  45

Lys Tyr Val Lys Asp Cys Ala Ile Met Cys Arg His Tyr Lys His Ala
    50                  55                  60

Glu Met Lys Lys Met Ser Ile Lys Gln Trp Ile Lys Tyr Arg Gly
65                  70                  75

<210> SEQ ID NO 4
<211> LENGTH: 64
<212> TYPE: PRT
<213> ORGANISM: HOV-11 E1

<400> SEQUENCE: 4

Asp Ser Gln Phe Lys Leu Thr Glu Met Val Gln Trp Ala Tyr Asp Asn
 1               5                  10                  15

Asp Ile Cys Glu Glu Ser Glu Ile Ala Phe Glu Tyr Ala Gln Arg Gly
            20                  25                  30

Asp Phe Asp Ser Asn Ala Arg Ala Phe Leu Asn Ser Asn Met Gln Ala
        35                  40                  45

Lys Tyr Val Lys Asp Cys Ala Ile Met Cys Arg His Tyr Lys His Ala
    50                  55                  60

<210> SEQ ID NO 5
<211> LENGTH: 317
<212> TYPE: PRT
<213> ORGANISM: HPV-11 E1

<400> SEQUENCE: 5

Val Ile Gly Glu Ala Pro Glu Trp Ile Thr Arg Gln Thr Val Ile Glu
 1               5                  10                  15

His Ser Leu Ala Asp Ser Gln Phe Lys Leu Thr Glu Met Val Gln Trp
            20                  25                  30

Ala Tyr Asp Asn Asp Ile Cys Glu Glu Ser Glu Ile Ala Phe Glu Tyr
        35                  40                  45

Ala Gln Arg Gly Asp Phe Asp Ser Asn Ala Arg Ala Phe Leu Asn Ser
    50                  55                  60

Asn Met Gln Ala Lys Tyr Val Lys Asp Cys Ala Ile Met Cys Arg His
65                  70                  75                  80

Tyr Lys His Ala Glu Met Lys Lys Met Ser Ile Lys Gln Trp Ile Lys
                85                  90                  95

Tyr Arg Gly Thr Lys Val Asp Ser Val Gly Asn Trp Lys Pro Ile Val
            100                 105                 110

Gln Phe Leu Arg His Gln Asn Ile Glu Phe Ile Pro Phe Leu Ser Lys
        115                 120                 125

Leu Lys Leu Trp Leu His Gly Thr Pro Lys Lys Asn Cys Ile Ala Ile
```

-continued

```
            130                 135                 140
Val Gly Pro Pro Asp Thr Gly Lys Ser Cys Phe Cys Met Ser Leu Ile
145                 150                 155                 160

Lys Phe Leu Gly Gly Thr Val Ile Ser Tyr Val Asn Ser Cys Ser His
                165                 170                 175

Phe Trp Leu Gln Pro Leu Thr Asp Ala Lys Val Ala Leu Leu Asp Asp
            180                 185                 190

Ala Thr Gln Pro Cys Trp Thr Tyr Met Asp Thr Tyr Met Arg Asn Leu
        195                 200                 205

Leu Asp Gly Asn Pro Met Ser Ile Asp Arg Lys His Arg Ala Leu Thr
210                 215                 220

Leu Ile Lys Cys Pro Leu Leu Val Thr Ser Asn Ile Asp Ile Ser
225                 230                 235                 240

Lys Glu Glu Lys Tyr Lys Tyr Leu His Ser Arg Val Thr Thr Phe Thr
                245                 250                 255

Phe Pro Asn Pro Phe Pro Phe Asp Arg Asn Gly Asn Ala Val Tyr Glu
            260                 265                 270

Leu Ser Asp Ala Asn Trp Lys Cys Phe Phe Glu Arg Leu Ser Ser Ser
        275                 280                 285

Leu Asp Ile Glu Asp Ser Glu Asp Glu Glu Asp Gly Ser Asn Ser Gln
290                 295                 300

Ala Phe Arg Cys Val Pro Gly Ser Val Val Arg Thr Leu
305                 310                 315

<210> SEQ ID NO 6
<211> LENGTH: 317
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 6

Val Ile Gly Glu Ala Pro Glu Trp Ile Thr Arg Gln Thr Val Ile Glu
1               5                   10                  15

His Ser Leu Ala Asp Ser Gln Phe Lys Leu Thr Glu Met Val Gln Trp
            20                  25                  30

Ala Tyr Asp Asn Asp Ile Cys Glu Glu Ser Glu Ile Ala Phe Glu Tyr
        35                  40                  45

Ala Gln Arg Gly Asp Phe Asp Ser Asn Ala Arg Ala Phe Leu Asn Ser
    50                  55                  60

Asn Met Gln Ala Lys Tyr Val Lys Asp Cys Ala Ile Met Cys Arg His
65                  70                  75                  80

Tyr Lys His Ala Glu Met Lys Lys Met Ser Ile Lys Gln Trp Ile Lys
                85                  90                  95

Tyr Arg Gly Thr Lys Val Asp Ser Val Gly Asn Trp Lys Pro Ile Val
            100                 105                 110

Gln Phe Leu Arg His Gln Asn Ile Glu Phe Ile Pro Phe Leu Ser Lys
        115                 120                 125

Leu Lys Leu Trp Leu His Gly Thr Pro Lys Lys Asn Cys Ile Ala Ile
    130                 135                 140

Val Gly Ser Pro Asp Thr Gly Lys Ser Cys Phe Cys Met Ser Leu Ile
145                 150                 155                 160

Lys Phe Leu Gly Gly Thr Val Ile Ser Tyr Val Asn Ser Cys Ser His
                165                 170                 175
```

-continued

```
Phe Trp Leu Gln Pro Leu Thr Asp Ala Lys Val Ala Leu Leu Asp Asp
            180                 185                 190

Ala Thr Gln Pro Cys Trp Thr Tyr Met Asp Thr Tyr Met Arg Asn Leu
        195                 200                 205

Leu Asp Gly Asn Pro Met Ser Ile Asp Arg Lys His Arg Ala Leu Thr
        210                 215                 220

Leu Ile Lys Cys Pro Leu Leu Val Thr Ser Asn Ile Asp Ile Ser
225                 230                 235                 240

Lys Glu Glu Lys Tyr Lys Tyr Leu His Ser Arg Val Thr Thr Phe Thr
                245                 250                 255

Phe Pro Asn Pro Phe Pro Phe Asp Arg Asn Gly Asn Ala Val Tyr Glu
            260                 265                 270

Leu Ser Asp Ala Asn Trp Lys Cys Phe Phe Glu Arg Leu Ser Ser Ser
        275                 280                 285

Leu Asp Ile Glu Asp Ser Glu Asp Glu Glu Asp Gly Ser Asn Ser Gln
        290                 295                 300

Ala Phe Arg Cys Val Pro Gly Ser Val Val Arg Thr Leu
305                 310                 315
```

<210> SEQ ID NO 7
<211> LENGTH: 317
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 7

```
Val Ile Gly Glu Ala Pro Glu Trp Ile Thr Arg Gln Thr Val Ile Glu
1               5                   10                  15

His Ser Leu Ala Asp Ser Gln Phe Lys Leu Thr Glu Met Val Gln Trp
                20                  25                  30

Ala Tyr Asp Asn Asp Ile Cys Glu Glu Ser Glu Ile Ala Phe Glu Tyr
            35                  40                  45

Ala Gln Arg Gly Asp Phe Asp Ser Asn Ala Arg Ala Phe Leu Asn Ser
        50                  55                  60

Asn Met Gln Ala Lys Tyr Val Lys Asp Cys Ala Ile Met Cys Arg His
65                  70                  75                  80

Tyr Lys His Ala Glu Met Lys Lys Met Ser Ile Lys Gln Trp Ile Lys
                85                  90                  95

Tyr Arg Gly Thr Lys Val Asp Ser Val Gly Asn Trp Lys Pro Ile Val
            100                 105                 110

Gln Phe Leu Arg His Gln Asn Ile Glu Phe Ile Pro Phe Leu Ser Lys
        115                 120                 125

Leu Lys Leu Trp Leu His Gly Thr Pro Lys Lys Asn Cys Ile Ala Ile
        130                 135                 140

Val Gly Pro Pro Asp Thr Gly Glu Ser Cys Phe Cys Met Ser Leu Ile
145                 150                 155                 160

Lys Phe Leu Gly Gly Thr Val Ile Ser Tyr Val Asn Ser Cys Ser His
                165                 170                 175

Phe Trp Leu Gln Pro Leu Thr Asp Ala Lys Val Ala Leu Leu Asp Asp
            180                 185                 190

Ala Thr Gln Pro Cys Trp Thr Tyr Met Asp Thr Tyr Met Arg Asn Leu
        195                 200                 205

Leu Asp Gly Asn Pro Met Ser Ile Asp Arg Lys His Arg Ala Leu Thr
        210                 215                 220
```

```
Leu Ile Lys Cys Pro Pro Leu Leu Val Thr Ser Asn Ile Asp Ile Ser
225                 230                 235                 240

Lys Glu Glu Lys Tyr Lys Tyr Leu His Ser Arg Val Thr Thr Phe Thr
            245                 250                 255

Phe Pro Asn Pro Phe Pro Phe Asp Arg Asn Gly Asn Ala Val Tyr Glu
            260                 265                 270

Leu Ser Asp Ala Asn Trp Lys Cys Phe Phe Glu Arg Leu Ser Ser Ser
        275                 280                 285

Leu Asp Ile Glu Asp Ser Glu Asp Glu Glu Asp Gly Ser Asn Ser Gln
    290                 295                 300

Ala Phe Arg Cys Val Pro Gly Ser Val Val Arg Thr Leu
305                 310                 315
```

<210> SEQ ID NO 8
<211> LENGTH: 317
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 8

```
Val Ile Gly Glu Ala Pro Glu Trp Ile Thr Arg Gln Thr Val Ile Glu
1               5                   10                  15

His Ser Leu Ala Asp Ser Gln Phe Lys Leu Thr Glu Met Val Gln Trp
            20                  25                  30

Ala Tyr Asp Asn Asp Ile Cys Glu Glu Ser Glu Ile Ala Phe Glu Tyr
        35                  40                  45

Ala Gln Arg Gly Asp Phe Asp Ser Asn Ala Arg Ala Phe Leu Asn Ser
    50                  55                  60

Asn Met Gln Ala Lys Tyr Val Lys Asp Cys Ala Ile Met Cys Arg His
65                  70                  75                  80

Tyr Lys His Ala Glu Met Lys Lys Met Ser Ile Lys Gln Trp Ile Lys
                85                  90                  95

Tyr Arg Gly Thr Lys Val Asp Ser Val Gly Asn Trp Lys Pro Ile Val
            100                 105                 110

Gln Phe Leu Arg His Gln Asn Ile Glu Phe Ile Pro Phe Leu Ser Lys
        115                 120                 125

Leu Lys Leu Trp Leu His Gly Thr Pro Lys Lys Asn Cys Ile Ala Ile
130                 135                 140

Val Gly Pro Pro Asp Thr Gly Gln Ser Cys Phe Cys Met Ser Leu Ile
145                 150                 155                 160

Lys Phe Leu Gly Gly Thr Val Ile Ser Tyr Val Asn Ser Cys Ser His
                165                 170                 175

Phe Trp Leu Gln Pro Leu Thr Asp Ala Lys Val Ala Leu Leu Asp Asp
            180                 185                 190

Ala Thr Gln Pro Cys Trp Thr Tyr Met Asp Thr Tyr Met Arg Asn Leu
        195                 200                 205

Leu Asp Gly Asn Pro Met Ser Ile Asp Arg Lys His Arg Ala Leu Thr
    210                 215                 220

Leu Ile Lys Cys Pro Pro Leu Leu Val Thr Ser Asn Ile Asp Ile Ser
225                 230                 235                 240

Lys Glu Glu Lys Tyr Lys Tyr Leu His Ser Arg Val Thr Thr Phe Thr
                245                 250                 255

Phe Pro Asn Pro Phe Pro Phe Asp Arg Asn Gly Asn Ala Val Tyr Glu
```

```
                    260                 265                 270
Leu Ser Asp Ala Asn Trp Lys Cys Phe Phe Glu Arg Leu Ser Ser Ser
            275                 280                 285

Leu Asp Ile Glu Asp Ser Glu Asp Glu Glu Asp Gly Ser Asn Ser Gln
            290                 295                 300

Ala Phe Arg Cys Val Pro Gly Ser Val Val Arg Thr Leu
305                 310                 315

<210> SEQ ID NO 9
<211> LENGTH: 649
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 9

Met Ala Asp Asp Ser Gly Thr Glu Asn Glu Gly Ser Gly Cys Thr Gly
  1               5                  10                  15

Trp Phe Met Val Glu Ala Ile Val Glu His Thr Thr Gly Thr Gln Ile
                 20                  25                  30

Ser Glu Asp Glu Glu Glu Val Glu Asp Ser Gly Tyr Asp Met Val
             35                  40                  45

Asp Phe Ile Asp Asp Arg His Ile Thr Gln Asn Ser Val Glu Ala Gln
 50                  55                  60

Ala Leu Phe Asn Arg Gln Glu Ala Asp Ala His Tyr Ala Thr Val Gln
 65                  70                  75                  80

Asp Leu Lys Arg Lys Tyr Leu Gly Ser Pro Tyr Val Ser Pro Ile Ser
                 85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Arg Leu Phe Glu
            115                 120                 125

Thr Arg Glu Leu Thr Asp Ser Gly Tyr Gly Tyr Ser Glu Val Glu Ala
130                 135                 140

Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Glu Gly Val Glu His
                165                 170                 175

Arg Glu Ala Glu Ala Val Asp Asp Ser Thr Arg Glu His Ala Asp Thr
            180                 185                 190

Ser Gly Ile Leu Glu Leu Leu Lys Cys Lys Asp Ile Arg Ser Thr Leu
        195                 200                 205

His Gly Lys Phe Lys Asp Cys Phe Gly Leu Ser Phe Val Asp Leu Ile
    210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
        275                 280                 285

Cys Thr Val Ala Arg Thr Leu Gly Thr Leu Leu Asn Ile Pro Glu Asn
    290                 295                 300
```

```
His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Ala Ala Gln Arg Gly
    370                 375                 380

Asp Phe Asp Ser Asn Ala Arg Ala Phe Leu Asn Ser Asn Met Gln Ala
385                 390                 395                 400

Lys Tyr Val Lys Asp Cys Ala Ile Met Cys Arg His Tyr Lys His Ala
                405                 410                 415

Glu Met Lys Lys Met Ser Ile Lys Gln Trp Ile Lys Tyr Arg Gly Thr
            420                 425                 430

Lys Val Asp Ser Val Gly Asn Trp Lys Pro Ile Val Gln Phe Leu Arg
        435                 440                 445

His Gln Asn Ile Glu Phe Ile Pro Phe Leu Ser Lys Leu Lys Leu Trp
    450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
            500                 505                 510

Pro Leu Thr Asp Ala Lys Val Ala Leu Leu Asp Asp Ala Thr Gln Pro
        515                 520                 525

Cys Trp Thr Tyr Met Asp Thr Tyr Met Arg Asn Leu Leu Asp Gly Asn
    530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
        595                 600                 605

Asn Trp Lys Cys Phe Phe Glu Arg Leu Ser Ser Ser Leu Asp Ile Glu
    610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

<210> SEQ ID NO 10
<211> LENGTH: 649
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 10

Met Ala Asp Asp Ser Gly Thr Glu Asn Glu Gly Ser Gly Cys Thr Gly
1               5                   10                  15
```

```
Trp Phe Met Val Glu Ala Ile Val Glu His Thr Thr Gly Thr Gln Ile
             20                  25                  30

Ser Glu Asp Glu Glu Glu Val Glu Asp Ser Gly Tyr Asp Met Val
         35                  40                  45

Asp Phe Ile Asp Asp Arg His Ile Thr Gln Asn Ser Val Glu Ala Gln
         50                  55                  60

Ala Leu Phe Asn Arg Gln Glu Ala Asp Ala His Tyr Ala Thr Val Gln
 65                  70                  75                  80

Asp Leu Lys Arg Lys Tyr Leu Gly Ser Pro Tyr Val Ser Pro Ile Ser
                 85                  90                  95

Asn Val Ala Asn Ala Val Glu Ser Glu Ile Ser Pro Arg Leu Asp Ala
                100                 105                 110

Ile Lys Leu Thr Thr Gln Pro Lys Val Lys Arg Arg Leu Phe Glu
             115                 120                 125

Thr Arg Glu Leu Thr Asp Ser Gly Tyr Gly Tyr Ser Glu Val Glu Ala
         130                 135                 140

Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Gly Val Glu His
                165                 170                 175

Arg Glu Ala Glu Ala Val Asp Asp Ser Thr Arg Glu His Ala Asp Thr
                180                 185                 190

Ser Gly Ile Leu Glu Leu Leu Lys Cys Lys Asp Ile Arg Ser Thr Leu
             195                 200                 205

His Gly Lys Phe Lys Asp Cys Phe Gly Leu Ser Phe Val Asp Leu Ile
         210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
             260                 265                 270

Gly Met Val Leu Leu Val Leu Ile Arg Phe Lys Val Asn Lys Ser Arg
         275                 280                 285

Cys Thr Val Ala Arg Thr Leu Gly Thr Leu Leu Asn Ile Pro Glu Asn
290                 295                 300

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
             340                 345                 350

Asp Ser Gln Phe Lys Leu Thr Glu Met Val Gln Trp Ala Tyr Asp Asn
         355                 360                 365

Asp Ile Cys Glu Glu Ser Glu Ile Ala Phe Glu Tyr Ala Gln Arg Gly
     370                 375                 380

Asp Phe Asp Ser Asn Ala Arg Ala Ala Leu Asn Ser Asn Met Gln Ala
385                 390                 395                 400

Lys Tyr Val Lys Asp Cys Ala Ile Met Cys Arg His Tyr Lys His Ala
                405                 410                 415

Glu Met Lys Lys Met Ser Ile Lys Gln Trp Ile Lys Tyr Arg Gly Thr
             420                 425                 430
```

-continued

```
Lys Val Asp Ser Val Gly Asn Trp Lys Pro Ile Val Gln Phe Leu Arg
            435                 440                 445

His Gln Asn Ile Glu Phe Ile Pro Phe Leu Ser Lys Leu Lys Leu Trp
        450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
            500                 505                 510

Pro Leu Thr Asp Ala Lys Val Ala Leu Leu Asp Asp Ala Thr Gln Pro
        515                 520                 525

Cys Trp Thr Tyr Met Asp Thr Tyr Met Arg Asn Leu Leu Asp Gly Asn
530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
        595                 600                 605

Asn Trp Lys Cys Phe Phe Glu Arg Leu Ser Ser Ser Leu Asp Ile Glu
610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645
```

<210> SEQ ID NO 11
<211> LENGTH: 649
<212> TYPE: PRT
<213> ORGANISM: Artificial Sequence
<220> FEATURE:
<223> OTHER INFORMATION: Description of Artificial Sequence:HPV-11 E1 mutated

<400> SEQUENCE: 11

```
Met Ala Asp Asp Ser Gly Thr Glu Asn Glu Gly Ser Gly Cys Thr Gly
1               5                   10                  15

Trp Phe Met Val Glu Ala Ile Val Glu His Thr Thr Gly Thr Gln Ile
            20                  25                  30

Ser Glu Asp Glu Glu Glu Val Glu Asp Ser Gly Tyr Asp Met Val
        35                  40                  45

Asp Phe Ile Asp Asp Arg His Ile Thr Gln Asn Ser Val Glu Ala Gln
    50                  55                  60

Ala Leu Phe Asn Arg Gln Glu Ala Asp Ala His Tyr Ala Thr Val Gln
65                  70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Leu Phe Glu
        115                 120                 125

Thr Arg Glu Leu Thr Asp Ser Gly Tyr Gly Tyr Ser Glu Val Glu Ala
130                 135                 140
```

```
Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Glu Gly Val Glu His
            165                 170                 175

Arg Glu Ala Glu Ala Val Asp Asp Ser Thr Arg Glu His Ala Asp Thr
        180                 185                 190

Ser Gly Ile Leu Glu Leu Leu Lys Cys Lys Asp Ile Arg Ser Thr Leu
            195                 200                 205

His Gly Lys Phe Lys Asp Cys Phe Gly Leu Ser Phe Val Asp Leu Ile
    210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
    275                 280                 285

Cys Thr Val Ala Arg Thr Leu Gly Thr Leu Leu Asn Ile Pro Glu Asn
290                 295                 300

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
    370                 375                 380

Asp Phe Asp Ser Ala Ala Arg Ala Phe Leu Asn Ser Asn Met Gln Ala
385                 390                 395                 400

Lys Tyr Val Lys Asp Cys Ala Ile Met Cys Arg His Tyr Lys His Ala
                405                 410                 415

Glu Met Lys Lys Met Ser Ile Lys Gln Trp Ile Lys Tyr Arg Gly Thr
            420                 425                 430

Lys Val Asp Ser Val Gly Asn Trp Lys Pro Ile Val Gln Phe Leu Arg
        435                 440                 445

His Gln Asn Ile Glu Phe Ile Pro Phe Leu Ser Lys Leu Lys Leu Trp
    450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
            500                 505                 510

Pro Leu Thr Asp Ala Lys Val Ala Leu Leu Asp Asp Ala Thr Gln Pro
        515                 520                 525

Cys Trp Thr Tyr Met Asp Thr Tyr Met Arg Asn Leu Leu Asp Gly Asn
    530                 535                 540

Pro Met Ser Ile Asp Arg Lys His Arg Ala Leu Thr Leu Ile Lys Cys
545                 550                 555                 560
```

-continued

```
Pro Pro Leu Leu Val Thr Ser Asn Ile Asp Ile Ser Lys Glu Glu Lys
                565                 570                 575
Tyr Lys Tyr Leu His Ser Arg Val Thr Thr Phe Thr Phe Pro Asn Pro
            580                 585                 590
Phe Pro Phe Asp Arg Asn Gly Asn Ala Val Tyr Glu Leu Ser Asp Ala
        595                 600                 605
Asn Trp Lys Cys Phe Phe Glu Arg Leu Ser Ser Ser Leu Asp Ile Glu
    610                 615                 620
Asp Ser Glu Asp Glu Glu Asp Gly Ser Asn Ser Gln Ala Phe Arg Cys
625                 630                 635                 640
Val Pro Gly Ser Val Val Arg Thr Leu
                645

<210> SEQ ID NO 12
<211> LENGTH: 649
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 12

Met Ala Asp Asp Ser Gly Thr Glu Asn Glu Gly Ser Gly Cys Thr Gly
  1               5                  10                  15
Trp Phe Met Val Glu Ala Ile Val Glu His Thr Thr Gly Thr Gln Ile
                 20                  25                  30
Ser Glu Asp Glu Glu Glu Glu Val Glu Asp Ser Gly Tyr Asp Met Val
             35                  40                  45
Asp Phe Ile Asp Asp Arg His Ile Thr Gln Asn Ser Val Glu Ala Gln
         50                  55                  60
Ala Leu Phe Asn Arg Gln Glu Ala Asp Ala His Tyr Ala Thr Val Gln
 65                  70                  75                  80
Asp Leu Lys Arg Lys Tyr Leu Gly Ser Pro Tyr Val Ser Pro Ile Ser
                 85                  90                  95
Asn Val Ala Asn Ala Val Glu Ser Glu Ile Ser Pro Arg Leu Asp Ala
                100                 105                 110
Ile Lys Leu Thr Thr Gln Pro Lys Lys Val Lys Arg Arg Leu Phe Glu
            115                 120                 125
Thr Arg Glu Leu Thr Asp Ser Gly Tyr Gly Tyr Ser Glu Val Glu Ala
        130                 135                 140
Ala Thr Gln Val Glu Lys His Gly Asp Pro Glu Asn Gly Gly Asp Gly
145                 150                 155                 160
Glu Glu Arg Asp Thr Gly Arg Asp Ile Glu Gly Glu Gly Val Glu His
                165                 170                 175
Arg Glu Ala Glu Ala Val Asp Asp Ser Thr Arg Glu His Ala Asp Thr
                180                 185                 190
Ser Gly Ile Leu Glu Leu Leu Lys Cys Lys Asp Ile Arg Ser Thr Leu
            195                 200                 205
His Gly Lys Phe Lys Asp Cys Phe Gly Leu Ser Phe Val Asp Leu Ile
        210                 215                 220
Arg Pro Phe Lys Ser Asp Arg Thr Thr Cys Ala Asp Trp Val Val Ala
225                 230                 235                 240
Gly Phe Gly Ile His His Ser Ile Ala Asp Ala Phe Gln Lys Leu Ile
                245                 250                 255
Glu Pro Leu Ser Leu Tyr Ala His Ile Gln Trp Leu Thr Asn Ala Trp
                260                 265                 270
```

```
Gly Met Val Leu Leu Val Leu Ile Arg Phe Lys Val Asn Lys Ser Arg
            275                 280                 285

Cys Thr Val Ala Arg Thr Leu Gly Thr Leu Leu Asn Ile Pro Glu Asn
        290                 295                 300

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
370                 375                 380

Asp Phe Asp Ser Asn Gly Arg Ala Phe Leu Asn Ser Asn Met Gln Ala
385                 390                 395                 400

Lys Tyr Val Lys Asp Cys Ala Ile Met Cys Arg His Tyr Lys His Ala
                405                 410                 415

Glu Met Lys Lys Met Ser Ile Lys Gln Trp Ile Lys Tyr Arg Gly Thr
            420                 425                 430

Lys Val Asp Ser Val Gly Asn Trp Lys Pro Ile Val Gln Phe Leu Arg
        435                 440                 445

His Gln Asn Ile Glu Phe Ile Pro Phe Leu Ser Lys Leu Lys Leu Trp
450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
            500                 505                 510

Pro Leu Thr Asp Ala Lys Val Ala Leu Leu Asp Asp Ala Thr Gln Pro
        515                 520                 525

Cys Trp Thr Tyr Met Asp Thr Tyr Met Arg Asn Leu Leu Asp Gly Asn
530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
        595                 600                 605

Asn Trp Lys Cys Phe Phe Glu Arg Leu Ser Ser Leu Asp Ile Glu
610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

<210> SEQ ID NO 13
<211> LENGTH: 649
<212> TYPE: PRT
<213> ORGANISM: Artificial Sequence
<220> FEATURE:
```

<223> OTHER INFORMATION: Description of Artificial Sequence:HPV-11 E1 mutated

<400> SEQUENCE: 13

```
Met Ala Asp Asp Ser Gly Thr Glu Asn Glu Gly Ser Gly Cys Thr Gly
 1               5                  10                  15

Trp Phe Met Val Glu Ala Ile Val Glu His Thr Thr Gly Thr Gln Ile
            20                  25                  30

Ser Glu Asp Glu Glu Glu Val Glu Asp Ser Gly Tyr Asp Met Val
        35                  40                  45

Asp Phe Ile Asp Asp Arg His Ile Thr Gln Asn Ser Val Glu Ala Gln
50                  55                  60

Ala Leu Phe Asn Arg Gln Glu Ala Asp Ala His Tyr Ala Thr Val Gln
65                  70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Arg Leu Phe Glu
        115                 120                 125

Thr Arg Glu Leu Thr Asp Ser Gly Tyr Gly Tyr Ser Glu Val Glu Ala
130                 135                 140

Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Glu Gly Val Glu His
                165                 170                 175

Arg Glu Ala Glu Ala Val Asp Asp Ser Thr Arg Glu His Ala Asp Thr
            180                 185                 190

Ser Gly Ile Leu Glu Leu Leu Lys Cys Lys Asp Ile Arg Ser Thr Leu
        195                 200                 205

His Gly Lys Phe Lys Asp Cys Phe Gly Leu Ser Phe Val Asp Leu Ile
    210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
        275                 280                 285

Cys Thr Val Ala Arg Thr Leu Gly Thr Leu Leu Asn Ile Pro Glu Asn
290                 295                 300

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
    370                 375                 380

Asp Phe Asp Ser Asn Ala Arg Ala Phe Leu Asn Ser Asn Met Ala Ala
385                 390                 395                 400
```

```
Lys Tyr Val Lys Asp Cys Ala Ile Met Cys Arg His Tyr Lys His Ala
                405                 410                 415
Glu Met Lys Lys Met Ser Ile Lys Gln Trp Ile Lys Tyr Arg Gly Thr
            420                 425                 430
Lys Val Asp Ser Val Gly Asn Trp Lys Pro Ile Val Gln Phe Leu Arg
        435                 440                 445
His Gln Asn Ile Glu Phe Ile Pro Phe Leu Ser Lys Leu Lys Leu Trp
    450                 455                 460
Leu His Gly Thr Pro Lys Lys Asn Cys Ile Ala Ile Val Gly Pro Pro
465                 470                 475                 480
Asp Thr Gly Lys Ser Cys Phe Cys Met Ser Leu Ile Lys Phe Leu Gly
                485                 490                 495
Gly Thr Val Ile Ser Tyr Val Asn Ser Cys Ser His Phe Trp Leu Gln
            500                 505                 510
Pro Leu Thr Asp Ala Lys Val Ala Leu Leu Asp Asp Ala Thr Gln Pro
        515                 520                 525
Cys Trp Thr Tyr Met Asp Thr Tyr Met Arg Asn Leu Leu Asp Gly Asn
    530                 535                 540
Pro Met Ser Ile Asp Arg Lys His Arg Ala Leu Thr Leu Ile Lys Cys
545                 550                 555                 560
Pro Pro Leu Leu Val Thr Ser Asn Ile Asp Ile Ser Lys Glu Glu Lys
                565                 570                 575
Tyr Lys Tyr Leu His Ser Arg Val Thr Thr Phe Thr Phe Pro Asn Pro
            580                 585                 590
Phe Pro Phe Asp Arg Asn Gly Asn Ala Val Tyr Glu Leu Ser Asp Ala
        595                 600                 605
Asn Trp Lys Cys Phe Phe Glu Arg Leu Ser Ser Ser Leu Asp Ile Glu
    610                 615                 620
Asp Ser Glu Asp Glu Glu Asp Gly Ser Asn Ser Gln Ala Phe Arg Cys
625                 630                 635                 640
Val Pro Gly Ser Val Val Arg Thr Leu
                645

<210> SEQ ID NO 14
<211> LENGTH: 649
<212> TYPE: PRT
<213> ORGANISM: Artificial Sequence
<220> FEATURE:
<223> OTHER INFORMATION: Description of Artificial Sequence:HPV-11 E1
      mutated

<400> SEQUENCE: 14

Met Ala Asp Asp Ser Gly Thr Glu Asn Glu Gly Ser Gly Cys Thr Gly
1               5                   10                  15
Trp Phe Met Val Glu Ala Ile Val Glu His Thr Thr Gly Thr Gln Ile
            20                  25                  30
Ser Glu Asp Glu Glu Glu Val Glu Asp Ser Gly Tyr Asp Met Val
        35                  40                  45
Asp Phe Ile Asp Asp Arg His Ile Thr Gln Asn Ser Val Glu Ala Gln
    50                  55                  60
Ala Leu Phe Asn Arg Gln Glu Ala Asp Ala His Tyr Ala Thr Val Gln
65                  70                  75                  80
Asp Leu Lys Arg Lys Tyr Leu Gly Ser Pro Tyr Val Ser Pro Ile Ser
                85                  90                  95
Asn Val Ala Asn Ala Val Glu Ser Glu Ile Ser Pro Arg Leu Asp Ala
```

-continued

```
                100                 105                 110
Ile Lys Leu Thr Thr Gln Pro Lys Val Lys Arg Arg Leu Phe Glu
            115                 120                 125
Thr Arg Glu Leu Thr Asp Ser Gly Tyr Gly Tyr Ser Glu Val Glu Ala
130                 135                 140
Ala Thr Gln Val Glu Lys His Gly Asp Pro Glu Asn Gly Gly Asp Gly
145                 150                 155                 160
Glu Glu Arg Asp Thr Gly Arg Asp Ile Glu Gly Gly Val Glu His
                165                 170                 175
Arg Glu Ala Glu Ala Val Asp Asp Ser Thr Arg Glu His Ala Asp Thr
                180                 185                 190
Ser Gly Ile Leu Glu Leu Leu Lys Cys Lys Asp Ile Arg Ser Thr Leu
                195                 200                 205
His Gly Lys Phe Lys Asp Cys Phe Gly Leu Ser Phe Val Asp Leu Ile
                210                 215                 220
Arg Pro Phe Lys Ser Asp Arg Thr Thr Cys Ala Asp Trp Val Val Ala
225                 230                 235                 240
Gly Phe Gly Ile His His Ser Ile Ala Asp Ala Phe Gln Lys Leu Ile
                245                 250                 255
Glu Pro Leu Ser Leu Tyr Ala His Ile Gln Trp Leu Thr Asn Ala Trp
                260                 265                 270
Gly Met Val Leu Leu Val Leu Ile Arg Phe Lys Val Asn Lys Ser Arg
            275                 280                 285
Cys Thr Val Ala Arg Thr Leu Gly Thr Leu Leu Asn Ile Pro Glu Asn
290                 295                 300
His Met Leu Ile Glu Pro Pro Lys Ile Gln Ser Gly Val Ala Ala Leu
305                 310                 315                 320
Tyr Trp Phe Arg Thr Gly Ile Ser Asn Ala Ser Thr Val Ile Gly Glu
                325                 330                 335
Ala Pro Glu Trp Ile Thr Arg Gln Thr Val Ile Glu His Ser Leu Ala
                340                 345                 350
Asp Ser Gln Phe Lys Leu Thr Glu Met Val Gln Trp Ala Tyr Asp Asn
                355                 360                 365
Asp Ile Cys Glu Glu Ser Glu Ile Ala Ala Glu Tyr Ala Gln Arg Gly
370                 375                 380
Asp Phe Asp Ser Asn Ala Arg Ala Phe Leu Asn Ser Asn Met Gln Ala
385                 390                 395                 400
Lys Tyr Val Lys Asp Cys Ala Ile Met Cys Arg His Tyr Lys His Ala
                405                 410                 415
Glu Met Lys Lys Met Ser Ile Lys Gln Trp Ile Lys Tyr Arg Gly Thr
                420                 425                 430
Lys Val Asp Ser Val Gly Asn Trp Lys Pro Ile Val Gln Phe Leu Arg
                435                 440                 445
His Gln Asn Ile Glu Phe Ile Pro Phe Leu Ser Lys Leu Lys Leu Trp
                450                 455                 460
Leu His Gly Thr Pro Lys Lys Asn Cys Ile Ala Ile Val Gly Pro Pro
465                 470                 475                 480
Asp Thr Gly Lys Ser Cys Phe Cys Met Ser Leu Ile Lys Phe Leu Gly
                485                 490                 495
Gly Thr Val Ile Ser Tyr Val Asn Ser Cys Ser His Phe Trp Leu Gln
                500                 505                 510
Pro Leu Thr Asp Ala Lys Val Ala Leu Leu Asp Asp Ala Thr Gln Pro
                515                 520                 525
```

```
Cys Trp Thr Tyr Met Asp Thr Tyr Met Arg Asn Leu Leu Asp Gly Asn
    530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
                595                 600                 605

Asn Trp Lys Cys Phe Phe Glu Arg Leu Ser Ser Ser Leu Asp Ile Glu
    610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

<210> SEQ ID NO 15
<211> LENGTH: 20
<212> TYPE: DNA
<213> ORGANISM: synthetic construct

<400> SEQUENCE: 15
caaggatggc ggacgattca                                              20

<210> SEQ ID NO 16
<211> LENGTH: 21
<212> TYPE: DNA
<213> ORGANISM: synthetic construct

<400> SEQUENCE: 16
tcttcataaa gttctaacaa c                                            21

<210> SEQ ID NO 17
<211> LENGTH: 21
<212> TYPE: DNA
<213> ORGANISM: synthetic construct

<400> SEQUENCE: 17
gaagatggaa gcaatagcca a                                            21

<210> SEQ ID NO 18
<211> LENGTH: 23
<212> TYPE: DNA
<213> ORGANISM: synthetic construct

<400> SEQUENCE: 18
atggttacaa taaatgtaat gac                                          23

<210> SEQ ID NO 19
<211> LENGTH: 52
<212> TYPE: DNA
<213> ORGANISM: synthetic construct

<400> SEQUENCE: 19
catggactac aaggacgacg atgacaaggc ggacgattca ggtacagaaa at          52

<210> SEQ ID NO 20
<211> LENGTH: 40
<212> TYPE: DNA
```

<213> ORGANISM: synthetic construct

<400> SEQUENCE: 20
gggatcctta ttataaagtt ctaacaactg atcctggcac          40

<210> SEQ ID NO 21
<211> LENGTH: 37
<212> TYPE: DNA
<213> ORGANISM: synthetic construct

<400> SEQUENCE: 21
gtacgatccc atggcggacg attcaggtac agaaaat             37

<210> SEQ ID NO 22
<211> LENGTH: 47
<212> TYPE: DNA
<213> ORGANISM: synthetic construct

<400> SEQUENCE: 22
gtacgatggg atccttatta taagttcta acaactgatc ctggcac    47

<210> SEQ ID NO 23
<211> LENGTH: 54
<212> TYPE: DNA
<213> ORGANISM: synthetic construct

<400> SEQUENCE: 23
cccatggact acaaggacga cgatgacaag gcggacgatt caggtacaga aaat    54

<210> SEQ ID NO 24
<211> LENGTH: 40
<212> TYPE: DNA
<213> ORGANISM: synthetic construct

<400> SEQUENCE: 24
gggatcctta ttataaagtt ctaacaactg atcctggcac          40

<210> SEQ ID NO 25
<211> LENGTH: 29
<212> TYPE: DNA
<213> ORGANISM: synthetic construct

<400> SEQUENCE: 25
cccggatcct aatggcggac gattcaggt                      29

<210> SEQ ID NO 26
<211> LENGTH: 31
<212> TYPE: DNA
<213> ORGANISM: synthetic construct

<400> SEQUENCE: 26
ggctggatcc atggcggatg ctcattatgc g                   31

<210> SEQ ID NO 27
<211> LENGTH: 34
<212> TYPE: DNA
<213> ORGANISM: synthetic construct

<400> SEQUENCE: 27
ggctggatcc atggccatta aacttacaac acag                34

<210> SEQ ID NO 28
<211> LENGTH: 32

```
<212> TYPE: DNA
<213> ORGANISM: synthetic construct

<400> SEQUENCE: 28
ggctggatcc atgggctatt ctgaagtgga ag                                32

<210> SEQ ID NO 29
<211> LENGTH: 31
<212> TYPE: DNA
<213> ORGANISM: synthetic construct

<400> SEQUENCE: 29
ggctggatcc atggggaggg acatagaggg t                                 31

<210> SEQ ID NO 30
<211> LENGTH: 34
<212> TYPE: DNA
<213> ORGANISM: synthetic construct

<400> SEQUENCE: 30
ggctggatcc atggacacat caggaatatt agaa                              34

<210> SEQ ID NO 31
<211> LENGTH: 34
<212> TYPE: DNA
<213> ORGANISM: synthetic construct

<400> SEQUENCE: 31
ggctggatcc atggacagtc aatttaaatt aact                              34

<210> SEQ ID NO 32
<211> LENGTH: 31
<212> TYPE: DNA
<213> ORGANISM: synthetic construct

<400> SEQUENCE: 32
ggctggatcc atggacagtg taggtaactg g                                 31

<210> SEQ ID NO 33
<211> LENGTH: 28
<212> TYPE: DNA
<213> ORGANISM: synthetic construct

<400> SEQUENCE: 33
cccggatcct cataaagttc taacaact                                     28

<210> SEQ ID NO 34
<211> LENGTH: 54
<212> TYPE: DNA
<213> ORGANISM: synthetic construct

<400> SEQUENCE: 34
gggggccatg gactacaagg acgacgacga caaggcggat gctcattatg actg        54

<210> SEQ ID NO 35
<211> LENGTH: 35
<212> TYPE: DNA
<213> ORGANISM: synthetic construct

<400> SEQUENCE: 35
cccggatcct catgcatctg atagttcata tactg                             35

<210> SEQ ID NO 36
```

<211> LENGTH: 37
<212> TYPE: DNA
<213> ORGANISM: synthetic construct

<400> SEQUENCE: 36
cccggatcct cagctaatgt ctatatttga tgtaacc                                37

<210> SEQ ID NO 37
<211> LENGTH: 42
<212> TYPE: DNA
<213> ORGANISM: synthetic construct

<400> SEQUENCE: 37
cccggatcct cataaaaatg gaataaattc tatgttttga tg                          42

<210> SEQ ID NO 38
<211> LENGTH: 34
<212> TYPE: DNA
<213> ORGANISM: synthetic construct

<400> SEQUENCE: 38
cccggatcct cactggcgcg ttatccattc cggc                                   34

<210> SEQ ID NO 39
<211> LENGTH: 34
<212> TYPE: DNA
<213> ORGANISM: synthetic construct

<400> SEQUENCE: 39
cccggatcct caaatgcctg tcctaaacca atac                                   34

<210> SEQ ID NO 40
<211> LENGTH: 34
<212> TYPE: DNA
<213> ORGANISM: synthetic construct

<400> SEQUENCE: 40
ggctggatcc atggacagtc aatttaaatt aact                                   34

<210> SEQ ID NO 41
<211> LENGTH: 35
<212> TYPE: DNA
<213> ORGANISM: synthetic construct

<400> SEQUENCE: 41
ggctggatcc atggcatatg ataatgatat ttgtg                                  35

<210> SEQ ID NO 42
<211> LENGTH: 33
<212> TYPE: DNA
<213> ORGANISM: synthetic construct

<400> SEQUENCE: 42
ggctggatcc atggcatttg aatatgcaca gcg                                    33

<210> SEQ ID NO 43
<211> LENGTH: 33
<212> TYPE: DNA
<213> ORGANISM: synthetic construct

<400> SEQUENCE: 43
ggctggatcc atgggagact tgactccaa tgc                                     33

```
<210> SEQ ID NO 44
<211> LENGTH: 31
<212> TYPE: DNA
<213> ORGANISM: synthetic construct

<400> SEQUENCE: 44
ggctggatcc atggactcca atgcaagggc c                           31

<210> SEQ ID NO 45
<211> LENGTH: 33
<212> TYPE: DNA
<213> ORGANISM: synthetic construct

<400> SEQUENCE: 45
ggctggatcc atggattgtg caattatgtg cag                         33

<210> SEQ ID NO 46
<211> LENGTH: 33
<212> TYPE: DNA
<213> ORGANISM: synthetic construct

<400> SEQUENCE: 46
ggctggatcc atggcagaaa tgaaaaagat gtc                         33

<210> SEQ ID NO 47
<211> LENGTH: 42
<212> TYPE: DNA
<213> ORGANISM: synthetic construct

<400> SEQUENCE: 47
cccggatcct cataaaaatg gaataaattc tatgttttga tg               42

<210> SEQ ID NO 48
<211> LENGTH: 35
<212> TYPE: DNA
<213> ORGANISM: synthetic construct

<400> SEQUENCE: 48
cccggatcct atcacacaat tggcttccag ttacc                       35

<210> SEQ ID NO 49
<211> LENGTH: 34
<212> TYPE: DNA
<213> ORGANISM: synthetic construct

<400> SEQUENCE: 49
cccggatcct atcaacctac actgtcaact ttag                        34

<210> SEQ ID NO 50
<211> LENGTH: 35
<212> TYPE: DNA
<213> ORGANISM: synthetic construct

<400> SEQUENCE: 50
cccggatcct atcaacccct atacttaatc cattg                       35

<210> SEQ ID NO 51
<211> LENGTH: 36
<212> TYPE: DNA
<213> ORGANISM: synthetic construct

<400> SEQUENCE: 51
cccggatcct atcatgcatg tttataatgt ctgcac                      36
```

<210> SEQ ID NO 52
<211> LENGTH: 29
<212> TYPE: DNA
<213> ORGANISM: synthetic construct

<400> SEQUENCE: 52
cccggatcca gtgtgatgga tatctgcag                29

<210> SEQ ID NO 53
<211> LENGTH: 33
<212> TYPE: DNA
<213> ORGANISM: synthetic construct

<400> SEQUENCE: 53
ggatcctcat tagctaatgt ctatatttga tgt           33

<210> SEQ ID NO 54
<211> LENGTH: 27
<212> TYPE: DNA
<213> ORGANISM: synthetic construct

<400> SEQUENCE: 54
ggatcctcat taatatgtat ccatata                  27

<210> SEQ ID NO 55
<211> LENGTH: 34
<212> TYPE: DNA
<213> ORGANISM: synthetic construct

<400> SEQUENCE: 55
ggatcctcat tataaaaatg gaataaattc tatg          34

<210> SEQ ID NO 56
<211> LENGTH: 28
<212> TYPE: DNA
<213> ORGANISM: synthetic construct

<400> SEQUENCE: 56
gtgagatagc agctgaatat gcacagcg                 28

<210> SEQ ID NO 57
<211> LENGTH: 31
<212> TYPE: DNA
<213> ORGANISM: synthetic construct

<400> SEQUENCE: 57
gagatagcat ttgaagctgc gcagcgtgga g             31

<210> SEQ ID NO 58
<211> LENGTH: 24
<212> TYPE: DNA
<213> ORGANISM: synthetic construct

<400> SEQUENCE: 58
gactttgact ccgcggcaag ggcc                     24

<210> SEQ ID NO 59
<211> LENGTH: 38
<212> TYPE: DNA
<213> ORGANISM: synthetic construct

<400> SEQUENCE: 59
ggagactttg actccaacgg ccgggccttt ttaaatag      38

<210> SEQ ID NO 60
<211> LENGTH: 28
<212> TYPE: DNA
<213> ORGANISM: synthetic construct

<400> SEQUENCE: 60
gcaagggccg cgttaaatag taatatgc                              28

<210> SEQ ID NO 61
<211> LENGTH: 39
<212> TYPE: DNA
<213> ORGANISM: synthetic construct

<400> SEQUENCE: 61
cctttttaaa tagtaatatg gcggctaaat atgtaaaag                  39

<210> SEQ ID NO 62
<211> LENGTH: 25
<212> TYPE: DNA
<213> ORGANISM: synthetic construct

<400> SEQUENCE: 62
ccattgtagg gtcacctgac actgg                                 25

<210> SEQ ID NO 63
<211> LENGTH: 25
<212> TYPE: DNA
<213> ORGANISM: synthetic construct

<400> SEQUENCE: 63
ctgacactgg ggagtcgtgc ttttg                                 25

<210> SEQ ID NO 64
<211> LENGTH: 25
<212> TYPE: DNA
<213> ORGANISM: synthetic construct

<400> SEQUENCE: 64
ctgacactgg gcagtcgtgc ttttg                                 25

<210> SEQ ID NO 65
<211> LENGTH: 27
<212> TYPE: DNA
<213> ORGANISM: synthetic construct

<400> SEQUENCE: 65
cctgacactg ggcactcgtg cttttgc                               27

<210> SEQ ID NO 66
<211> LENGTH: 27
<212> TYPE: DNA
<213> ORGANISM: synthetic construct

<400> SEQUENCE: 66
cctgacactg ggatctcgtg cttttgc                               27

<210> SEQ ID NO 67
<211> LENGTH: 27
<212> TYPE: DNA
<213> ORGANISM: synthetic construct

<400> SEQUENCE: 67
cctgacactg ggcggtcgtg cttttgc                                              27

<210> SEQ ID NO 68
<211> LENGTH: 25
<212> TYPE: DNA
<213> ORGANISM: synthetic construct

<400> SEQUENCE: 68
cctgcagcca cgcgtggcta cagcc                                                25

<210> SEQ ID NO 69
<211> LENGTH: 33
<212> TYPE: DNA
<213> ORGANISM: synthetic construct

<400> SEQUENCE: 69
ccgctactgg ttgctagcaa tatagacatt agc                                       33

<210> SEQ ID NO 70
<211> LENGTH: 34
<212> TYPE: DNA
<213> ORGANISM: synthetic construct

<400> SEQUENCE: 70
ctactggtta catcagcaat tgacattagc aaag                                      34

<210> SEQ ID NO 71
<211> LENGTH: 37
<212> TYPE: DNA
<213> ORGANISM: synthetic construct

<400> SEQUENCE: 71
ggtttaaagt aaatgctagc gcatgtaccg tggcacg                                   37

<210> SEQ ID NO 72
<211> LENGTH: 31
<212> TYPE: DNA
<213> ORGANISM: synthetic construct

<400> SEQUENCE: 72
cagatgtacc gtgctcgaga cattaggtac g                                         31

<210> SEQ ID NO 73
<211> LENGTH: 47
<212> TYPE: DNA
<213> ORGANISM: synthetic construct

<400> SEQUENCE: 73
catatttcct tcttatactg cagaacaatc ttagtttaaa aaagagg                        47

<210> SEQ ID NO 74
<211> LENGTH: 29
<212> TYPE: DNA
<213> ORGANISM: synthetic construct

<400> SEQUENCE: 74
ctgcaaccgg tttcggttac ccacaccct                                            29

<210> SEQ ID NO 75
<211> LENGTH: 28
<212> TYPE: DNA
<213> ORGANISM: synthetic construct

<400> SEQUENCE: 75

-continued

```
cgttccactg agcgtagacc ccgtagaa                                    28
```

<210> SEQ ID NO 76
<211> LENGTH: 18
<212> TYPE: DNA
<213> ORGANISM: synthetic construct

<400> SEQUENCE: 76

```
gctttgggct gtcatttg                                               18
```

<210> SEQ ID NO 77
<211> LENGTH: 18
<212> TYPE: DNA
<213> ORGANISM: synthetic construct

<400> SEQUENCE: 77

```
tgtcaggtgg ccctacaa                                               18
```

<210> SEQ ID NO 78
<211> LENGTH: 578
<212> TYPE: PRT
<213> ORGANISM: Truncated E1

<400> SEQUENCE: 78

```
Ala Asp Ala His Tyr Ala Thr Val Gln Asp Leu Lys Arg Lys Tyr Leu
  1               5                  10                  15

Gly Ser Pro Tyr Val Ser Pro Ile Ser Asn Val Ala Asn Ala Val Glu
             20                  25                  30

Ser Glu Ile Ser Pro Arg Leu Asp Ala Ile Lys Leu Thr Thr Gln Pro
         35                  40                  45

Lys Lys Val Lys Arg Arg Leu Phe Glu Thr Arg Glu Leu Thr Asp Ser
     50                  55                  60

Gly Tyr Gly Tyr Ser Glu Val Glu Ala Ala Thr Gln Val Glu Lys His
 65                  70                  75                  80

Gly Asp Pro Glu Asn Gly Gly Asp Gly Glu Glu Arg Asp Thr Gly Arg
                 85                  90                  95

Asp Ile Glu Gly Glu Gly Val Glu His Arg Glu Ala Glu Ala Val Asp
            100                 105                 110

Asp Ser Thr Arg Glu His Ala Asp Thr Ser Gly Ile Leu Glu Leu Leu
        115                 120                 125

Lys Cys Lys Asp Ile Arg Ser Thr Leu His Gly Lys Phe Lys Asp Cys
    130                 135                 140

Phe Gly Leu Ser Phe Val Asp Leu Ile Arg Pro Phe Lys Ser Asp Arg
145                 150                 155                 160

Thr Thr Cys Ala Asp Trp Val Val Ala Gly Phe Gly Ile His His Ser
                165                 170                 175

Ile Ala Asp Ala Phe Gln Lys Leu Ile Glu Pro Leu Ser Leu Tyr Ala
            180                 185                 190

His Ile Gln Trp Leu Thr Asn Ala Trp Gly Met Val Leu Leu Val Leu
        195                 200                 205

Ile Arg Phe Lys Val Asn Lys Ser Arg Cys Thr Val Ala Arg Thr Leu
    210                 215                 220

Gly Thr Leu Leu Asn Ile Pro Glu Asn His Met Leu Ile Glu Pro Pro
225                 230                 235                 240

Lys Ile Gln Ser Gly Val Ala Ala Leu Tyr Trp Phe Arg Thr Gly Ile
                245                 250                 255
```

```
Ser Asn Ala Ser Thr Val Ile Gly Glu Ala Pro Glu Trp Ile Thr Arg
            260                 265                 270

Gln Thr Val Ile Glu His Ser Leu Ala Asp Ser Gln Phe Lys Leu Thr
        275                 280                 285

Glu Met Val Gln Trp Ala Tyr Asp Asn Asp Ile Cys Glu Glu Ser Glu
    290                 295                 300

Ile Ala Phe Glu Tyr Ala Gln Arg Gly Asp Phe Asp Ser Asn Ala Arg
305                 310                 315                 320

Ala Phe Leu Asn Ser Asn Met Gln Ala Lys Tyr Val Lys Asp Cys Ala
            325                 330                 335

Ile Met Cys Arg His Tyr Lys His Ala Glu Met Lys Lys Met Ser Ile
            340                 345                 350

Lys Gln Trp Ile Lys Tyr Arg Gly Thr Lys Val Asp Ser Val Gly Asn
            355                 360                 365

Trp Lys Pro Ile Val Gln Phe Leu Arg His Gln Asn Ile Glu Phe Ile
        370                 375                 380

Pro Phe Leu Ser Lys Leu Lys Leu Trp Leu His Gly Thr Pro Lys Lys
385                 390                 395                 400

Asn Cys Ile Ala Ile Val Gly Pro Pro Asp Thr Gly Lys Ser Cys Phe
            405                 410                 415

Cys Met Ser Leu Ile Lys Phe Leu Gly Gly Thr Val Ile Ser Tyr Val
            420                 425                 430

Asn Ser Cys Ser His Phe Trp Leu Gln Pro Leu Thr Asp Ala Lys Val
            435                 440                 445

Ala Leu Leu Asp Asp Ala Thr Gln Pro Cys Trp Thr Tyr Met Asp Thr
        450                 455                 460

Tyr Met Arg Asn Leu Leu Asp Gly Asn Pro Met Ser Ile Asp Arg Lys
465                 470                 475                 480

His Arg Ala Leu Thr Leu Ile Lys Cys Pro Pro Leu Leu Val Thr Ser
            485                 490                 495

Asn Ile Asp Ile Ser Lys Glu Glu Lys Tyr Lys Tyr Leu His Ser Arg
            500                 505                 510

Val Thr Thr Phe Thr Phe Pro Asn Pro Phe Pro Phe Asp Arg Asn Gly
            515                 520                 525

Asn Ala Val Tyr Glu Leu Ser Asp Ala Asn Trp Lys Cys Phe Phe Glu
    530                 535                 540

Arg Leu Ser Ser Ser Leu Asp Ile Glu Asp Ser Glu Asp Glu Glu Asp
545                 550                 555                 560

Gly Ser Asn Ser Gln Ala Phe Arg Cys Val Pro Gly Ser Val Val Arg
            565                 570                 575

Thr Leu

<210> SEQ ID NO 79
<211> LENGTH: 14
<212> TYPE: PRT
<213> ORGANISM: C-terminal E1

<400> SEQUENCE: 79

Gln Ala Phe Arg Cys Val Pro Gly Ser Val Val Arg Thr Leu
  1               5                  10
```